US010478492B2

(12) United States Patent
Kolb et al.

(10) Patent No.: US 10,478,492 B2
(45) Date of Patent: Nov. 19, 2019

(54) MODIFICATIONS OF THERAPEUTIC AGENTS FOR ENHANCED DELIVERY TO TARGET SITES

(71) Applicant: Partikula LLC, Sunrise, FL (US)

(72) Inventors: David Kolb, Sunrise, FL (US); Petr Ledin, Plantation, FL (US); Tsukasa Mizuhara, Plantation, FL (US)

(73) Assignee: CLARIA PARTIKULA LLC, Dallas, TX (US)

( * ) Notice: Subject to any disclaimer, the term of this patent is extended or adjusted under 35 U.S.C. 154(b) by 39 days.

(21) Appl. No.: 15/660,256

(22) Filed: Jul. 26, 2017

(65) Prior Publication Data
US 2018/0028647 A1 Feb. 1, 2018

Related U.S. Application Data

(60) Provisional application No. 62/367,571, filed on Jul. 27, 2016, provisional application No. 62/400,320, filed on Sep. 27, 2016.

(51) Int. Cl.
A61K 39/39 (2006.01)
A61K 47/54 (2017.01)
A61K 47/66 (2017.01)
A61K 47/68 (2017.01)
A61K 47/69 (2017.01)
(Continued)

(52) U.S. Cl.
CPC ............ A61K 39/39 (2013.01); A61K 9/5146 (2013.01); A61K 47/54 (2017.08); A61K 47/541 (2017.08); A61K 47/542 (2017.08); A61K 47/555 (2017.08); A61K 47/66 (2017.08); A61K 47/6801 (2017.08); A61K 47/6809 (2017.08); A61K 47/6843 (2017.08); A61K 47/6851 (2017.08); A61K 47/6871 (2017.08); A61K 47/6889 (2017.08); A61K 47/6927 (2017.08); A61K 47/6929 (2017.08); A61K 2039/585 (2013.01)

(58) Field of Classification Search
None
See application file for complete search history.

(56) References Cited

U.S. PATENT DOCUMENTS

2010/0022680 A1  1/2010  Karnik

OTHER PUBLICATIONS

Adjeii, "Pharmacology and mechanism of action of pemetrexed". Clin Lung Cancer., 5 suppl 2:S51-5 (2004).
(Continued)

Primary Examiner — Karl J Puttlitz
(74) Attorney, Agent, or Firm — Pabst Patent Group LLP

(57) ABSTRACT

Compositions of a modulator of cell metabolism, typically targeting cellular glycolysis, preferably with a targeting moiety, attached directly or indirectly to the inhibitor, or to a nanoparticle or other delivery vehicle thereof, and methods of use for treating cancer, proliferative disorders, neurodegenerative diseases, autoimmune disorders, or inflammatory diseases are provided. Pharmaceutical compositions including the targeted modulator and a pharmaceutically acceptable carrier are also provided. The pharmaceutical compositions can be administered to a subject in need thereof in an effective amount to reduce one or symptoms of the cancer, proliferative disorders, neurodegenerative diseases, autoimmune disorders, or inflammatory diseases alone or prior to or in conjunction with a further therapy such as radiotherapy.

3 Claims, 1 Drawing Sheet

(51) Int. Cl.
　　　A61K 9/51　　　(2006.01)
　　　A61K 39/00　　(2006.01)

(56)　　　　　　References Cited

OTHER PUBLICATIONS

Babu, et al, "Role of SLC5A8, a plasma membrane transporter and a tumor suppressor, in the antitumor activity of dichloroacetate", Oncogene, 30:4026-37 (2011).
Cheong, et al, "Therapeutic targets in cancer cell metabolism and autophagy", Nat. Biotechnol., 30:671-678 (2012).
Coady, et al, "The human tumour suppressor gene SLC5A8 expresses a Na+-monocarboxylate cotransporter", J. Physiol., 557:719-31, (2004).
Coss, et al., "Intracellular Acidification Abrogates the Heat Shock Response and Compromises Survival of Human Melanoma Cells", Mol Cancer Ther., 2:383-8 (2003).
Diers, et al., "Pyruvate fuels mitochondrial respiration and proliferation of breast cancer cells: effect of monocarboxylate transporter inhibitionl", 444:561-71, Printed in Great Britain (2012).
Doherty and Cleveland, "Targeting lactate metabolism for cancer therapeutics", J Clin Invest., 123(9):3685-92 (2012).
Draoui, et al., "Lactate shuttles at a glance: from physiological paradigms to anti-cancer treatments", Dis. Model. Mech., 4(6):727-32 (2011).
Floridi, et al., "Effect of lonidamine on the energy metabolism of Ehrlich ascites tumor cells", Cancer Res., 41(11 Pt 1):4661-6 (1981).
Floridi, et al., "Action of the antitumor and antispermatogenic agent lonidamine on electron transport in Ehrlich ascites tumor mitochondria", Arch. Biochem. Biophys., 226:73-83 (1983).
Fukuyo, et al., "Geldanamycin and its anti-cancer activities", Cancer Lett., 290(1):24-35 (2010).
Gatenby, et al.,"Why do cancers have high aerobic glycolysis", Nat. Rev. Cancer, 4:891-899 (2004).
Gordon, "Amyotrophic Lateral Sclerosis: An update for 2013 Clinical Features, Pathophysiology, Management and Therapeutic Trials", Aging Disease, 4(5):295-310 (2013).
Halestrap. et al., "Specific inhibition of pyruvate transport in rat liver mitochondria and human erythrocytes by alpha-cyano-4-hydroxycinnamate", Biochem J., 138:313-6 (1974).
Kim, et al, "Cancer's molecular sweet tooth and the Warburg effect.", Cancer Res., 66:8927-30 (2006).
Ledford, et al., "Therapeutic cancer vaccine survives biotech bust", Nature, 519:17-18 (2015).
Li, et al, "SLC5A8, a sodium transporter, is a tumor suppressor gene silenced by methylation in human colon aberrant crypt foci and cancers", PNAS, 100:8412-7 (2003).
Macijauskiene, et al., "Dementia with Lewy bodies: the principles of diagnostics, treatment, and management", Medicina (Kaunas), 48(1):1-8 (2012).
Marrache. et al, "Engineering of blended nanoparticle platform for delivery of mitochondria-acting therapeutics", PNAS, 109:16288-16293 (2012).
Miyauchi. et al, "Functional identification of SLC5A8, a tumor suppressor down-regulated in colon cancer, as a Na(+)-coupled transporter for short-chain fatty acids", J. Biol. Chem., 279:13293-6 (2004).
Palucka, et al., "Cancer immunotherapy via dendritic cells", Nature Reviews Cancer, 12:265-77 ( 2012).
Pathak, et al., "Mito-DCA: a mitochondria targeted molecular scaffold for efficacious delivery of metabolic modulator dichloroacetate", ACS Chem. Biol., 9:1178-87 (2014).
Ross, et al, "Rapid and extensive uptake and activation of hydrophobic triphenylphosphonium cations within cells", Biochem. J, 411:633-45 (2008).
Samudio, et al, "Mitochondrial uncoupling and the Warburg effect: molecular basis for the reprogramming of cancer cell metabolism.", Cancer Res., 69:2163-6 (2009).
Smith, et al, "Delivery of bioactive molecules to mitochondria in vivo", PNAS,, 100:5407-12 (2003).
Spencer, et al., "L-lactate transport in Ehrlich ascites-tumour cells", Biochem J., 154:405-14 (1976).
Wahl, et al., "Regulation of intracellular pH in human melanoma: potential therapeutic implications", Mol Cancer Ther., 1:617-28 (2002).
Warburg, "On the origin of cancer cells", Science, 123:309-14 (1956).
Xiang, et al., Targeted inhibition of tumor-specific glutaminase diminishes cell-autonomous tumorigenesis, J Clin Invest., 125(6):2293-306 (2015).
Xu, et al., "Inhibition of glycolysis in cancer cells: a novel strategy to overcome drug resistance associated with mitochondrial respiratory defect and hypoxia", Cancer Res, 65:613-21 (2005).
Zhou, et al., "Warburg effect in chemosensitivity: targeting lactate dehydrogenase-A re-sensitizes taxol-resistant cancer cells to taxol", Mol Cancer., 9:33 1-12 (2010).
Zu, et al., "Cancer metabolism: facts, fantasy, and fiction", Biochem. Biophys. Res. Commun., 313:459-65 (2004).

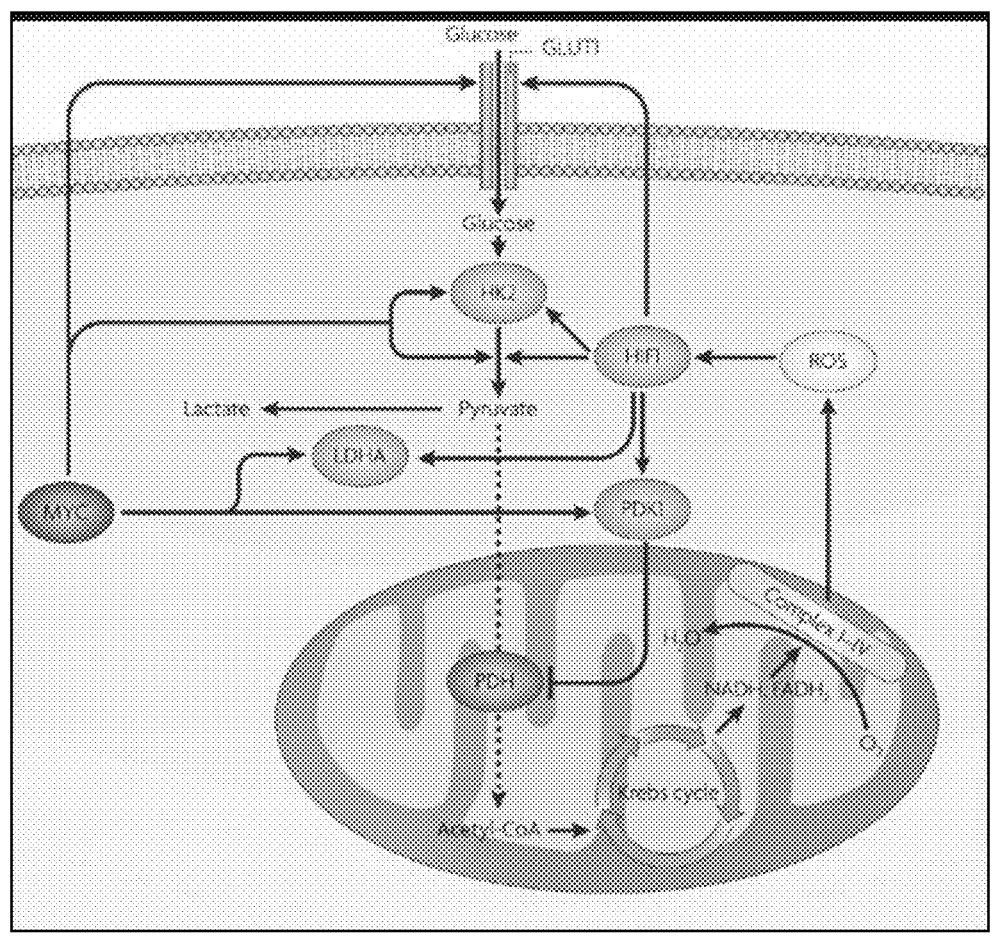

MODIFICATIONS OF THERAPEUTIC AGENTS FOR ENHANCED DELIVERY TO TARGET SITES

CROSS-REFERENCE TO RELATED APPLICATIONS

This application claims the benefit of and priority to U.S. Ser. No. 62/367,571, filed Jul. 27, 2016, and U.S. Ser. No. 62/400,320, filed Sep. 27, 2016, and where permissible are hereby incorporated by reference in their entirety.

FIELD OF THE INVENTION

The field of the invention generally relates to compositions and methods for treating cancer, proliferative disorders, neurodegenerative diseases, autoimmune disorders, or inflammatory diseases using compositions targeted to the disease environment, to reduce, alleviate, or prevent one or more symptoms associated with the disease.

BACKGROUND OF THE INVENTION

Metabolic aberrations in the form of altered flux through key metabolic pathways are primary hallmarks of many malignant tumors. Among the many adjustments of the metabolic pathways that are found in tumor cells, a key role is played by an enhanced aerobic glycolysis followed by lactic fermentation, which is also known as the Warburg effect (Warburg, O. *Science*, 123:309 (1956)). Normal cells generally transform glucose into carbon dioxide and water under aerobic conditions, by means of oxidative phosphorylation (OXPHOS). On the contrary, invasive cancer cells mostly produce lactate, even in the presence of sufficient levels of oxygen, even though this glycolytic pathway turns out to be less efficient than OXPHOS in producing ATP units. This apparently counterproductive behavior of cancer cells actually constitutes a survival advantage in rapidly proliferating cells, since it makes them insensitive to transient or permanent hypoxic conditions, it contributes to the production of nucleosides and amino acids, and constitutes a very rapid way to produce energy due to the enhanced glucose uptake occurring in cancer tissues. Lactate is not just a waste product of this process. It promotes tumor invasion by favoring cell migration, angiogenesis, immune escape and radioresistance (Draoui, N, et al., *Dis. Model. Mech.,* 4:727 (2011)). For example, rather than using lactate as a nutrient, cancer cells generally export lactate, leading to acidification of the tumor environment and a local inflammatory response that drives tumorigenesis (Doherty and Cleveland, *J Clin Invest.* 2013 Sep. 3; 123(9): 3685-3692). Lactate in the tumor cell microenvironment also appears to impair the adaptive immune response, disabling immune surveillance, in part by inhibiting immune cell metabolism.

Targeting this unique tumor metabolism can provide an alternative strategy to selectively destroy the tumor, leaving normal tissue unharmed (Warburg, *Science* 123:309-314 (1956), Zu et al., *Biochem. Biophys. Res. Commun.* 313:459-465 (2004), Samudio et al, *Cancer Res.* 69:2163-2166 (2009), Gatenby et al, *Nat. Rev. Cancer* 4:891-899 (2004), Kim et al, *Cancer Res.* 66:8927-8930 (2006), and Cheong et al, *Nat. Biotechnol.* 30:671-678 (2012)). The orphan drug dichloroacetate (DCA) is a mitochondrial kinase inhibitor that has the ability to show such characteristics. By utilizing the metabolic switch, DCA reverses the abnormal cancer cell metabolism from aerobic glycolysis to glucose oxidation by reducing the activity of mitochondrial pyruvate dehydrogenase kinase 1 (PDK1), which negatively regulates pyruvate dehydrogenase (PDH) causing pyruvate to convert to acetyl-CoA promoting oxidative phosphorylation (Bonnet et al. 2007). DCA reduces the high mitochondrial membrane potential ($\Delta\Psi m$) of cancer cells and increases mitochondrial reactive oxygen species (ROS) in malignant cells, but not in normal cells (Pathak R K et al., *ACS Chem. Biol.,* 9:1178-1187 (2014)).

However, therapeutically prohibitive high DCA doses are needed for suppression of tumor growth due to the lack of effective mechanisms for DCA entry into tumor cells and its localization inside the target organelle, mitochondria of cells. One recent study revealed a mitochondria-targeted DCA analogue, MITO-DCA, with a much improved cellular and mitochondrial uptake (Pathak R K et al., *ACS Chem. Biol.,* 9:1178-1187 (2014)). MITO-DCA uses a lipophilic triphenylphosphonium (TPP) cation moiety for the targeted delivery and accumulation into the mitochondrial matrix. The study showed that MITO-DCA efficiently reduced glycolytic functions, reduced basal cellular respiration, suppressed the calculated ATP synthesis, and attenuated the spare respiratory capacity in prostate cancer cells in vitro (Pathak R K et al., *ACS Chem. Biol.,* 9:1178-1187 (2014)).

However, targeted anti-cancer drugs such as MITO-DCA still face many challenges in accessing target sites in vivo, such as premature detachment of inhibitors from the targeting molecule, or fast elimination from the body.

Therefore, it is an object of the invention to provide compositions and methods that increase the stability of targeted anti-cancer agents, and minimize their premature breakdown before reaching their targeted site.

It is another object of the invention to provide compositions and methods that improve encapsulation of anti-cancer agents into drug delivery nanoparticles.

It is a further object of the invention to provide compositions and methods that increase the rate of delivery of therapeutics to disease environment in conditions such as cancer, proliferative disorders, neurodegenerative diseases, autoimmune disorders, or inflammatory diseases, for reducing, or alleviating one or more symptoms.

SUMMARY OF THE INVENTION

Compositions including an modulator of cancer cell metabolism and, preferably, a cancer cell- or a glucose-depleted and/or lactate-rich disease environment-targeting moiety, wherein the targeting moiety is associated with, linked, conjugated, or otherwise attached directly or indirectly to the modulator, or to a nanoparticle or other delivery vehicle thereof, and methods of use for treating cancer have been developed. In some embodiments, the modulator is itself a targeting moiety, optionally associated with, linked, conjugated, or otherwise attached directly or indirectly to one or more further modulators, targeting moieties, or combinations thereof. In some embodiments, the modulator reduces cancer cell glycolysis. The modulator can be, for example, a glucose transporter (GLUTs) inhibitor, a hexokinase inhibitor, a phosphofructokinase inhibitor, a glyceraldehyde-3-phosphate dehydrogenase (GAPDH) inhibitor, a phosphoglycerate mutase (PGM) inhibitor, an enolase (ENO) inhibitor, a pyruvate kinase (PK) activator, a lactate dehydrogenase inhibitor, a glutaminase (GLS) inhibitor, a pyruvate dehydrogenase (PDH) activator, a pyruvate dehydrogenase kinase inhibitor or a glucose-6-phosphate dehydrogenase (G6PD) inhibitor, an oxidative phosphorylation inhibitor, a glutaminase inhibitor, a glutamate dehydrogenase inhibitor, a mitochondrial citrate transporter SLC25A1

(CIC) inhibitor, and a dihydroorotate dehydrogenase inhibitor. In some embodiments, the modulator reduces the tricarboxylic acid (TCA) cycle in cancer cells. The modulator can also inhibit a monocarboxylate transporter (MCTs) in cancer cells. In some embodiments, the modulator is dichloracetate (DCA), dichloro acetophenone, 3-bromopyruvate (3BP), oxamic acid, lonidamine (LND), metformin, geldanamycin, bis-2-(5-phenylacetamido-1,3,4-thiadiazol-2-yl)ethyl sulfide (BPTES), 2-Cyano-3-(1-phenyl-1H-indol-3-yl)-2-propenoic acid (UK5099), 4-[3-chloro-4-[[(2R)-3,3,3-trifluoro-2-hydroxy-2-methylpropanoyl]amino]phenyl]sulfonyl-N,N-dimethylbenzamide (AZD7545), teriflunomide, 2[6(4-chlorophenoxy)hexyl]oxirane-2-carboxylate (etoximir), or ethoxyethanol.

Compositions including a modulator of cancer cell metabolism, wherein the modulator is conjugated to a hydrophobic moiety for enhanced encapsulation into a nanoparticle, and preferably a targeting moiety, wherein the targeting moiety is associated with, linked, conjugated, or otherwise attached directly or indirectly to the modulator, or to the nanoparticle and methods of use for treating cancer, are also provided. In some embodiments, the hydrophobic moiety is a substituted or unsubstituted long chain substituted or unsubstituted alkyl, alkylene, alkenyl, alkynyl, aryl, carbocyclyl, heteroalkyl, heteroaryl, heterocyclyl, arylalkyl, or acyl, etc. In preferred embodiments, the hydrophobic moiety is a substituted or unsubstituted alkyl group such as ethyl, octyl, palmityl, or tetradecyl group.

Preferably the modulator, for example, via the targeting moiety, is preferentially delivered to cancer cells. Preferably the modulator does not target or otherwise more than minimally modulate the metabolism of non-cancer cells, particular immune cells, or does so at a reduced level compared to cancer (e.g., tumor) cells. In this way, by-products and other effects associated with aberrant metabolism in cancer cells are reduced, preferably leading directly or indirectly to cancer cell death. In some embodiments, the targeting moiety is a mitochondria targeting moiety. In some embodiments, the targeting moiety is triphenylphosphonium (TPP). In some embodiments, the modulator reduces cancer cell migration, angiogenesis, immune escape and radioresistance. In preferred embodiments, the modulator induces a change in the cancer cell itself or its microenvironment that reduces suppression of, or induces activation of, an immune response against the cancer cell.

In some embodiments, the targeting moiety is a positively charged molecule at a physiological pH, preferably at the pH of the disease microenvironment. In preferred embodiments, the targeting moiety is a positively charged modulator such as metformin, imipramine, perphenazine, trifluoperazine, esomeprazole, omeprazole, celecoxib, tadalafil, rosuvastatin, sitagliptin, memantine, rivaroxaban, dabigatran etexilate mesylate, valsartan, dexlansoprazole, olmesartan, and lisdexamfetamine.

Compositions including an active agent for treating proliferative disorders, neurodegenerative diseases, autoimmune disorders, or inflammatory diseases, preferably, a disease environment-targeting moiety, wherein the targeting moiety is associated with, linked, conjugated, or otherwise attached directly or indirectly to the active agent, or to a nanoparticle or other delivery vehicle thereof, and methods of use for treating proliferative disorders, neurodegenerative diseases, autoimmune disorders, or inflammatory diseases have been developed. In some embodiments, the active agent is a modulator of cellular metabolism.

Pharmaceutical compositions including the modulator and a pharmaceutically acceptable carrier, and methods of use thereof for treating cancer, proliferative disorders, neurodegenerative diseases, autoimmune disorders, or inflammatory diseases are also provided. The pharmaceutical compositions can be administered to a subject in need thereof in an effective amount to reduce, alleviate, or prevent one or more symptoms of the cancer, proliferative disorders, neurodegenerative diseases, autoimmune disorders, or inflammatory diseases. In some embodiments, in subjects with tumors, the pharmaceutical compositions are effective to reduce tumor burden, reduce tumor progression, or a combination thereof.

Methods for treating subjects in need thereof using the compositions are also provided. The methods typically include administering to a subject in a need thereof an effective amount of a composition including a modulator of cancer metabolism. In some embodiments, the methods include administering to the subject one or more additional active agents or procedure such as radiation or surgical removal against cancer. The additional active agent can be a chemotherapeutic agent, for example, docetaxel or anti-tumor antibody. The pharmaceutical compositions can be administered prior to or in conjunction with an additional cancer therapy and/or procedure.

BRIEF DESCRIPTION OF THE DRAWINGS

FIG. 1 is a schematic showing tumor cells shift their metabolism to aerobic glycolysis, which is driven by multiple oncogenic signaling pathways. Hypoxia-inducible factor 1 (HIF1) increases the expression of glucose transporters (GLUT), glycolytic enzymes and pyruvate dehydrogenase kinase, isozyme 1 (PDK1), which blocks the entry of pyruvate into the tricarboxylic acid (TCA) cycle in mitochondria. MYC cooperates with HIF in activating several genes that encode glycolytic proteins, but also increases mitochondrial metabolism. Many cellular factors in tumor cells divert substrates into alternative biosynthetic and reduced nicotinamide adenine dinucleotide phosphate (NADPH)-generating pathways. The solid arrows indicate increased metabolic flux whereas the dashed arrows show a reduced metabolic flux in tumor cells. HK2, hexokinase-2; PDH: pyruvate dehydrogenase; LDHA: lactate dehydrogenase A; ROS: reactive oxygen species.

DETAILED DESCRIPTION OF THE INVENTION

I. Definitions

The term "carrier" or "excipient" refers to an organic or inorganic, natural or synthetic inactive ingredient in a formulation, with which one or more active ingredients are combined.

The terms "effective amount" or "therapeutically effective amount" means a dosage sufficient to alleviate one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the disease or disorder being treated, as well as the route of administration and the pharmacokinetics of the agent being administered.

The term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

The term "inhibit" or other forms of the word such as "inhibiting" or "inhibition" means to reduce, diminish, minimize, hinder or restrain a particular characteristic. It is understood that this is typically in relation to some standard or expected value, in other words it is relative, but that it is not always necessary for the standard or relative value to be referred to. For example, "inhibits" an enzyme means hindering or restraining the activity of the enzyme relative to a standard or a control. "Inhibits" can also mean to hinder or restrain the synthesis or expression of the enzyme relative to a standard or control.

The terms "treatment" or "treating" means to administer a composition to a subject or a system with an undesired condition (e.g., cancer or other proliferative disorder). The condition can include a disease.

The term "parenteral administration", means administration by any method other than through the digestive tract or non-invasive topical or regional routes. For example, parenteral administration may include administration to a patient intravenously, intradermally, intraperitoneally, intrapleurally, intratracheally, intramuscularly, subcutaneously, subjunctivally, by injection, and by infusion.

The term "topical administration", means the non-invasive administration to the skin, orifices, or mucosa. Topical administrations can be administered locally, i.e., they are capable of providing a local effect in the region of application without systemic exposure. Topical formulations can provide systemic effect via adsorption into the blood stream of the individual. Topical administration can include, but is not limited to, cutaneous and transdermal administration, buccal administration, intranasal administration, intravaginal administration, intravesical administration, ophthalmic administration, and rectal administration.

The term "enteral administration", means administration via absorption through the gastrointestinal tract. Enteral administration can include oral and sublingual administration, gastric administration, or rectal administration.

The term "pulmonary administration", means administration into the lungs by inhalation or endotracheal administration. As used herein, the term "inhalation" refers to intake of air to the alveoli. The intake of air can occur through the mouth or nose.

The terms "bioactive agent" and "active agent", used interchangeably, include, without limitation, physiologically or pharmacologically active substances that act locally or systemically in the body. A bioactive agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment.

The terms "positively charged" refers to the overall positive charge of an active agent, a targeting moiety, or their derivatives, at a physiologically relevant pH, for example, pH of the blood is about 7.3-7.5, and pH of the slightly more acidic tumor microenvironment is about pH 6.5-6.9. The positively charged active agent remains positively charged at least prior to, during, or after administration into a subject.

The terms "sufficient" and "effective", used interchangeably, refer to an amount (e.g. mass, volume, dosage, concentration, and/or time period) needed to achieve one or more desired result(s).

The term "biocompatible", refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

The term "biodegradable", generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "pharmaceutically acceptable", refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. A "pharmaceutically acceptable carrier", as used herein, refers to all components of a pharmaceutical formulation which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

The term "molecular weight", generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "small molecule", generally refers to an organic molecule that is less than about 2000 g/mol in molecular weight, less than about 1500 g/mol, less than about 1000 g/mol, less than about 800 g/mol, or less than about 500 g/mol. Small molecules are non-polymeric and/or non-oligomeric.

The term "dendrimer", includes, but is not limited to, a molecular architecture with an interior core, interior layers (or "generations") of repeating units regularly attached to this initiator core, and an exterior surface of terminal groups attached to the outermost generation. Dendrimers have regular dendrimeric or "starburst" molecular structures.

The term "copolymer", generally refers to a single polymeric material that includes two or more different monomers. The copolymer can be of any form, such as random, block, graft, etc. The copolymers can have any end-group, including capped or acid end groups.

The term "hydrophilic", refers to substances that have strongly polar groups that readily interact with water.

The term "hydrophobic", refers to substances that lack an affinity for water; tending to repel and not absorb water as well as not dissolve in or mix with water.

The term "lipophilic", refers to compounds having an affinity for lipids.

The term "amphiphilic", refers to a molecule combining hydrophilic and lipophilic (hydrophobic) properties.

The term "mean particle size", generally refers to the statistical mean particle size (diameter) of the particles in the composition. The diameter of an essentially spherical particle may be referred to as the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering. Two populations can be said to have a "substantially equivalent mean particle size" when the statistical mean particle size of the first population of nanoparticles is within 20% of the statistical mean particle size of the second population of nanoparticles; more preferably within 15%, most preferably within 10%.

The terms "monodisperse" and "homogeneous size distribution", used interchangeably, describe a population of particles, microparticles, or nanoparticles all having the same or nearly the same size. As used herein, a monodisperse distribution refers to particle distributions in which 90% of the distribution lies within 5% of the mean particle size.

The term "targeting moiety", refers to a moiety that binds to or localizes to a specific locale. The moiety may be, for example, a protein, nucleic acid, nucleic acid analog, carbohydrate, or small molecule. The locale may be a tissue, a particular cell type, or a subcellular compartment. The targeting moiety or a sufficient plurality of targeting moieties may be used to direct the localization of a particle or an active entity.

The term "reactive coupling group", refers to any chemical functional group capable of reacting with a second functional group to form a covalent bond. The selection of reactive coupling groups is within the ability of the skilled artisan. Examples of reactive coupling groups can include primary amines (—NH$_2$) and amine-reactive linking groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugate to amines by either acylation or alkylation. Examples of reactive coupling groups can include aldehydes (—COH) and aldehyde reactive linking groups such as hydrazides, alkoxyamines, and primary amines. Examples of reactive coupling groups can include thiol groups (—SH) and sulfhydryl reactive groups such as maleimides, haloacetyls, and pyridyl disulfides. Examples of reactive coupling groups can include photoreactive coupling groups such as aryl azides or diazirines. The coupling reaction may include the use of a catalyst, heat, pH buffers, light, or a combination thereof.

The term "protective group", refers to a functional group that can be added to and/or substituted for another desired functional group to protect the desired functional group from certain reaction conditions and selectively removed and/or replaced to deprotect or expose the desired functional group. Protective groups are known to the skilled artisan. Suitable protective groups may include those described in Greene, T. W. and Wuts, P. G. M., Protective Groups in Organic Synthesis, (1991). Acid sensitive protective groups include dimethoxytrityl (DMT), tert-butylcarbamate (tBoc) and trifluoroacetyl (tFA). Base sensitive protective groups include 9-fluorenylmethoxycarbonyl (Fmoc), isobutyrl (iBu), benzoyl (Bz) and phenoxyacetyl (pac). Other protective groups include acetamidomethyl, acetyl, tert-amyloxycarbonyl, benzyl, benzyloxycarbonyl, 2-(4-biphenylyl)-2-propyloxycarbonyl, 2-bromobenzyloxycarbonyl, tert-butyl, tert-butyloxycarbonyl, 1-carbobenzoxamido-2,2,2-trifluoroethyl, 2,6-dichlorobenzyl, dimethoxyphenyl)-2-propyloxycarbonyl, 2,4-dinitrophenyl, dithiasuccinyl, formyl, 4-methoxybenzenesulfonyl, 4-methoxybenzyl, 4-methylbenzyl, o-nitrophenylsulfenyl, 2-phenyl-2-propyloxycarbonyl, α-2,4,5-tetramethylbenzyloxycarbonyl, p-toluenesulfonyl, xanthenyl, benzyl ester, N-hydroxysuccinimide ester, p-nitrobenzyl ester, p-nitrophenyl ester, phenyl ester, p-nitrocarbonate, p-nitrobenzylcarbonate, trimethylsilyl and pentachlorophenyl ester.

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Aryl," as used herein, refers to $C_5$-$C_{26}$-membered aromatic, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups, for example, benzene, naphthalene, anthracene, phenanthrene, chrysene, pyrene, corannulene, coronene, etc.

"Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with an heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Alkyl," as used herein, refers to the radical of saturated aliphatic groups, including straight-chain alkyl, alkenyl, or alkynyl groups, branched-chain alkyl, cycloalkyl (alicyclic), alkyl substituted cycloalkylgroups, and cycloalkyl substituted alkyl. In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; —NO$_2$; —COOH; carboxylate; —COR, —COOR, or —CON(R)$_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as —CF$_3$, —CH$_2$—CF$_3$, —CCl$_3$); —CN; —NCOCOCH$_2$CH$_2$, —NCOCOCHCH; —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), haloalkyls, and —CN. Cycloalkyls can be substituted in the same manner.

The terms "alkenyl" and "alkynyl" refer to unsaturated aliphatic groups analogous in length and possible substitution to the alkyls described above, but that contain at least one double or triple bond, respectively.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenyl" is art recognized, and refers to the aromatic moiety —C$_6$H$_5$, i.e., a benzene ring without one hydrogen atom.

The term "substituted phenyl" refers to a phenyl group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Amino" and "Amine," as used herein, are art-recognized and refer to both substituted and unsubstituted amines, e.g., a moiety that can be represented by the general formula:

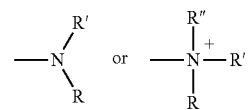

wherein, R, R', and R'' each independently represent a hydrogen, substituted or unsubstituted alkyl, substituted or unsubstituted alkenyl, substituted or unsubstituted alkynyl, substituted or unsubstituted carbonyl, —(CH$_2$)$_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' (and optionally R'') each independently represent a hydrogen atom, substituted or unsubstituted alkyl, a substituted or unsubstituted alkenyl, or —(CH$_2$)$_m$—R'''. Thus, the term 'alkylamine' as used herein refers to an amine group, as defined above, having a substituted or unsubstituted alkyl attached thereto (i.e. at least one of R, R', or R'' is an alkyl group).

"Carbonyl," as used herein, is art-recognized and includes such moieties as can be represented by the general formula:

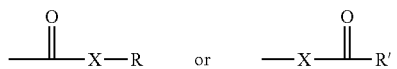

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R'', or a pharmaceutical acceptable salt, R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl or —(CH$_2$)$_m$—R''; R'' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defines as above, the moiety is also referred to as a carboxyl group. When X is oxygen and R is hydrogen, the formula represents a 'carboxylic acid'. Where X is oxygen and R' is hydrogen, the formula represents a 'formate'. Where X is oxygen and R or R' is not hydrogen, the formula represents an "ester". In general, where the oxygen atom of the above formula is replaced by a sulfur atom, the formula represents a 'thiocarbonyl' group. Where X is sulfur and R or R' is not hydrogen, the formula represents a 'thioester.' Where X is sulfur and R is hydrogen, the formula represents a 'thiocarboxylic acid.' Where X is sulfur and R' is hydrogen, the formula represents a 'thioformate.' Where X is a bond and R is not hydrogen, the above formula represents a 'ketone.' Where X is a bond and R is hydrogen, the above formula represents an 'aldehyde.'

The term "substituted carbonyl" refers to a carbonyl, as defined above, wherein one or more hydrogen atoms in R, R' or a group to which the moiety

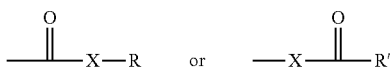

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "carboxyl" is as defined above for the formula

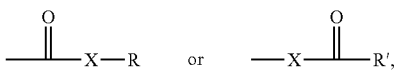

and is defined more specifically by the formula —$R^{iv}$COOH, wherein $R^{iv}$ is an alkyl, alkenyl, alkynyl, cycloalkyl, heterocyclyl, alkylaryl, arylalkyl, aryl, or heteroaryl. In preferred embodiments, a straight chain or branched chain alkyl, alkenyl, and alkynyl have 30 or fewer carbon atoms in its backbone (e.g., $C_1$-$C_{30}$ for straight chain alkyl, $C_3$-$C_{30}$ for branched chain alkyl, $C_2$-$C_{30}$ for straight chain alkenyl and alkynyl, $C_3$-$C_{30}$ for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure.

The term "substituted carboxyl" refers to a carboxyl, as defined above, wherein one or more hydrogen atoms in $R^{iv}$ are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfa- moyl, sulfonamido, sulfonyl, heterocyclyl, alkylaryl, haloalkyl, —CN, aryl, heteroaryl, and combinations thereof.

"Heteroalkyl," as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

Examples of saturated hydrocarbon radicals include, but are not limited to, methyl, ethyl, n-propyl, isopropyl, n-butyl, t-butyl, isobutyl, sec-butyl, cyclohexyl, (cyclohexyl) methyl, cyclopropylmethyl, and homologs and isomers of, for example, n-pentyl, n-hexyl, n-heptyl, n-octyl. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, and 3-butynyl.

The terms "alkoxyl" or "alkoxy," "aroxy" or "aryloxy," generally describe compounds represented by the formula —$OR^v$, wherein $R^v$ includes, but is not limited to, substituted or unsubstituted alkyl, alkenyl, alkynyl, cycloalkyl, heterocyclyl, cycloalkenyl, heterocycloalkenyl, aryl, heteroaryl, arylalkyls, heteroalkyls, alkylaryl, alkylheteroaryl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The term alkoxy also includes cycloalkyl, heterocyclyl, cycloalkenyl, heterocycloalkenyl, and arylalkyl having an oxygen radical attached to at least one of the carbon atoms, as valency permits.

The term "substituted alkoxy" refers to an alkoxy group having one or more substituents replacing one or more hydrogen atoms on one or more carbons of the alkoxy backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenoxy" is art recognized, and refers to a compound of the formula —$OR^v$ wherein $R^v$ is (i.e., —O—$C_6H_5$). One of skill in the art recognizes that a phenoxy is a species of the aroxy genus.

The term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "aroxy" and "aryloxy," as used interchangeably herein, are represented by —O-aryl or —O-heteroaryl, wherein aryl and heteroaryl are as defined herein.

The terms "substituted aroxy" and "substituted aryloxy," as used interchangeably herein, represent —O-aryl or —O-heteroaryl, having one or more substituents replacing one or more hydrogen atoms on one or more ring atoms of the aryl and heteroaryl, as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto.

The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenylthio" is art recognized, and refers to —S—$C_6H_5$, i.e., a phenyl group attached to a sulfur atom.

The term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Arylthio" refers to —S-aryl or —S-heteroaryl groups, wherein aryl and heteroaryl as defined herein.

The term "substituted arylthio" represents —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Arylalkyl," as used herein, refers to an alkyl group that is substituted with a substituted or unsubstituted aryl or heteroaryl group.

"Alkylaryl," as used herein, refers to an aryl group (e.g., an aromatic or hetero aromatic group), substituted with a substituted or unsubstituted alkyl group.

The terms "amide" or "amido" are used interchangeably, refer to both "unsubstituted amido" and "substituted amido" and are represented by the general formula:

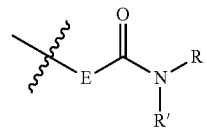

wherein, E is absent, or E is substituted or unsubstituted alkyl, substituted or unsubstituted alkenyl, substituted or unsubstituted alkynyl, substituted or unsubstituted aralkyl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' each independently represent a hydrogen atom, substituted or unsubstituted alkyl, a substituted or unsubstituted alkenyl, or —$(CH_2)_m$—R'''. When E is oxygen, a carbamate is formed. The carbamate cannot be attached to another chemical species, such as to form an oxygen-oxygen bond, or other unstable bonds, as understood by one of ordinary skill in the art.

The term "sulfonyl" is represented by the formula

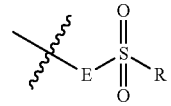

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', or E and R taken together with the S atom to which they are attached complete a heterocycle having from 3 to 14 atoms in the ring structure;

R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of E and R can be substituted or unsubstituted amine, to form a "sulfonamide" or "sulfonamido." The substituted or unsubstituted amine is as defined above.

The term "substituted sulfonyl" represents a sulfonyl in which E, R, or both, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "sulfonic acid" refers to a sulfonyl, as defined above, wherein R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl.

The term "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

The term "sulfonate" refers to a sulfonyl, as defined above, wherein E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

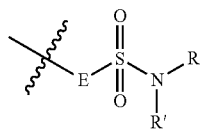

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide.

The term "phosphonyl" is represented by the formula

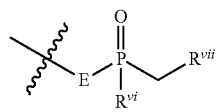

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein, independently of E, R$^{vi}$ and R$^{vii}$ are independently hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the P atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "substituted phosphonyl" represents a phosphonyl in which E, R$^{vi}$ and R$^{vii}$ are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phosphoryl" defines a phoshonyl in which E is absent, oxygen, alkoxy, aroxy, substituted alkoxy or substituted aroxy, as defined above, and independently of E, R$^{vi}$ and R$^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, $R^{vi}$ and $R^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof.

The term "substituted polyaryl" refers to a polyaryl in which one or more of the aryls, heteroaryls are substituted, with one or more substituents including, but not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof. The term "$C_3$-$C_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. The cyclic structures are formed from single or fused ring systems. The substituted cycloalkyls, cycloalkenyls, cycloalkynyls and heterocyclyls are substituted as defined above for the alkyls, alkenyls, alkynyls and heterocyclyls, respectively.

The terms "hydroxyl" and "hydroxy" are used interchangeably and are represented by —OH.

The terms "thiol" and "sulfhydryl" are used interchangeably and are represented by —SH.

The term "oxo" refers to =O bonded to a carbon atom.

The terms "cyano" and "nitrile" are used interchangeably to refer to —CN.

The term "nitro" refers to —$NO_2$.

The term "phosphate" refers to —O—$PO_3$.

The term "azide" or "azido" are used interchangeably to refer to —$N_3$.

As used herein, the term "tumor cell" or "cancer cell", denotes a cell which may be malignant (i.e., capable of metastasis and the mediation of disease), or benign. In contrast, a "non-tumor cell" is a normal cell (which may be quiescent or activated) that is located within a tumor microenvironment, including, but not limited to Tumor Infiltrating Lymphocytes (TILs), leucocytes, macrophages, and/or other cells of the immune system, and/or stromal cells, and/or fibroblasts (e.g., cancer or tumor associated fibroblasts).

II. Compositions

Direct or indirect inhibition of lactate production by cancer cells can influence the tumor microenvironment and thereby activate exhausted or dormant immune cells and/or help to influence the number of immune cells in the microenvironment. It has been established that energetics can be used to influence the microenvironment of cancers with immunological activity or inactivity.

Compositions for preferentially modulating metabolism in cancer cells are provided. The compositions generally include a cell metabolism modulator optionally in, on, or otherwise associated with a delivery vehicle such a nanoparticle, microsphere, dendrimer, antibody, or conjugate. In some embodiments, the compositions are targeted to a glucose-depleted and/or lactate-rich disease environment.

In the most preferred embodiments, the compositions lead to (a) direct or indirect inhibition of glycolysis or oxidative phosphorylation or any other form of metabolism that utilizes glucose or equivalents from the disease area's microenvironment or direct or indirect inhibition of the uptake of glucose or equivalents from the disease area microenvironment, and/or (b) direct or indirect inhibition of the production of lactate or equivalents, or the direct or indirect inhibition of the release of lactate or equivalents into the disease microenvironment.

Typically the composition includes a moiety or other modification that increases delivery of the modulator to the cancer cells relative to non-cancer cells, and particularly immune cells. In some embodiments, the composition include a moiety (e.g., a mitochondrial localization signal) or other characteristic (e.g., EPR, zeta potential of the delivery vehicle, etc.,), or combination thereof that enhances delivery to the mitochondria. In the most preferred embodiments, the composition is designed for delivery to (a) the tumor microenvironment generally or preferentially, and/or (b) to the cancer cells in the microenvironment.

Therapeutic targets that effect metabolism include, but are not limited to, glucose transporters (GLUT family), monocarboxylate transporters (MCTs) (MCT family), proteins involved in glycolysis such as hexokinase (HK family), lactate dehydrogenase (LDH family), pyruvate dehydrogenase (PDH), pyrvuate dehydrogenase kinase (PDK family), glyceraldehyde-3-phosphate dehydrogenase (GAPDH), phosphofructokinase, glucose-6-phosphate dehydrogenase (G6PD), members of the tricarboxylic acid (TCA) cycle such as succinate dehydrogenase (SDH family), isocitrate dehydrogenase (IDH family) and members involved in oxidative phosphorylation such as Complex 1 proteins, phosphoglycerate mutase (PGM), enolase (ENO), HSP90, CPT1, glutaminase, glutamate dehydrogenase, mitochondrial citrate transporter SLC25A1 (CIC), and dihydroorotate dehydrogenase.

Exemplary preferred delivery vehicles are discussed in U.S. Published Application No. 2014/0303081, which is specifically incorporated by reference herein in its entirety. In some embodiments, the delivery vehicle is a mitochondrial-targeted PLGA-PEG-TPP nanoparticle containing a metabolic modulating compound such as those disclosed herein.

A. Targeted Agents

Targeted agents generally are one or more modulators of desired function e.g., inhibiting glycolysis in cancer cells, preferably, optionally, attached to a targeting moiety (TM) for enhanced localization of the drug at the target site.

In some embodiments, modifications to the modulators are to incorporate hydrophobic side chains to enhance their rate of incorporation into their delivery vesicle such as nanoparticles. In one aspect, the compounds can be represented by Formula I:

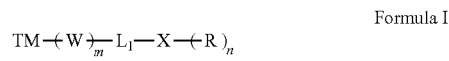

Formula I wherein

TM is hydrogen, a targeting moiety, or

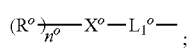

;

W is substituted alkyl, unsubstituted alkyl, substituted alkylene, unsubstituted alkylene, substituted alkenyl, unsubstituted alkenyl, substituted alkynyl, unsubstituted alkynyl, substituted alkoxy, unsubstituted alkoxy, substituted aryl, unsubstituted aryl, substituted heteroaryl, unsubstituted heteroaryl, substituted $C_3$-$C_{30}$ cycloalkyl, unsubstituted $C_3$-$C_{30}$ cycloalkyl, substituted heterocyclyl, unsubstituted heterocyclyl, substituted amino, unsubstituted amino, substituted alkylamino, unsubstituted alkylamino, substituted alkylthio, or unsubstituted alkylthio;

X, and $X^o$ are, independent from one another, a linking chemical moiety that connects one or more modulators (M) to the rest of the compound;

R is, independently for each occurrence, -$L_2$-$L_3$-$L_4$-$L_5$-M, $R^o$ is, independently for each occurrence, -$L_2^o$-$L_3^o$-$L_4^o$-$L_5^o$-$M^o$, M, $M^o$ for each occurrence are, independently, absent, or a modulator, such as dichloroacetate (DCA), dichloro acetophenone, 3-bromopyruvate (3BP), oxamic acid, lonidamine (LND), metformin, geldanamycin, bis-2-(5-phenylacetamido-1,3,4-thiadiazol-2-yl)ethyl sulfide (BPTES), 2-Cyano-3-(1-phenyl-1H-indol-3-yl)-2-propenoic acid (UK5099), 4-[3-chloro-4-[[(2R)-3,3,3-trifluoro-2-hydroxy-2-methylpropanoyl]amino]phenyl]sulfonyl-N,N-dimethylbenzamide (AZD7545), teriflunomide, 2[6(4-chlorophenoxy)hexyl]oxirane-2-carboxylate (etoximir), or ethoxyethanol;

$L_1$, $L_2$, $L_3$, $L_4$, $L_5$, $L_1^o$, $L_2^o$, $L_3^o$, $L_4^o$, and $L_5^o$ are independently absent, —C(O)NH—, —C(O)NR'—, —NR'C(O)—, —C(O)O—, —OC(O)—, —C(O)OCH$_2$—, —SO$_2$NR'—, —CH$_2$R'—, —O—, —NR'H—, —NR'—, —OCONH—, —NHCOO—, —OCONR'—, —NR'COO—, —NHCONH—, —NR'CONH—, —NHCONR'—, —NR'CONR'—, —CHOH—, —CR'OH—, unsubstituted alkyl (such as unsubstituted $C_1$-$C_{20}$ alkyl), substituted alkyl (such as substituted $C_1$-$C_{20}$ alkyl), substituted alkylene (such as substituted $C_1$-$C_{20}$ alkylene), substituted alkenyl (such as substituted $C_1$-$C_{20}$ alkenyl), unsubstituted alkenyl (such as unsubstituted $C_1$-$C_{20}$ alkenyl), substituted alkylamino (such as substituted $C_1$-$C_{20}$ alkylamino), unsubstituted alkylamino (such as unsubstituted $C_1$-$C_{20}$ alkylamino), substituted carbonyl (such as substituted $C_1$-$C_{20}$ carbonyl), or unsubstituted carbonyl (such as unsubstituted carbonyl);

R' is hydrogen, halogen (F, Cl, Br, I), hydroxyl, unsubstituted alkyl (such as unsubstituted $C_1$-$C_{20}$ alkyl), substituted alkyl (such as substituted $C_1$-$C_{20}$ alkyl), substituted alkylene (such as substituted $C_1$-$C_{20}$ alkylene), unsubstituted alkylene (such as unsubstituted $C_1$-$C_{20}$ alkylene), substituted alkenyl (such as substituted $C_1$-$C_{20}$ alkenyl), unsubstituted alkenyl (such as unsubstituted $C_1$-$C_{20}$ alkenyl), substituted alkylamino (such as substituted $C_1$-$C_{20}$ alkylamino), unsubstituted alkylamino (such as unsubstituted $C_1$-$C_{20}$ alkylamino), substituted carbonyl (such as substituted $C_1$-$C_{20}$ carbonyl), or unsubstituted carbonyl (such as unsubstituted $C_1$-$C_{20}$ carbonyl), an aryl group, or a heterocyclic group;

m is an integer between 0 and 17, inclusive; and n, and $n^o$ are, independent from each other, an integer between 1 and 10, inclusive.

In some embodiments, X is

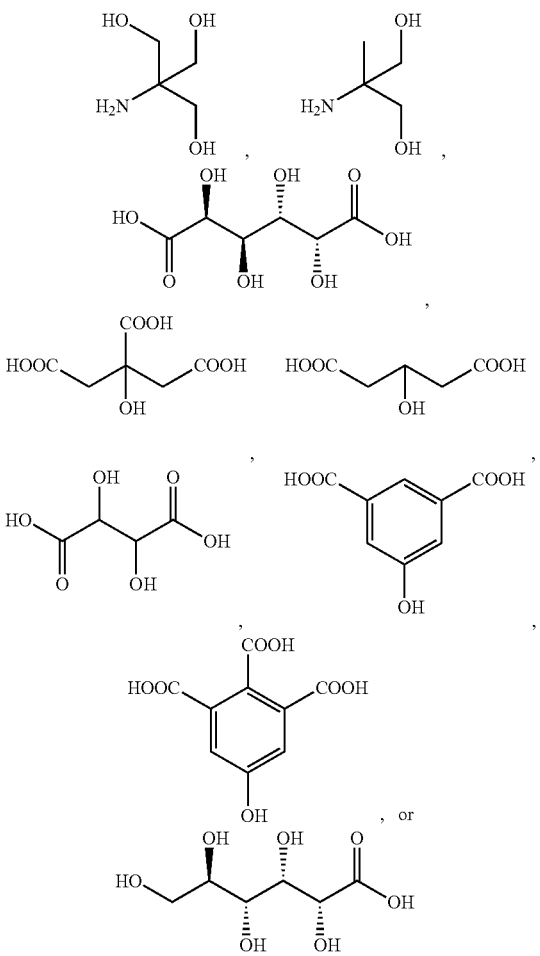

, or

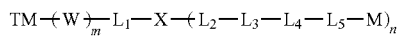

.

In some embodiments, the compounds are represented by Formula II,

Formula II

TM—(W)$_m$—L$_1$—X—(L$_2$—L$_3$—L$_4$—L$_5$—M)$_n$ wherein

TM, W, m, $L_1$, $L_2$, $L_3$, $L_4$, $L_5$, and M are as defined above for Formula I;

X is a substituted alkyl, such as a substituted $C_1$-$C_{12}$ alkyl.

n is an integer between 1 and 3, inclusive.

In some aspects, $L_1$, $L_2$, $L_3$, $L_4$, and $L_5$ are independently absent, —C(O)NH—, —C(O)NR'—, —NR'C(O)—, —C(O)O—, —OC(O)—, —SO$_2$NR'—, —CH$_2$R'—, —O—, —NR'H—, —NR'—, unsubstituted alkyl (such as unsubstituted $C_1$-$C_{12}$ alkyl), substituted alkyl (such as substituted $C_1$-$C_{12}$ alkyl), substituted alkylene (such as substituted $C_1$-$C_{12}$ alkylene); wherein R' is hydrogen, halogen (F, Cl, Br, I), hydroxyl, unsubstituted alkyl (such as unsubstituted $C_1$-$C_{12}$ alkyl, e.g. CH$_3$—), substituted alkyl (such as substituted $C_1$-$C_{12}$ alkyl), substituted alkylene (such as substituted $C_1$-$C_{12}$ alkylene), or unsubstituted alkylene (such as unsubstituted $C_1$-$C_{12}$ alkylene).

In some aspects, at least one of $L_1$, $L_2$, $L_3$, $L_4$, and $L_5$, is an amide linkage. In other aspects, $L_1$, $L_2$, $L_3$, $L_4$, and $L_5$ are as defined above for Formula I, with the provision that one of $L_1$, $L_2$, $L_3$, $L_4$, and $L_5$ is not an ester. In some aspects, at least one of $L_1^o$, $L_2^o$, $L_3^o$, $L_4^o$, and $L_5^o$, is an amide linkage. In other aspects, $L_1^o$, $L_2^o$, $L_3^o$, $L_4^o$, and $L_5^o$ are as defined above for Formula I, with the provision that one of $L_1^o$, $L_2^o$, $L_3^o$, $L_4^o$, and $L_5^o$ is not an ester.

In some embodiments, the modulator is an anti-cancer drug. In further embodiments, the modulator is a glucose transporter (GLUTs) inhibitor, a hexokinase inhibitor, a phosphofructokinase inhibitor, a glyceraldehyde-3-phosphate dehydrogenase (GAPDH) inhibitor, a phosphoglycerate mutase (PGM) inhibitor, an enolase (ENO) inhibitor, a lactate dehydrogenase inhibitor, a pyruvate dehydrogenase kinase (PDK) inhibitor, a glucose-6-phosphate dehydrogenase (G6PD) inhibitor, a tricarboxylic acid (TCA) cycle inhibitor, or a monocarboxylate transporter (MCTs) inhibitor, a HSP90 inhibitor, a CPT1 inhibitor, an oxidative phosphorylation inhibitor, a glutaminase inhibitor, a glutamate dehydrogenase inhibitor, a mitochondrial citrate transporter SLC25A1 (CIC) inhibitor, and a dihydroorotate dehydrogenase inhibitor. In preferred embodiments, the modulator is dichloracetate (DCA), 3-bromopyruvate (3BP), oxamic acid, lonidamine (LND), metformin, geldanamycin, bis-2-(5-phenylacetamido-1,3,4-thiadiazol-2-yl)ethyl sulfide (BPTES), 2-Cyano-3-(1-phenyl-1H-indol-3-yl)-2-propenoic acid (UK5099), 4-[3-chloro-4-[[(2R)-3,3,3-trifluoro-2-hydroxy-2-methylpropanoyl]amino]phenyl]sulfonyl-N, N-dimethylbenzamide (AZD7545), teriflunomide, 2[6(4-chlorophenoxy)hexyl]oxirane-2-carboxylate (etoximir), or ethoxyethanol.

In some embodiments, the modulator is a positively charged molecule at a physiological pH, such as metformin, imipramine, perphenazine, trifluoperazine, esomeprazole, omeprazole, celecoxib, tadalafil, rosuvastatin, sitagliptin, memantine, rivaroxaban, dabigatran etexilate mesylate, valsartan, dexlansoprazole, olmesartan, and lisdexamfetamine. In some embodiments, the modulator is modified to have a positively charged molecule at a physiological pH such as addition of amine groups.

In some embodiments, the modulator is modified to have desired chemical properties for incorporation into delivery vehicles, for example, via conjugation with a hydrophobic group such as palmityl, octyl, or tetradecyl group.

In other embodiments, the targeting moiety is not directly conjugated to the modulator, but instead associated with the same nanoparticle for the targeted delivery. In further embodiments, both targeting moiety and modulator are independently modified for better encapsulation into nanoparticles so in such cases, targeting moiety and modulator are associated with each other via their interactions with the same nanoparticle.

In some embodiments, the modulators have the property of targeting to an area of interest such as a tumor site. In these cases, the modulators are by themselves targeted agents, optionally conjugated with further chemical groups for desired functionalities. These modulators can be conjugated directly, or indirectly, to one or more hydrophobic side chains for enhanced incorporation into a delivery vehicle, or to one or more additional targeting features. For example, metformin, being positive charged, is accounted for its accumulation within the matrix of energized mitochondria, without any further targeting moiety. Therefore, in a specific embodiment, the targeted agent is metformin. In yet another embodiment, the targeted agent is palmityl derivatives of metformin. In this case, TM is hydrogen in Formula I, and the long alkyl chain such as C1-C20 is linked to metformin via one or more L groups, such as $L_2$-$L_3$-$L_4$-$L_5$.

In further embodiments, modulators having the inherent property of targeting to a site of interest, are used as a targeting moiety for a second active agent. In this case, TM is

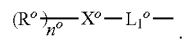

For example, metformin can be conjugated directly, or indirectly to one or more active agent such as BPTES. In this case, $M^o$ is metformin, and M is BPTES. These two modulators, or their derivatives such as palmitoylated metformin, are conjugated via one or more L groups, such as $L_2$-$L_3$-$L_4$-$L_5$. Alternatively, metformin, and BPTES can be independently conjugated to separate alkyl groups, which are subsequently incorporated into the same micelle, or nanoparticle for delivery.

1. Targeting Moiety (TM)

The composition can include one or more targeting moieties associated with, linked, conjugated, or otherwise attached directly or indirectly to the modulator of cancer cell metabolism, or to a nanoparticle or other delivery vehicle thereof. The targeting elements may refer to elements that bind to or otherwise localize the nanoparticles to a specific locale. The locale may be a tissue, a particular cell type, or a subcellular compartment. In some embodiments, the composition includes a targeting moiety can, for example, target the composition to cancer cells or a tumor microenvironment, target the mitochondria, or a combination thereof. In some embodiments, the modulators or the nanoparticles can include targeting moieties that specifically bind to targeted molecules. A positive feedback loop is created when the nanoparticles release an inducing agent that causes a targeted cell, tissue or organ to increase the expression or bioavailability of the targeted molecules specifically recognized by the targeting moiety.

In some embodiments, the targeting moiety is pH sensitive, lactate sensitive, acid sensitive, or mitochondrial membrane potential sensitive. In some embodiments, the moiety is one that keeps the composition away from the immune cells, or healthy cells.

Representative targeting moieties include, but are not limited to, antibodies and antigen binding fragments thereof, aptamers, peptides, and small molecules. The targeting moiety can be conjugated to a hydrophobic group, e.g., a polymer that incorporates into the nanoparticle. Typically the targeting moiety is displayed on the outer shell of the nanoparticle. In some embodiments, the outer shell serves as a shield to prevent the nanoparticles from being recognized by a subject's immune system thereby increasing the half-life of the nanoparticles in the subject. In some embodiments, the nanoparticles also contain a hydrophobic core. The nanoparticles are suitable for systemic, intraperitoneal, oral, pulmonary, or topical administration. The nanoparticles also optionally include a detectable label, for example, a fluorophore or NMR contrast agent that allows visualization of nanoparticles within the diseased area.

The targeting moiety can be an antibody or antigen binding fragment thereof. The targeting moieties should have an affinity for a cell-surface receptor or cell-surface antigen on the targeted organs, tissues, cells, and/or subcellular organelles.

The targeting moiety can specifically recognize and bind to a target molecule specific for a cell type, a tissue type, or an organ. The targeted molecule can be a cell surface polypeptide, lipid, or glycolipid. The target molecule can be a receptor that is selectively expressed on a specific cell surface, a tissue or an organ. Cell specific markers can be for specific types of cells including, but not limited to stem cells, skin cells, blood cells, immune cells, muscle cells, nerve cells, cancer cells, virally infected cells, and organ specific cells. The cell markers can be specific for endothelial, ectodermal, or mesenchymal cells. Representative cell specific markers include, but are not limited to cancer specific markers.

In some embodiments, the targeting moiety is a positively charged molecule at a physiological pH, and/or at a pH of a targeted region e.g., at tumor microenvironment. In preferred embodiments, the targeting moiety is a positively charged therapeutic agent at physiological pH, and/or at pH of the target site. For example, metformin can be used as a targeting moiety to delivery itself, and/or a further active agent to a tumor site via direct, or indirect conjugation, or loading onto the same drug delivery vehicle. Some exemplary therapeutic agents that are positively charged at physiological pH are metformin, imipramine, perphenazine, trifluoperazine, esomeprazole, omeprazole, celecoxib, tadalafil, rosuvastatin, sitagliptin, memantine, rivaroxaban, dabigatran etexilate mesylate, valsartan, dexlansoprazole, olmesartan, and lisdexamfetamine. In some embodiments, these modulators with targeting properties are used to target a further therapeutic agent to address one or more aspects of the disease e.g., one for treating the cause of the disease, and another for alleviating one or more disease-associated symptoms. For example, an anti-cancer agent with targeting properties e.g., metformin is directly or indirectly linked to an anti-inflammatory agent.

In further embodiments, therapeutic agents are modified to have desired targeting functionalities. For example, amine groups are added to the therapeutic agents, or their derivatives to make the overall charges of the targeted agents positive.

In some embodiments, metformin and derivatives thereof are the targeting moieties for delivering one or more further modulators.

i. Mitochondria Targeting Moiety

In some embodiments, mitochondria targeting moiety is incorporated as the targeting moiety (TM) in the composition. Mitochondria targeting moiety is a moiety that targets the mitochondria by selectively delivering the compound to or accumulating the compound in the mitochondria. The mitochondrial target moiety can be any cationic molecules such as cationic ligands, cationic proteins, cationic polymers, and cationic polymer-peptide conjugates, mitochondrial localization signals, and protein transduction domains.

Exemplary mitochondria targeting moieties (TM) that can be incorporated into the compounds are delocalized lipophilic cations, which are effective at crossing the hydrophobic membranes and accumulating in the mitochondria. Triphenylphosphonium (denoted TPP or (Ph)$_3$P+) containing compounds can accumulate greater than 10 fold within the mitochondria matrix. Any therapeutically acceptable TPP-containing compound can be used as the mitochondria targeting moiety TM in the compounds. Another delocalized lipophilic cation that can be used as TM in the compounds is dequalinium.

In other examples, the mitochondria targeting moiety can be a rhodamine cation such as Rhodamine 123. Rhodamine 6G can also be used.

Chemical Structure of Rhodamine 123

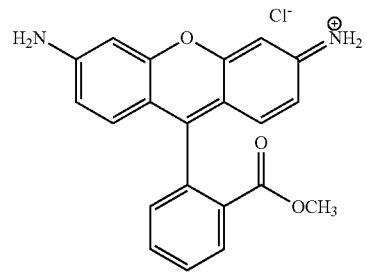

In further embodiments, non-cationic compounds serve to target and accumulate the compounds in the mitochondria matrix. For example, Szeto-Schiller peptides can serve as suitable mitochondria targeting moieties in the compounds to target and accumulate the inhibitor in the mitochondria matrix. Any suitable Szeto-Schiller peptide can be used in the compounds. Non limiting examples include SS-02 (H-2', 6'-dimethyl-tyrosine-D-Arg-Phe-Lys-NH$_2$), SS-20 (H-Phe-D-Arg-Phe-Lys-NH$_2$), and SS-31 (H-D-Arg-2',6'-dimethyl-tyrosine-Lys-Phe-NH$_2$).

2. Modulators (M)

Modulator (M) is a chemical moiety that is an active agent when attached to any modification tags such as a targeting moiety, or when free (i.e., when cleaved from targeting moiety). Therefore, M is a modulator of a targeted pathway, either an agonist or an antagonist, to achieve a desired therapeutic, or prophylactic effect. In some embodiment, a modulator is capable of reducing, alleviating, or preventing one or more symptoms of a condition selected from the group consisting of cancer, autoimmune disorders, inflammatory disorders, and neurodegenerative disorders.

The increased dependence of cancer cells on the glycolytic pathway for ATP generation provides a biochemical basis for the design of therapeutic strategies to preferentially kill cancer cells.

Compositions and methods for direct or indirect pharmacological inhibition of cancer cell metabolism, including glycolysis in cancer cells, are provided. Targets of inhibitions include: (1) glycolytic enzymes directly involved in glycolysis, and glucose transporters (GLUTs), which control the availability of glucose for tumor growth; (2) enzymes involved in interconnected pathways such as pentose phosphate pathway and TCA cycle; (3) monocarboxylate transporters, which transport lactate in or from tumor cells (e.g., PPP pathway, glutamine pathway, etc.). Therefore, in some cases, the modulator is a glucose transporter (GLUTs) inhibitor, a hexokinase inhibitor, a phosphofructokinase inhibitor, a glyceraldehyde-3-phosphate dehydrogenase (GAPDH) inhibitor, a phosphoglycerate mutase (PGM) inhibitor, an enolase (ENO) inhibitor, a lactate dehydrogenase inhibitor, a pyruvate dehydrogenase kinase (PDK) inhibitor, a glucose-6-phosphate dehydrogenase (G6PD) inhibitor, an inhibitor that inhibits components of the tricarboxylic acid (TCA) cycle, or an inhibitor that inhibits a monocarboxylate transporter (MCTs) in cancer cells, an oxidative phosphorylation inhibitor, a glutaminase inhibitor, a glutamate dehydrogenase inhibitor, a mitochondrial citrate transporter SLC25A1 (CIC) inhibitor, and a dihydroorotate dehydrogenase inhibitor.

In some embodiments, modulators are agonists that promote cellular oxidative metabolism. For example, AMP-activated protein kinase (AMPK) is believed to act in opposition to the metabolic phenotypes favored by proliferating tumor cells. Thus, in some embodiments, the modulators are AMPK agonists such as metformin, phenformin, 5-aminoimidazole-4-carboxamide ribonucleotide (AICAR), 2-deoxy-D-glucose (2DG), salicylate, and A-769662.

In the most preferred embodiments, the modulator is a small molecule, such as those discussed in more detail below. The term "small molecule" refers to small organic compounds having a molecular weight of more than 100 and less than about 2,500 daltons, preferably between 100 and 2000, more preferably between about 100 and about 1250, more preferably between about 100 and about 1000, more preferably between about 100 and about 750, more preferably between about 200 and about 500 daltons. The small molecules often include cyclical carbon or heterocyclic structures and/or aromatic or polyaromatic structures substituted with one or more functional groups.

Some exemplary modulator are dichloracetate (DCA), a pyruvate dehydrogenase kinase (PDK) inhibitor, 3-bromopyruvate (3BP), a hexokinase (HK) inhibitor, oxamic acid, a lactate dehydrogenase (LDH) inhibitor, Lonidamine (LND), a HK inhibitor and MCT inhibitor. Other exemplary inhibitors include geldanamycin, a HSP90 inhibitor, ethoxyethanol, a CPT1 inhibitor, bis-2-(5-phenylacetamido-1,3,4-thiadiazol-2-yl)ethyl sulfide (BPTES), a glutaminase inhibitor, 2-Cyano-3-(1-phenyl-1H-indol-3-yl)-2-propenoic acid (UK5099), a mitochondrial pyruvate transporter inhibitor, 4-[3-chloro-4-[[(2R)-3,3,3-trifluoro-2-hydroxy-2-methyl-propanoyl]amino]phenyl]sulfonyl-N,N-dimethylbenzamide (AZD7545), a pyruvate dehydrogenase kinase 2 (PDHK2) inhibitor, teriflunomide, a dihydroorotate dehydrogenase inhibitor, and 2[6(4-chlorophenoxy)hexyl]oxirane-2-carboxylate (etoximir), a fatty acid oxidation inhibitor, 4-chloro-3-[[(3-nitrophenyl)amino]sulfonyl] benzoic acid, and benzenetricarboxylate (BTA), mitochondrial citrate transport protein (CTP) Inhibitors, and ethoxyethanol, a carnitine palmitoyltransferase I (CPT1).

In other embodiments, the modulator can be a functional nucleic acid such those discussed in more detail below. Suitable targets, and inhibitors and activators thereof, are discussed in Pelicano, et al, *Oncogene* (2006) 25, 4633-4646 and in more detail below.

Other exemplary modulators that can be incorporated into the compounds include mitochondrial acting anti-cancer agents. For example, the M can be a modulator of the BCL-3 protein family, such as compounds that act on BCL-XL, BCL-2, BCL-1, MCL1, or the like; compounds that affect HK, affect HK2-VDAC interaction, PDK inhibitors, affect LDH-A, affect fatty acid synthase, affect ATP citrate lyase, acetyl-CoA carboxylase inhibitors, or the like; VDAC-targeting or ANT-targeting agents; ROS regulators such as SOD inhibitors, GSH inhibitors, GPX inhibitors or the like; HSP90 inhibitor or the like. Examples of specific inhibitors M that can be present in the compounds include lonidamine, dichloroacetate, alpha-tocopheryl succinate, methyl jasmonate, betulinic acid, and resveratrol, A-385358, ABT-263, ABT-737, AT-101, 2-amino-6-bromo-4-(1-cyano-2-ethoxy-2-oxoethyl)-4H-chromene-3-carboxylate (HA 14-1), LDH-A shRNA, orlistat, SB-204990, soraphen A, 4-(N-(s-glutathionylacetate)aminophenylarsenoxide (GSAO), clodronate, PK1 1195, menadione, beta-lapachone, CD437, gamitrinibs, 8-(2-chloro-3,4,5-trimethoxybenzyl)-2-fluoro-9-(pent-4-nyl)-9H-purin-6-amine (PU24Fcl), (8-(6-bromobenzo[d][1,3,]dioxyl-5-ylthio)-9-(pent-4-nyl)-9H-purin-6-amine (PUH58), 8-(6-iodobenzo[d][1,3,]dioxyl-5-ylthio)-9-(3-isopropylamino)propyl-9H-purin-6-amine (PUH71), shepherdin, 2-methoxy estradiol, tetrathiomolybdate, buthionine sulphoximine, dimethylamino-parthenolide, parthenolide, imexons, magafodipir, menadione, motexafin gadolinium, PEITCs, elescomol (STA-4783), all trans-retinoic acid, 6-[3-(1-adamantyl)-4-hydroxyphenyl]-2-naphthalene carboxylic acid, E-3-(4'-hydroxy-3'-adamantylbiphenyl-4yl) acrylic acid, 3-bromopyruvate, butyric acid, 2-deoxyD-glucose, arsenite trioxide, betulinic acid, and the like.

In certain examples, the modulator is a Bcl-2 inhibitor, such as oblimersen sodium, AT-101, ABT-263, GX15-070, gossypol, TW-37, ApoG2, ABT 737, and obatoclax.

i. DCA & Derivatives

Dichloroacetate (DCA) is a water-soluble small molecule PDK inhibitor with excellent therapeutic abilities. One of the limitations of the molecule is its poor availability at the target site due to lack of targeting abilities. DCA encounters tremendous barriers in its navigation to enter the mitochondria. The monocarboxylate transporters which are linked to DCA cellular entry are electroneutral in most cells including tumor (Jackson et al, *J. Biol. Chem.* 271:861-868, 1996). Lactate, pyruvate, and ketone bodies are natural substrates for this transport system; hence DCA faces strong competition with these substrates for its uptake. Moreover, for mitochondrial uptake, DCA competes with pyruvate for its entry via the mitochondrial pyruvate transporter. Studies identified a new sodium-coupled monocarboxylate transporter (SMCT1) or solute carrier family-5 member-8 (SLC5A8), which is linked in the transport of acetate, propionate, butyrate, lactate, pyruvate, 3-bromopyruvate, nicotinate, and evidenced that this highly energy-coupled transporter would accept DCA as a substrate. (Coady et al, *J. Physiol.* 557:719-731, 2004; Miyauchi et al, *J. Biol. Chem.* 279: 13293-13296 (2004)). However, this transporter is expressed in normal cells, but expression is silenced in tumor cells. (Li et al, Proc. Natl. Acad. Sci. USA 100:8412-8417 (2003); Babu et al, Oncogene 30:4026-4037 (2011)). Thus the lack of SLC5A8 makes tumor cells resistant to the anti-tumor activity of DCA.

Lactate is the most abundant product of highly glycolytic tumor and some of the effects of high levels of extracellular lactate include: blocking of monocyte differentiation to dendritic cells (DCs), significant inhibition of cytokine release from DCs and cytotoxic T lymphocytes, inhibition of monocyte migration, and reduction of cytotoxic T-cell function (Gottfried et al, Blood 107:2013-2021, 2006). Inhibition of glycolysis using DCA can overcome immune suppressive nature of glycolytic tumor; however, it needs very high DCA doses. Taking advantage of the fact that cancer cells frequently have more negatively charged mitochondria, a lipophilic mitochondria targeting moiety, e.g., triphenylpohsphonium (TPP) cation, has been used for targeted delivery of DCA, which equilibrates across the membranes in a Nernstian fashion and accumulates into the mitochondrial matrix space in inverse proportion to A i/m. (Smith et al, *Proc. Natl. Acad. Sci. USA* 100:5407-5412 (2003); Ross et al, *Biochem. J.* 411:633-645 (2008); Marrache et al, *Proc. Natl Acad. Sci. USA* 109: 16288-16293 (2012); Marrache et al, *Proc. Natl Acad. Sci. USA* 109: 16288-16293 (2012)).

In some embodiments, the compositions are derivatives of dichloroacetate, for example, modified with a β-alanyl group for enhanced stability of the amide linkage before further conjugation to other groups such as Tris, or one or more targeting moieties. Modifications with hydrophobic groups such as alkyl groups allow for improved encapsulation into nanoparticles. In some embodiments, these nanoparticles also encapsulate free dichloroacetate.

In some embodiments, the derivative is dichloroacetophenones.

ii. 3-bromo-2-oxopropanoate & Derivatives 3-bromopyruvate is also an inhibitor of hexokinase and has been shown to abolish ATP production and cause severe depletion of cellular ATP). 3-BP exhibits potent cytotoxic activity against cancer cells with mitochondrial respiratory defects and cells in hypoxic environment (Xu R H et al., Cancer Res 65:613-621 (2005)). In addition to inhibiting HK, 3-bromopyruvate is also a potent inhibitor of glyceraldeyde-3-phosphate dehydrogenase (GAPDH) by reacting with the —SH nucleophile sites of these enzymes through the rapid displacement of its bromo-leaving group.

In some embodiments, the compositions are derivatives of 3-bromopyruvate, for example, modified with a long chain alkyl group such as octyl, and tetradecyl, allowing for improved encapsulation into nanoparticles. In some embodiments, these nanoparticles also encapsulate free 3-bromopyruvate. In some embodiments, derivatization of 3-bromopyruvate involves direct conjugation of a targeting moiety.

iii. Oxamate & Derivatives

In some embodiments, the modulators are inhibitors of lactate dehydrogenase A (LDHA). Oxamate is an inhibitor of lactate dehydrogenase A (LDHA), which is the enzyme that converts pyruvate to lactate and oxidizes the reduced form of nicotinamide adenine dinucleotide (NADH) to NAD+. Oxamate has shown to sensitize resistant cancer cells to chemotherapeutic agents (Zhou M et al., Mol Cancer. 9:33 (2010)). Oxamate salt is commercially available (Sigma-Aldridge #O2751).

In some embodiments, the compositions are derivatives of oxamate, for example, modified with a long chain alkyl group such as octyl. In this case, the long hydrophobic octyl group allows more efficient loading of this derivative into a nanoparticle for drug delivery. In some embodiments, these nanoparticles also encapsulate free oxamate. In some embodiments, derivatization of oxamate involves direct conjugation of a targeting moiety. In other embodiments, the targeting moiety is not directly conjugated to the modulator, but instead associated with the same nanoparticle for the targeted delivery.

iv. Metformin & Derivatives

Metformin is a clinically approved drug by the FDA to treat type II diabetes, targets the mitochondrial complex I and thereby reducing ATP synthesis. In some embodiments, the modulators are inhibitors of mitochondrial complex I.

In some embodiments, the compositions are derivatives of metformin, for example, modified with a long chain alkyl group, for example C1-C20 alkyl groups, or substituted forms thereof. The addition of these long hydrophobic groups allows more efficient loading of this derivative into a nanoparticle for drug delivery. Alternatively, the long hydrophobic tails assemble into micelles for delivery with the active agent exposed on the outer surface of the micelles.

In some embodiments, derivatization of metformin involves direct conjugation of a targeting moiety (TM). In other embodiments, derivatives of metformin and one or more targeting moieties are associated with the same nanoparticle for targeted delivery.

v. Geldanamycin & Derivatives

Geldanamycin is a benzoquinone ansamycin antibiotic that manifests anti-cancer activity through the inhibition of HSP90-chaperone function. The HSP90 molecular chaperone is expressed at high levels in a wide variety of human cancers including melanoma, leukemia, and cancers in colon, prostate, lung, and breast. In cancer cells dependent upon mutated and/or over-expressed oncogene proteins, HSP90 is thought to have a critical role in regulating the stability, folding, and activity of HSP90-associated proteins, so-called "client proteins". These client proteins include the growth-stimulating proteins and kinases that support malignant transformation (Fukuyo Y et al., Cancer Lett. 290(1): 24-35(2010)).

In some embodiments, the compositions are derivatives of geldanamycin, for example, palmityl geldanamycin. In this case, the long hydrophobic palmityl group allows more efficient loading of this derivative into a nanoparticle for drug delivery. In some embodiments, these nanoparticles also encapsulate free geldanamycin. In some embodiments, derivatization of geldanamycin involves direct conjugation of a targeting moiety (TM).

vi. Ethoxyethanol & Derivatives

In some embodiments, the modulators are inhibitors of carnitine palmitoyltransferase I (CPT1). In some embodiments, the compositions are derivatives ethoxyethanol. Ethoxyethanol is an inhibitor of carnitine palmitoyltransferase I (CPT1) that decreases beta oxidation in the mitochondria. Another example of CPT1 inhibitor is etomoxir.

vii. Lonidamine & Derivatives

Lonidamine (also known as TH-070) is a derivative of indazole-3-carboxylic acid, and has been known for a long time to inhibit aerobic glycolysis in cancer cells (Floridi et al., Cancer Res., 41(11 Pt 1):4661-6 (1981)). The proven ability of lonidamine to inhibit energy metabolism in cancer cells and to enhance the activity of other anticancer agents has led to extensive clinical trial in many cancer models.

In addition to inhibiting hexokinase, lonidamine was also shown to inhibit MCTs, which prevents lactate export from cells and causes intracellular acidification (Ben-Yoseph, O. et al., J. Neurooncol. 36, 149-157 (1998)). It was also reported that lonidamine could inhibit mitochondrial electron transport chain (Floridi, A. et al., Arch. Biochem. Biophys. 226, 73-83 (1983)). However, the mechanism underlying this inhibition is not clear.

In some embodiments, the compositions are derivatives of lonidamine, for example, modified with a long chain alkyl group for increased hydrophobicity. In some embodiments, derivatization of lonidamine also involves direct conjugation of a targeting moiety (TM).

viii. Cyanohydroxycinnamic Acid & Derivatives

In some embodiments, the modulators are inhibitors of monocarboxylate transporters (MCT). The "classic" inhibitors of monocarboxylate transporters (MCT) have been derivatives of cinnamic acid, first identified by Halestrap and co-workers for their effect on isolated mitochondrial pyruvate transport (Halestrap A P, et al., Biochem J. 1974; 138:313-316.), and by Lehninger and co-workers on intact Ehrich ascites tumor (Spencer T L, et al., Biochem J. 1976; 154:405-414.). The latter study and studies by others (Wahl M L, et al., Mol Cancer Ther. 2002; 1:617-628; Coss R A, et al., Mol Cancer Ther. 2003; 2:383-388) have indicated the cinnamic acid derivatives to be competitive inhibitors of lactate transport in tumors, with α-cyano-4-hydroxy cinnamic acid (ACCA), a commonly utilized off-the-shelf chemical used as a matrix during mass spectrometry, as one of the more potent inhibitors of lactate transport, with a Ki of 0.5 mM.

In some embodiments, the compositions are derivatives of cyanohydroxycinnamic acid, for example, tetradecyl-cyanohydroxycinnamic acid. In this case, the long hydrophobic alkyl group allows more efficient loading of this derivative into a nanoparticle for drug delivery. In some embodiments, these nanoparticles also encapsulate free cyanohydroxycinnamic acid. In some embodiments, derivatization of cyanohydroxycinnamic acid also involves direct conjugation of a targeting moiety (TM).

ix. Mitochondrial Citrate Transport Protein (CTP) Inhibitor & Derivatives

In some embodiments, the modulators are mitochondrial citrate transport protein (CTP) Inhibitors such as 1,2,3-benzenetricarboxylate (BTA), 4-chloro-3-[[(3-nitrophenyl)amino]sulfonyl] benzoic acid, and n-butylmalonate (BM). The Mitochondrial Citrate Transport Protein (CTP) Inhibitor, 4-chloro-3-[[(3-nitrophenyl)amino]sulfonyl] benzoic acid, also referenced under CAS 412940-35-3, controls the biological activity of Mitochondrial Citrate Transport Protein (CTP). It is commercially available (EMD MILLIPORE #475877).

In some embodiments, the compositions are derivatives of 4-chloro-3-[[(3-nitrophenyl)amino]sulfonyl] benzoic acid, or 1,2,3-benzenetricarboxylate (BTA), for example, conjugated with a long chain alkyl group such as tetradecyl. In this case, the long hydrophobic alkyl group allows more efficient loading of this derivative into a nanoparticle for drug delivery. In some embodiments, derivatization of 4-chloro-3-[[(3-nitrophenyl)amino]sulfonyl]benzoic acid, or 1,2,3-benzenetricarboxylate (BTA) also involves direct conjugation of a targeting moiety (TM).

x. AZD7545 & Derivatives

In some embodiments, the modulators are PDHK inhibitors. AZD7545 is a potent PDHK inhibitor with IC50 of 36.8 nMjnbn and 6.4 nM for PDHK1 and PDHK2, respectively. In primary rat hepatocytes, AZD7545 increases PDH activity with EC50 of 105 nM (Mayers R M, et al. *Biochem Soc Trans.* 31(Pt 6), 1165-1167 (2003)). AZD7545 inhibits PDHK activity by disrupting the interactions between PDHK2 and the inner lipoyl-bearing domains (L2) of the dihydrolipoyl transacetylase component (E2) of PDC (Tuganova A, et al. *Biochemistry.* 46(29), 8592-8602 (2007)).

In some embodiments, the compositions are derivatives of AZD7545, for example, conjugated with a long chain alkyl group, and/or a targeting moiety (TM).

xi. BPTES & Derivatives

In some embodiments, the modulators are Glutaminase GLS1inhibitors. Bis-2-(5-phenylacetamido-1,3,4-thiadiazol-2-yl)ethyl sulfide (BPTES) is a selective inhibitor of Glutaminase GLS1. Glutaminase (GLS), which converts glutamine to glutamate, plays a key role in cancer cell metabolism, growth, and proliferation (Xiang Y et al., *J Clin Invest.* 125(6):2293-306 (2015)).

In some embodiments, the compositions are derivatives of BPTES, for example, conjugated with a long chain alkyl group, and/or a targeting moiety (TM). Long hydrophobic alkyl group allows more efficient loading of BPTES, or its derivatives into a nanoparticle for drug delivery. In some embodiments, this incorporation results in BPTES exposed at the surface of the nanoparticles. In other embodiments, this incorporation results in BPTES buried at, or near the core of the nanoparticles.

xii. Pemetrexed & Derivatives

In some embodiments, the modulators are inhibitors to folate metabolism and purine and pyrimidine synthesis. Pemetrexed is a novel multitargeted antifolate that inhibits > or =3 enzymes involved in folate metabolism and purine and pyrimidine synthesis. These enzymes are thymidylate synthase, dihydrofolate reductase, and glycinamide ribonucleotide formyltransferase (Adjeii A A, *Clin Lung Cancer.* 5 Suppl 2:S51-5(2004)).

In some embodiments, the compositions are derivatives of pemetrexed, for example, conjugated with a long chain alkyl group, and/or a targeting moiety (TM). Long hydrophobic alkyl group allows more efficient loading of pemetrexed, or its derivatives into a nanoparticle for drug delivery. In some embodiments, this incorporation results in pemetrexed exposed at the surface of the nanoparticles. In other embodiments, this incorporation results in pemetrexed buried at, or near the core of the nanoparticles.

3. Linkages for Enhanced Stability

In one aspect, the compounds are engineered for stability for efficient uptake at the targeted site, for example, cancer cellul, and/or mitochondria, to induce anti-cancer activity at the target site. The compounds can also enhance the effects of anti-tumor immunity at pharmacologically relevant doses.

In some embodiments, the modulator is modified by simple chemical modifications to enhance one or more of the following properties: 1) abilities to target to specific site(s) e.g., mitochondria, 2) stability of modified analogues of the modulators i.e., to prevent premature degradation/elimination before reaching the targeted site(s), and 3) rate of encapsulation within a delivery vesicle e.g., a nanoparticle.

i. β-alanyl-DCA

The use of the comparatively stable amide linkage for DCA conjugation to alanyl allow targeting MITO-ADCA to the mitochondria whilst minimizing any premature detachment of the targeting moiety from DCA before reaching the mitochondria of cells. In some embodiments, β-alanyl-DCA is used to further conjugate to one or more targeting moieties, to long hydrophobic side chains.

Formula III

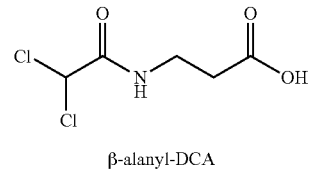

β-alanyl-DCA

In some embodiments, the alanyl-modification reduces the rate of premature detachment of the targeting moiety from DCA (e.g., Mito-ADCA) before reaching the mitochondria of any target cells by 5%, 10%, 20%, 30%, 40%, 50%, 60%, 70%, 80%, 90%, or more than 90% compared to without alanyl-modification such as in Mito-DCA.

In some embodiments, the alanyl-modification increases the rate of accumulation at the target site by 5%, 10%, 20%, 30%, 40%, 50%, 60%, 70%, 80%, 90%, or more than 90% compared to without alanyl-modification such as in Mito-DCA.

ii. TPP-ADCA

A single ADCA conjugated to a single triphenylpohsphonium moiety (TPP-ADCA) is also described, which contains one DCA per TPP molecule.

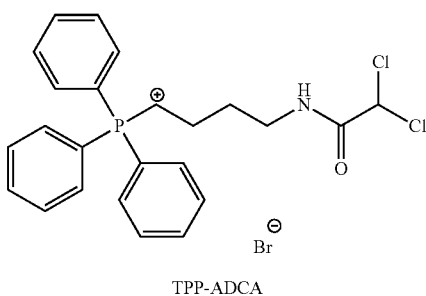

Formula IV

TPP-ADCA iii. TPP-Tris-β-alanino-DCA (Mito-ADCA)

MITO-ADCA can be activated by the enzymes present in the mitochondria to release the active drug for its accumulation in the PDK1 binding pocket. In MITO-ADCA, the mitochondria targeting TPP cation is introduced via an amide linkage and multiple ADCA molecules were incorporated via tris(hydroxymethyl)aminomethane (Tris) via ester bonds.

To construct MITO-ADCA, TPP-Tris-(OH)$_3$ is first synthesized by reacting (5-carboxypentyl)triphenylphosphonium bromide with Tris using N-ethoxycarbonyl-2-ethoxy-1,2-dihydroquinoline (EEDQ), a highly specific reagent that enables the coupling of amine with carboxyl in the presence of hydroxyl groups. The hydroxyl groups from TPP-Tris-(OH)$_3$ are coupled to Boc protected beta-alanine. Once the Boc protection groups are removed, DCA anhydride is added to produce Mito-ADCA. Coupling other inhibitors M to the TPP-Tris-(OH)$_3$ intermediate can be accomplished in a similar manner.

MITO-ADCA contains three DCA moieties per TPP molecule, allowing the delivery of higher DCA dose using one targeting ligand. This can translate to increased therapeutic benefit. Thus, MITO-ADCA has the potential to deliver more drug dose using a single TPP targeting moiety. Similar delivery efficiency can be expected with the other inhibitors to be conjugated.

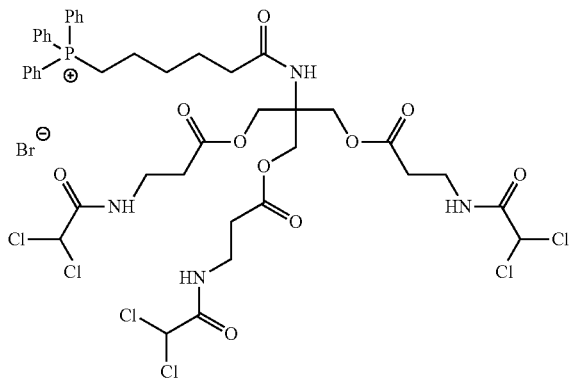

Formula V

TPP-Tris-β-alanino-DCA

In some embodiments, alanino-DCA is conjugated to at least one of the three hydroxyl groups from TPP-Tris-(OH) 3. In some embodiments, alanino-DCA is conjugated to any one of the three hydroxyl groups from TPP-Tris-(OH)3 whilst the other two are conjugated to DCA. In further embodiments, alanino-DCA is conjugated to any two of the three hydroxyl groups from TPP-Tris-(OH)3 whilst the third hydroxyl group is conjugated to DCA. Some exemplary structures are shown in Formulae VI-IX.

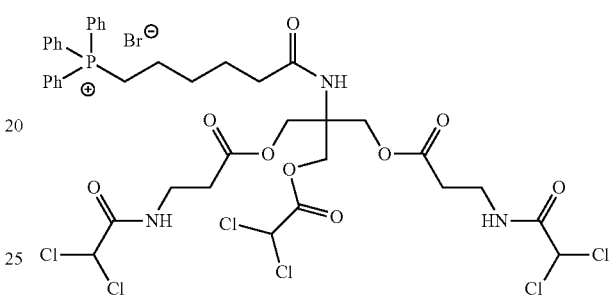

Mito(AD-D-AD)
Formula VI: TPP- Tris conjugated to two β-alanino-DCA and one DCA

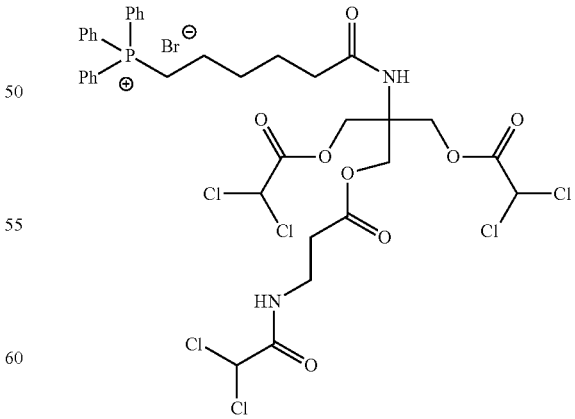

Mito(D-AD-D)
Formula VII: TPP- Tris conjugated to one β-alanino-DCA and two DCA

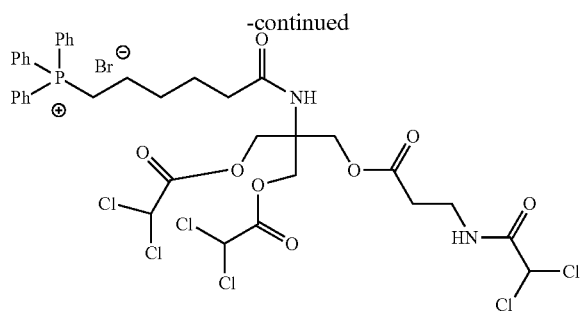

Mito(D-D-AD)
Formula VIII: TPP- Tris conjugated to one β-alanino-DCA and two DCA

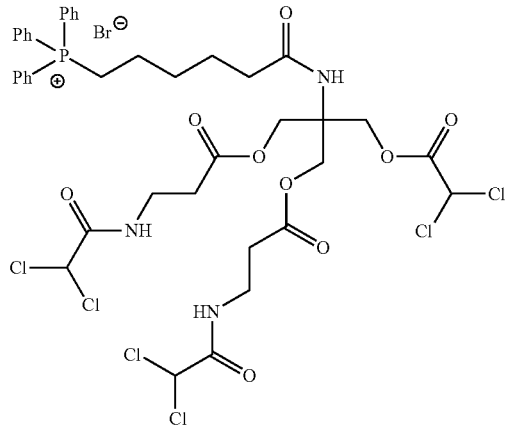

Mito(AD-AD-D)
Formula IX: TPP- Tris conjugated to two
β-alanino-DCA and one DCA iv. TPP-bis-ADCA In some embodiments, the targeted inhibitor is TPP-bis-ADCA. In this example, the targeting moiety is triphenylphosphonium (TPP), the modulator is alanyl-DCA, and for each TPP, there are two modulators.

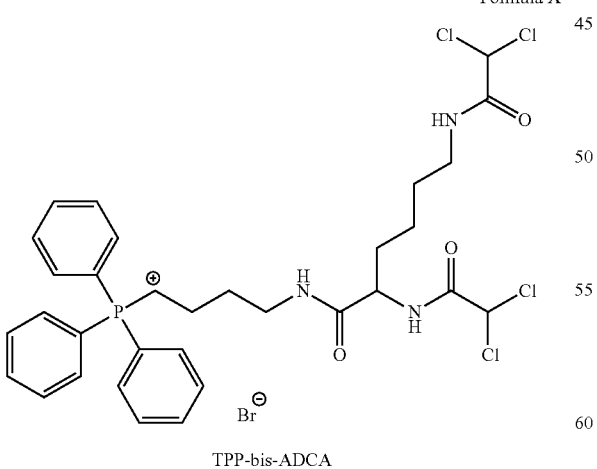

TPP-bis-ADCA v. TPP-ib-DCA

In other embodiments, the targeted inhibitor is TPP-ib-DCA. In this example, the targeting moiety is triphenylphosphonium (TPP), the modulator is DCA.

Formula XI

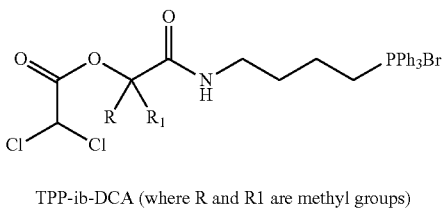

TPP-ib-DCA (where R and R1 are methyl groups)

vi. TPP-DCAPh

In other embodiments, the targeted inhibitor is TPP-DCAPh. In this example, the targeting moiety is triphenylphosphonium (TPP), and the modulator is DCA, which is first modified by conjugation to a phenol ring prior to its covalent attachment to TPP. A synthesis scheme is shown below.

Scheme I. A synthesis route of TPP-DCAPh

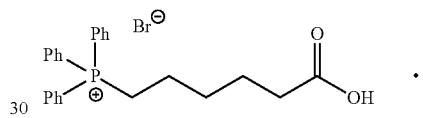

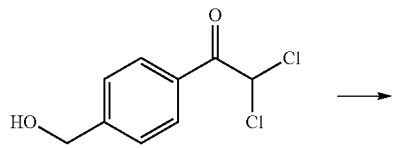

TPP-DCAPh vii. Mito-DCAPh

In other embodiments, the targeted inhibitor is Mito-DCAPh. Each Mito-DCAPh has three DCA moieties per molecule. A synthesis scheme is shown below.

Scheme II. A synthesis route of Mito-DCAPh

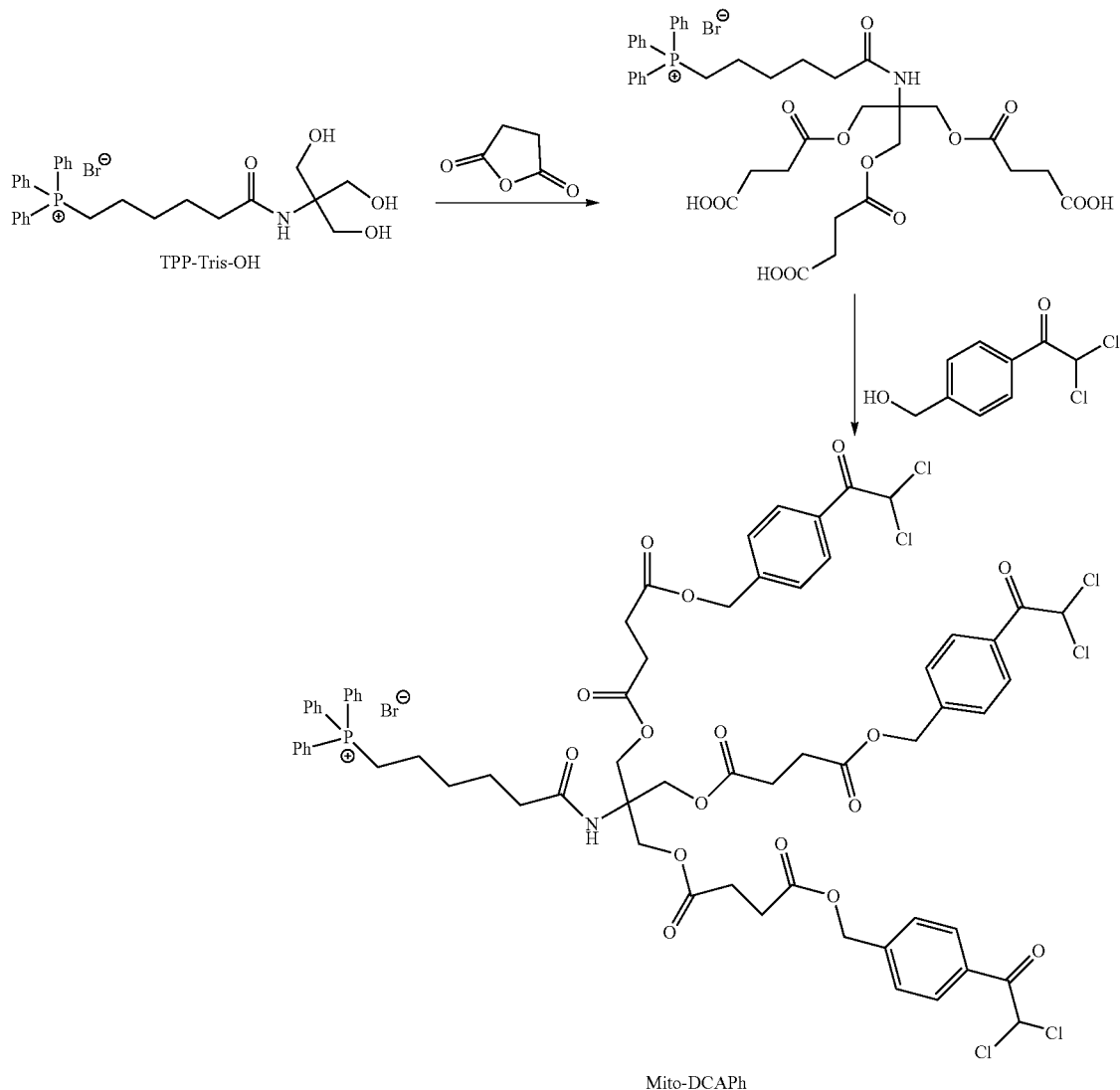

Mito-DCAPh viii. TPP-AZD7545

In other embodiments, the targeted inhibitor is TPP-AZD7545. In this example, the targeting moiety is triphenylphosphonium (TPP), and the modulator is AZD7545. A synthesis route is shown below.

Scheme III. A synthesis route of TPP-AZD7545

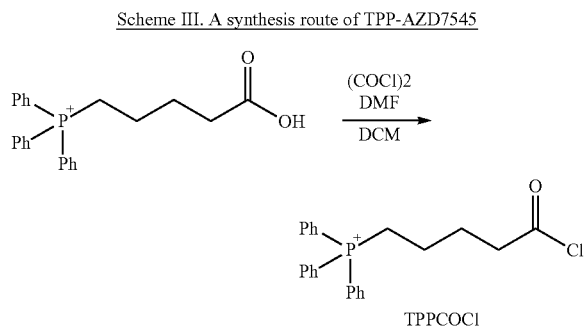

TPPCOCl

-continued

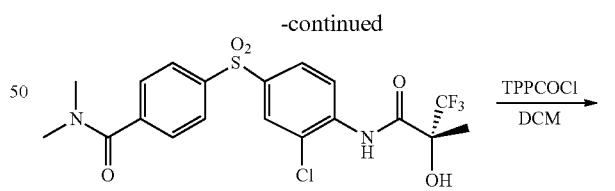

4. Linking Chemical Moiety

The compounds can contain a linking chemical moiety that serves to connect, directly or indirectly, one or more modulators to the hydrophobic portion of the compounds. The linking chemical moiety can be any organic, inorganic, or organometallic moiety which is polyvalent, so as to provide more than two points of attachment. The linking chemical moiety can be an organic molecule that contains multiple functional groups, or an organic moiety such as a substituted alkyl, unsubstituted alkyl, substituted alkylene, unsubstituted alkylene, substituted alkenyl, unsubstituted alkenyl, substituted alkynyl, unsubstituted alkynyl, substituted aryl, unsubstituted aryl, substituted cycloalkyl, unsubstituted cycloalkyl, substituted heteroalkyl, unsubstituted heteroalkyl, substituted heteroaryl, unsubstituted heteroaryl, substituted heterocyclyl, unsubstituted heterocyclyl, substituted arylalkyl, or unsubstituted arylalkyl.

The functional groups can be any atom or group of atoms that contains at least one atom that is neither carbon nor hydrogen, with the proviso that the groups must be capable of reacting with a nucleophile or an electrophile. Suitable functional groups include halogens (bromine, chlorine, and iodine); oxygen-containing functional groups such as a hydroxyls, epoxides, carbonyls, aldehydes, ester, carboxyls, and acid chlorides; nitrogen-containing functional groups such as amines and azides; and sulfur-containing groups such as thiols. The functional group may also be a hydrocarbon moiety which contains one or more non-aromatic pi-bonds, such as an alkyne, alkene, or diene. The linking chemical moiety can contain at least two different types of functional groups (e.g., one or more amines and one or more hydroxyls, one or more hydroxyls and one or more carboxyls, or one or more halides and one or more hydroxyls). In such cases, the different functional groups present on the linking chemical moiety can be independently addressed synthetically, permitting the covalent attachment of the rest of the compound and the one or more modulators in controlled stoichiometric ratios.

Following reaction of segments of the hydrophobic portion of the compounds and the modulator (directly or indirectly) with functional groups on the linking chemical moiety, the one or more hydrophobic portions and the one or more modulators will be covalently joined to the linking chemical moiety via bonds. The identity of these bonds will be determined by the identity of the functional group on the linking chemical moiety, the reactive loci of the hydrophobic portion or the rest of the compound and that of the functional group that attaches the modulator (directly or indirectly) to the linking chemical moiety. Examples of suitable bonds that connect the portions of the compound to the linking chemical moiety include —C(O)NH—, —C(O)NR'—, —NR'C(O)—, —C(O)O—, —OC(O)—, —C(O)OCH$_2$—, —SO$_2$NR'—, —CH$_2$R'—, —O—, —NR'H—, —NR'—, —OCONH—, —OCOO—, —NHCOO—, —OCONR'—, —NRCOO—, —NHCONH—, —NR'CONH—, —NHCONR'—, —NR'CONR'—, —CHOH—, —CROH—, unsubstituted alkyl (such as unsubstituted C$_1$-C$_{12}$ alkyl), substituted alkyl (such as substituted C$_1$-C$_{12}$ alkyl), wherein R' is hydrogen, halogen (F, Cl, Br, I), hydroxyl, unsubstituted alkyl (such as unsubstituted C$_1$-C$_{12}$ alkyl), substituted alkyl (such as substituted C$_1$-C$_{12}$ alkyl), substituted alkylene (such as substituted C$_1$-C$_{12}$ alkylene), unsubstituted alkylene (such as unsubstituted C$_1$-C$_{12}$ alkylene), an aryl group, or a heterocyclic group. Exemplary linking chemical moieties include the following organic compounds:

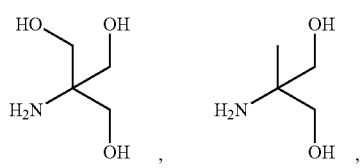

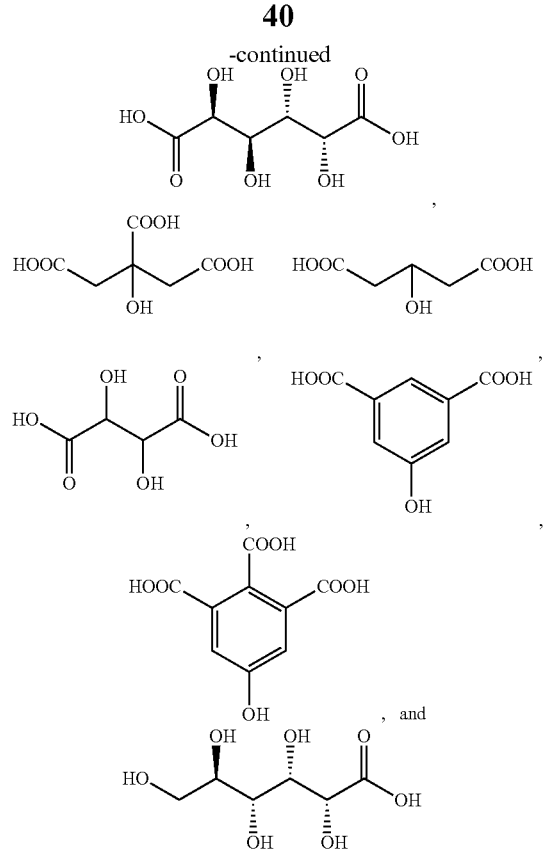

5. Modifications for Enhanced Encapsulation into Nanoparticles

In one aspect, the chemical linkages and/or modifications to the TM, and/or M are engineered for enhanced rate of encapsulation into delivery vehicles such as nanoparticles.

Generally, the enhanced rate of encapsulation of M and/or TM into nanoparticles is not limited by a particular mode of incorporation. For example, M and/or TM can be either exposed at the surface of the nanoparticles, buried at/near the core of the nanoparticles, or combinations thereof. The enhanced rate of encapsulation can also be achieved through increased non-covalent association with the nanoparticles, such as hydrogen bonds, van der Waals' forces, electrostatic interactions etc.

In some embodiments, two or more modulators independently conjugated to substituted/unsubstituted alkyl group(s), are subsequently joined together via one or more hydrophobic moieties. In such case, Formula I applies, where TM is

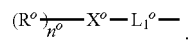

For example, IM$^o$ is metformin, and M is DCA. These two modulators, or their derivatives such as palmitoylated metformin, are conjugated via one or more L groups, such as L2-L3-L4-L5, and a W group. Any one or more of the L2-L3-L4-L5, and W can be hydrophobic groups. Without being limited to a certain theory, such molecular arrangement helps to enhance their incorporation into micelles, or nanoparticles such that the hydrophilic modulators e.g., metformin, and DCA, are located at, or close to the surface of the micelles, the alkyl groups, and the one more or hydrophobic moieties are at, or near the core of the micelles. Generally, this molecular design for enhanced incorporation into nanoparticles applies to any hydrophilic modulators, hydrophilic targeting moieties, or combinations thereof.

In some embodiments, two or more modulators independently conjugated to substituted/unsubstituted alkyl group(s), are subsequently joined together via one or more hydrophilic moieties. In such case, Formula I applies, where TM is

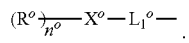

For example, IM° is BPTES, and M is pemetrexed. These two modulators, or their derivatives such as palmitoylated BPTES, are conugated via one or more L groups, such as L2-L3-L4-L5, and W. Any one or more of the L2-L3-L4-L5, and W are hydrophilic groups. Without being limited to a certain theory, such molecular arrangement helps to enhance their incorporation into micelles, or nanoparticles such that the hydrophilic moieties e.g., a phosphodiester linkage, are located at the surface of the micelles, the alkyl groups, and modulators e.g., BPTES, and pemetrexed, are at, or near the core of the micelles. Generally, this molecular design for enhanced incorporation into nanoparticles applies to any hydrophobic modulators, hydrophobic targeting moieties, or combinations thereof. In some further embodiments, these encapsulated, conjugated modulators are incorporated into the same micelle as those surface-exposed, conjugated modulators for desired targeting properties, and/or drug efficacy.

In some embodiments, the IM, IM°, TM is a positively, or negatively charged molecule to be incorporated into a delivery vehicle. In some embodiments, the IM, IM°, or TM is a hydrophobic, or hydrophilic molecule. In some embodiments, the M or TM is a positively charged molecule, either hydrophobic or hydrophilic, at a physiological pH; and IM° conjugated directly, or indirectly to the M is either positively, or negatively charged, either hydrophobic or hydrophilic, or combinations thereof.

In some embodiments, the increase in the length of alkyl chain increases the hydrophobicity of the composition, and enhances the rate of encapsulation into nanoparticles. For example, the increase in hydrophobicity increases the rate of encapsulation into the nanoparticle by 5%, 10%, 20%, 30%, 40%, 50%, 60%, 70%, 80%, 90%, or more than 90% compared to those without such modifications.

i. PalmtrisDCA or PDCA

In some embodiments, the composition is DCA conjugated to palmitic acid via tris(hydroxymethyl)aminomethane (Tris) group. PDCA, as a hydrophobic derivative of DCA, offers various advantages. Each PDCA has three DCA moieties per molecule and a long hydrophobic tail for better encapsulation and high loading into nanoparticles.

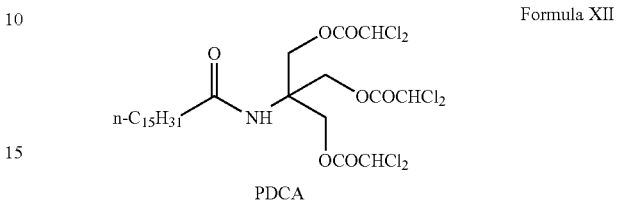

Formula XII

PDCA ii. PalmtrisalaninoDCA or PADCA

In some embodiments, palmitoyl group is introduced via an amide linkage and multiple alanyl-DCA were incorporated via tris(hydroxymethyl)aminomethane (Tris) using ester bonds. Similar to PDCA, each PADCA has three DCA moieties per molecule and a long hydrophobic tail for better encapsulation and high loading into nanoparticles.

Formula XIII

PADCA iii. Octyl 3-bromopyruvate & Tetradecyl 3-bromopyruvate

In some embodiments, the composition is octyl 3-bromopyruvate, where an octyl group is incorporated via an ester linkage to 3-bromo-2-oxopropanoate.

In some embodiments, the composition is tetradecyl 3-bromopyruvate, where a tetradecyl group is incorporated via an ester linkage to 3-bromo-2-oxopropanoate.

Formula XIV

Alkyl 3-bromopyruvate where R=$C_7H_{15}$ in octyl 3-bromopyruvate; R=$C_{13}H_{27}$ for tetradecyl 3-bromopyruvate.

iv. Palmtrisethoxyethanol (PTEE)

In some embodiments, palmitoyl group is introduced via an amide linkage and multiple ethoxy ethanol were incorporated via tris(hydroxymethyl)aminomethane (Tris) using ester bonds.

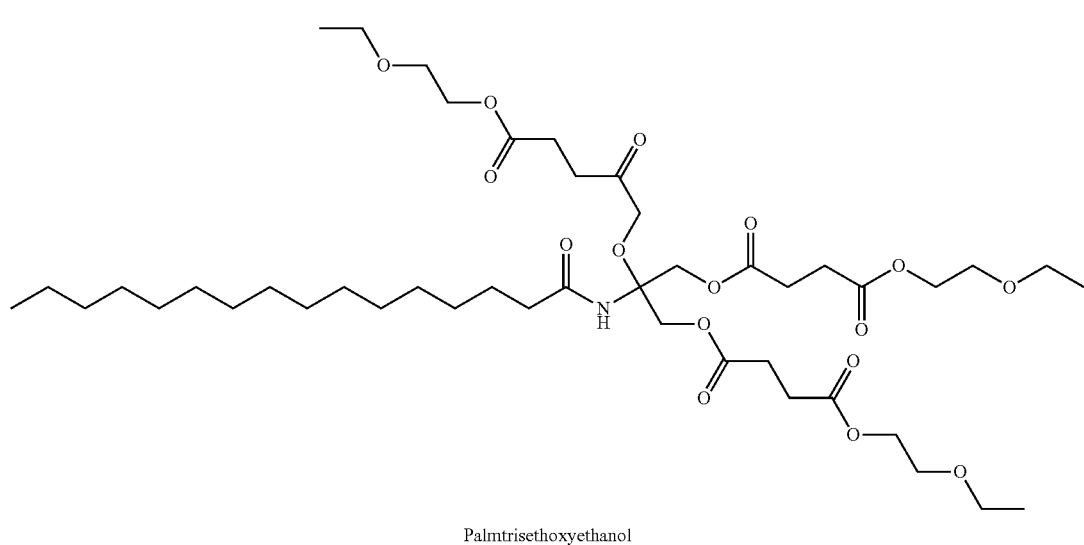

Palmtrisethoxyethanol

Formula XV v. Palmityl Geldanamycin (C16-Geld)

In some embodiments, the composition is geldanamycin conjugated with a palmityl side chain.

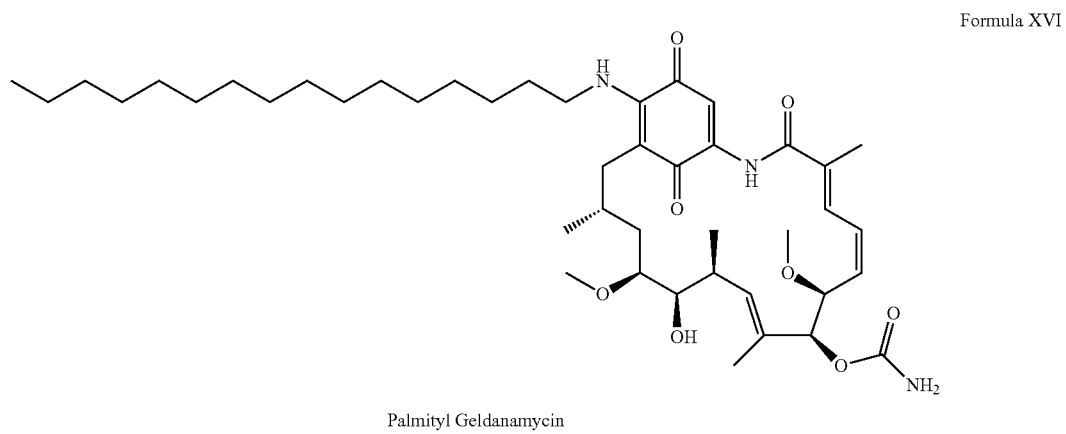 [SMILES: CCCCCCCCCCCCCCCCNC1=C2C[C@@H](C)C[C@H](OC)[C@H](O)[C@@H](C)/C=C(\C)[C@H](OC(N)=O)[C@@H](OC)/C=C\C=C(/C)C(=O)NC(=CC1=O)C2=O]

Palmityl Geldanamycin

Formula XVI vi. PalmbisLonidamine (PBLND)

In some embodiments, the composition is two lonidamine conjugated to a palmitoyl group by amide linkage via 2-amino-2-methyl-propan-1,3-diol.

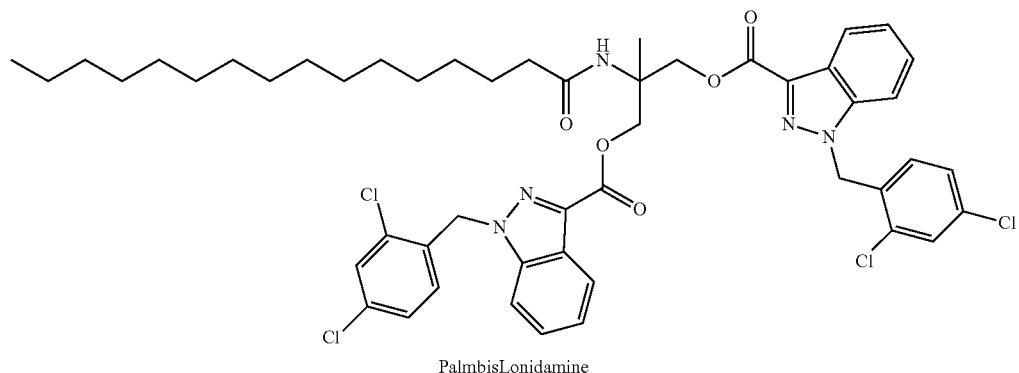

Formula XVII

PalmbisLonidamine vii. OctylLonidamine & EthylLonidaine

In some embodiments, the composition is lonidamine conjugated with an alkyl group such as octyl, and ethyl.

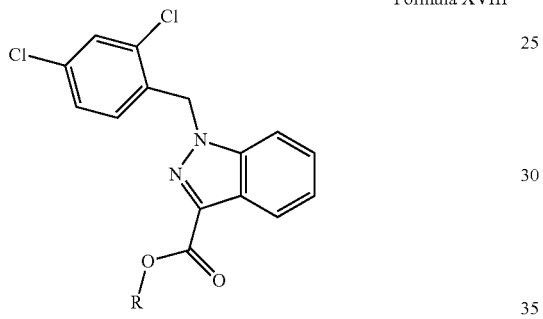

Formula XVIII

Alkyl Lonidamine viii. PalmMetformin (PalmMet)

In some embodiments, the composition metformin conjugated to a palmityl group.

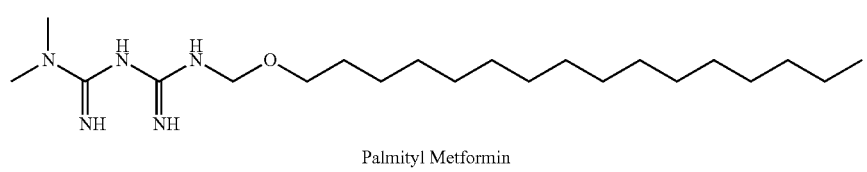

Formula XIX

Palmityl Metformin ix. Octyl Oxamate (OctOxamate)

In some embodiments, the composition is oxamate conjugated with an alkyl group such as octyl.

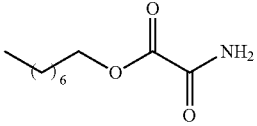

Formula XX

Octyl Oxamate x. Tetradecyl-cyanohydroxycinnamic acid (Td-CHC)

In some embodiments, the composition is cyanohydroxycinnamic acid conjugated with a long chain alkyl group such as tetradecyl.

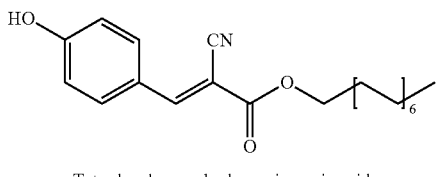

Formula XXI

Tetradecyl-cyanohydroxycinnamic acid xi. Palm-Tris-DCAPh

In some embodiments, the composition is DCA conjugated to palmitic acid via a phenol group. Each Palm-Tris-DCAPh has three DCA moieties per molecule and a long hydrophobic tail for better encapsulation and high loading into nanoparticles.

Scheme IV. A synthesis route of Palm-Tris-DCAPh

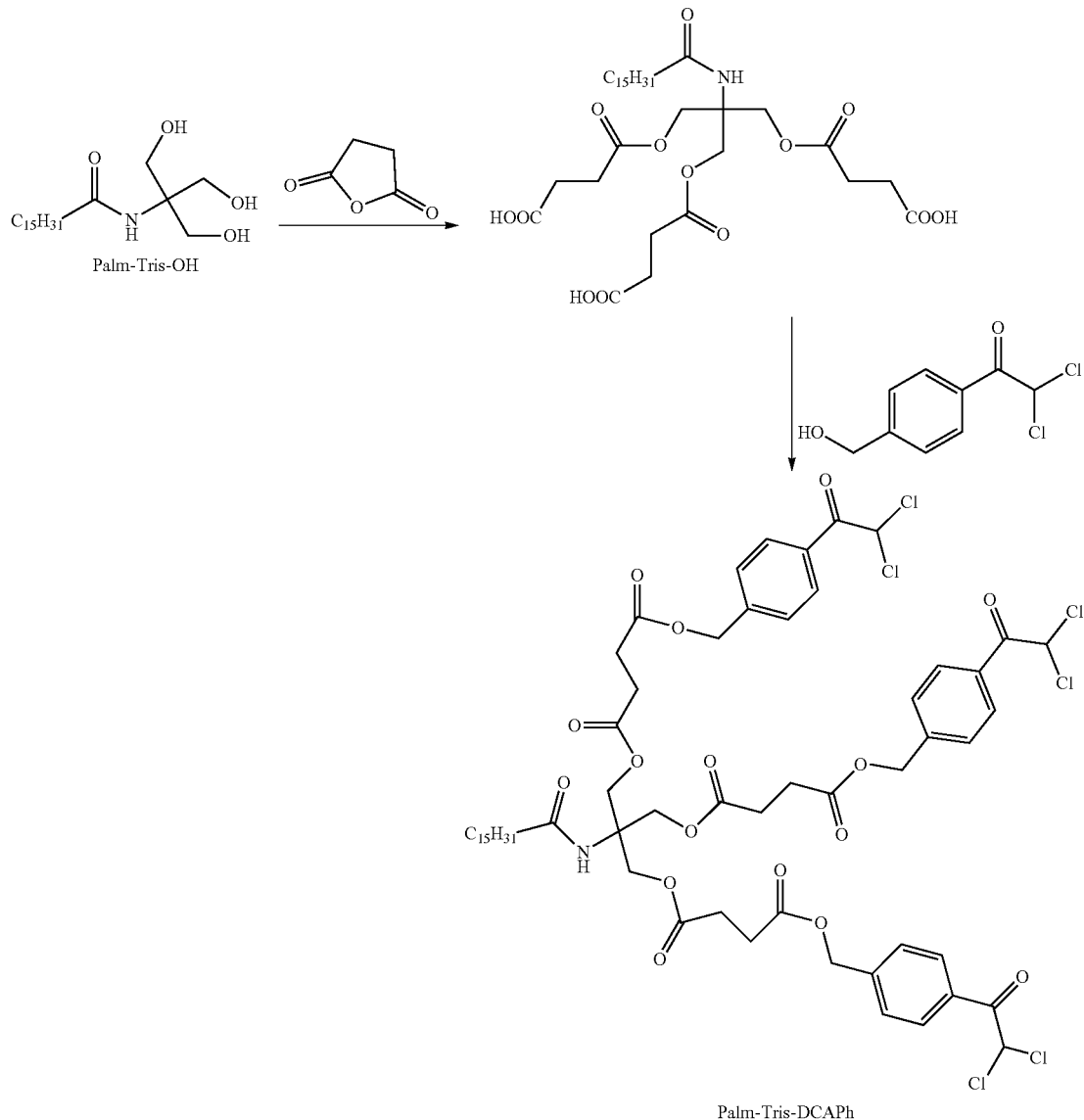

xii. Tetradecyl-CTP inhibitor

In some embodiments, the composition is 4-chloro-3-[[(3-nitrophenyl)amino]sulfonyl] benzoic acid conjugated with a long chain alkyl group such as tetradecyl. A synthesis route is shown below.

Scheme V. A synthesis route of tetradecyl 4-chloro-3-[[(3-nitrophenyl) amino]sulfonyl] benzoic acid

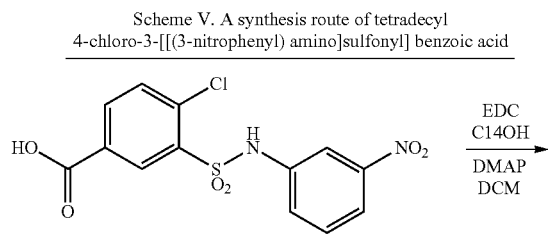

-continued

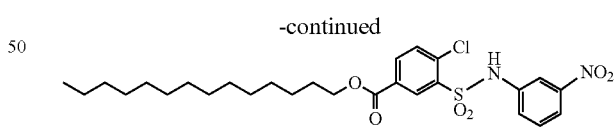

B. Additional Moieties

The modulator itself, or nanoparticles or another vehicle carrying the modulator can be associated with, linked, conjugated, or otherwise attached directly or indirectly to one or more additional moieties. The moiety can be a further targeting moiety, a detectable label, or a therapeutic, prophylactic, or diagnostic agent. For example, a polymer conjugate can be a PLGA-PEG-phosphonate.

C. Imaging Agents

The compositions can be incorporated into nanoparticles along with a detectable label, such as a radioisotope, a fluorophore (e.g., fluorescein isothiocyanate (FITC), phycoerythrin (PE)), an enzyme (e.g., alkaline phosphatase, horseradish peroxidase), element particles (e.g., gold particles) or a contrast agent. These may be encapsulated within, the nanoparticles carrying the modulators and/or targeting moieties.

For example, a fluorescent label can be chemically conjugated to a polymer of the nanoparticle to yield a fluorescently labeled polymer. In other embodiments the label is a contrast agent. A contrast agent refers to a substance used to enhance the contrast of structures or fluids within the body in medical imaging. Contrast agents are known in the art and include, but are not limited to, agents that work based on X-ray attenuation and magnetic resonance signal enhancement. Suitable contrast agents include iodine and barium.

In some embodiments, the targeting moiety is the imaging agent, for example Rhodamine 123.

D. Dendrimeric Compounds

Dendrimers offer precise architecture, high loading capacity, tunable solubility, and bioconjugation capability. The compounds disclosed herein can comprise dendrimers or hyperbranched polymers with multiple targeting moieties and modulators. The combination of the unique properties of dendrimers and hyperbranched polymers with the targeting moieties and modulators can lead to a more efficient-synthesis of compounds possessing high efficiency, for example, for bulk production.

Suitable dendrimers scaffolds that can be used herein include poly(amidoamine), also known as PAMAM, or STARBURST™ dendrimers; polypropylamine (POPAM), polyethylenimine, polylysine, polyester, iptycene, aliphatic poly(ether), and/or aromatic polyether dendrimers. Each dendrimer of the dendrimer complex may be same or of similar or different chemical nature than the other dendrimers (e.g., the first dendrimer may include a PAMAM dendrimer, while the second dendrimer may be a POPAM dendrimer). In some embodiments, the first or second dendrimer may further include an additional agent such as a multiarm PEG polymer including a polyethylene glycol having at least two branches bearing sulfhydryl or thiopyridine terminal groups. Other PEG polymers bearing other terminal groups such as succinimidyl or maleimide terminations can be used. The PEG polymers in the molecular weight 10 kDa to 80 kDa can be used. Complexes can be formed of one or more dendrimers.

The manufacturing process for these dendrimers is a series of repetitive steps starting with a central initiator core (e.g., ethylenediamine-cores). Each subsequent growth step represents a new "generation" of polymer with a larger molecular diameter, twice the number of reactive surface sites, and approximately double the molecular weight of the preceding generation. Dendrimeric scaffolds suitable for use herein are commercially available in a variety of generations. Preferable, the disclosed dendrimeric compounds herein are based generation 0, 1, 2, 3, 4, 5, 6, 7, 8, 9, or 10 dendrimeric scaffolds. Such scaffolds have, respectively, 4, 8, 16, 32, 64, 128, 256, 512, 1024, 2048, and 4096 reactive sites. Thus, the disclosed dendrimeric compounds based on these scaffolds have the corresponding number of combined targeting moieties and modulators.

Polyether amines are also suitable and contain primary amino groups attached to the terminus of a polyether backbone. The polyether backbone is typically based either on propylene oxide (PO), ethylene oxide (EO), or mixed EO/PO/BO. In one aspect, the polyether amine can be a polyoxyalkyleneamines. Such polyether amines can be obtained commercially from Huntsman Performance Products (Salt Lake City, Utah) under the name JEFF AMINE™ (e.g, JEFFAMINE D230). JEFF AMINES can have mono-amines, diamines, and triamines, and are available in a variety of molecular weights, ranging up to 5,000. Further examples of suitable dendrimers are based on 2,2-bis(hydroxymethyl)propionic acid (MPA). These hyperbranched polymers are commercially available in 2, 3, or 4, generations, which respectively have 16, 32, and 64 reactive sites for linking the disclosed TM and M moieties.

Still further, suitable dendrimers can be prepared by combining two or more dendrons. Dendrons are wedge-shaped sections of dendrimers with reactive focal point functional groups. Many dendron scaffolds are commercially available. They come in 1, 2, 3, 4, 5, and 6th generations with, respectively, 2, 4, 8, 16, 32, and 64 reactive groups. In certain examples, TM moieties are linked to one type of dendron and the inhibitor moieties are linked to another type of dendron. The two dendrons are then connected to form a dendrimer. A specific example of these compounds is shown below where a 2nd generation MPA dendron with 4 reactive sites was coupled to triphenylphosphinyl containing TM moieties. A separate 5th generation MPA dendron, with 32 reactive sites, was coupled to DCA. The two dendrons were then linked via click chemistry (i.e., a 1,3-dipolar cycloaddition reaction between an azide moiety on one dendron and alkyne moiety on another to form a triazole linker.

Exemplary preferred dendrimers are discussed in Published Application No. PCT/US2014/045131, which is specifically incorporated by reference herein in its entirety.

E. Nanoparticles

Generally, nanoparticles can be used to deliver the compounds to any targeted site, e.g. specific cell types, specific organelles. Mitochondria targeted polymeric nanoparticles are being used for delivery of the compounds to mitochondria and different parts within mitochondria. Exemplary preferred embodiments include, but are not limited to, mitochondrial-targeting nanoparticle containing dichloroacetate, mitochondrial-targeting nanoparticle containing lonidamine, mitochondrial targeting nanoparticle containing 3-bromopyruvate, mitochondrial-targeting nanoparticle containing galloflavin or oxalate, mitochondrial-targeting nanoparticle containing metformin, mitochondrial-targeting nanoparticle containing geldanamycin, mitochondrial-targeting nanoparticle containing cyanohydroxycinnamic acid.

Appropriate delivery vehicles for the compounds are known in the art and can be selected to suit the particular active agent. For example, in some embodiments, the composition is incorporated into or encapsulated by, or bound to, a nanoparticle, microparticle, microsphere, micelle, synthetic lipoprotein particle, or carbon nanotube. For example, the compositions can be incorporated into a vehicle such as polymeric microparticles or polymer nanoparticles which provide controlled release of the active agent(s). In some embodiments, release of the drug(s) is controlled by diffusion of the active agent(s) out of the microparticles and/or degradation of the polymeric particles by hydrolysis and/or enzymatic degradation.

In some embodiments, two modulators, with or without targeting moieties, are incorporated into the same particles and are formulated for release at different times and/or over different time periods. For example, in some embodiments, one of the agents is released entirely from the particles before release of the second agent begins. In other embodiments, release of the first agent begins followed by release of the second agent before the all of the first agent is released. In still other embodiments, both agents are released at the same time over the same period of time or over different periods of time.

1. Particle Core

The particle core can be a polymeric particle, a lipid particle, a solid lipid particle, an inorganic particle, or combinations thereof. For example, the particle core can be a lipid-stabilized polymeric particle. In preferred embodiments the particle core is a polymeric particle, a solid lipid particle, or a lipid-stabilized polymeric particle, preferably a polymeric particle.

The particle or nanoparticle core may have any diameter. The particle core can have a diameter of between about 10 nm and about 10 microns, inclusive, between about 10 nm and about 1 micron, inclusive, between about 10 nm and about 500 nm, inclusive, between about 20 nm and about 500 nm, inclusive, or between about 25 nm and about 250 nm, inclusive. In preferred embodiments the particle core is a nanoparticle core having a diameter between about 25 nm and about 250 nm, inclusive. In the most preferred embodiment the particles have a diameter between 10 nm and 150 nm, inclusive.

The particle or nanoparticle can have a zeta potential between −100 mV and +100 mV, inclusive, between −50 mV and +50 mV, inclusive, between −40 mV and +40 mV, inclusive, between −30 mV and +30 mV, inclusive, between −20 mV and +20 mV, inclusive, between −10 mV and +10 mV, inclusive, or between −5 mV and +5 mV, inclusive. The particle or nanoparticle can have a negative zeta potential. The particle can have a positive zeta potential. In some embodiments the particle has a substantially neutral zeta potential, i.e. the zeta potential is approximately 0 mV. In some embodiments the particle has a zeta potential of approximately between −20 mV and +20 mV, inclusive, more preferably between −10 mV and +10 mV, inclusive. In some embodiments, the zeta potential is between 0 and +100, inclusive, e.g., between 0 mV and +40 mV, inclusive, to enhance mitochondrial targeting.

Polymeric Particle Core

The particle core can be a polymeric particle core. The polymeric particle core can be formed from biodegradable polymers, non-biodegradable polymers, or a combination thereof. The polymeric particle core can be a biodegradable polymeric core in whole or in part.

Biodegradable polymers can include polymers that are insoluble or sparingly soluble in water that are converted chemically or enzymatically in the body into water-soluble materials. Biodegradable polymers can include soluble polymers crosslinked by hydolyzable cross-linking groups to render the crosslinked polymer insoluble or sparingly soluble in water. Representative biodegradable polymers include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly (isobutylmethacrylate), poly(hexlmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof. Exemplary biodegradable polymers include polyesters, poly(ortho esters), poly(ethylene imines), poly(caprolactones), poly(hydroxybutyrates), poly(hydroxyvalerates), polyanhydrides, poly(acrylic acids), polyglycolides, poly(urethanes), polycarbonates, polyphosphate esters, polyphosphazenes, derivatives thereof, linear and branched copolymers and block copolymers thereof, and blends thereof. Non-biodegradable polymers can include ethylene vinyl acetate, poly(meth) acrylic acid, polyamides, copolymers and mixtures thereof.

Excipients may also be added to the core polymer to alter its porosity, permeability, and or degradation profile.

The polymeric core can contain one or more hydrophilic polymers. Hydrophilic polymers include cellulosic polymers such as starch and polysaccharides; hydrophilic polypeptides; poly(amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly(hydroxyalkylmethacrylamide); poly(hydroxyalkylmethacrylate); poly(saccharides); poly (hydroxy acids); poly(vinyl alcohol), and copolymers thereof.

Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly (dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly (maleic acids), as well as copolymers thereof.

In certain embodiments, the hydrophobic polymer is an aliphatic polyester. In preferred embodiments, the polymeric core contains biodegradable polyesters such as poly(lactic acid), poly(glycolic acid), and poly(lactic-co-glycolic acid) or polyanhydrides.

The molecular weight of the hydrophobic polymer can be varied to tailor the properties of polymeric particle core. For example, the molecular weight of the hydrophobic polymer segment can be varied to engineer nanoparticles possessing the required average particle size and degradation profile. The hydrophobic polymer segment has a molecular weight of between about 150 Da and about 100 kDa, more preferably between about 1 kDa and about 75 kDa, most preferably between about 5 kDa and about 50 kDa.

The polymeric particle core can contain an amphiphilic polymer. Amphiphilic polymers can include block copolymers of any of the hydrophobic and hydrophilic polymers described above. In some embodiments the amphiphilic polymer is a copolymer containing a hydrophobic polyhydroxyacid block and a hydrophilic polyalkylene glycol block. The amphiphilic polymer can be a PLGA-PEG block copolymer, and PGA-PEG block copolymer, or a PLGA-PEG block copolymer.

PEGylation may also be used, in some cases, to decrease charge interaction between a polymer and a biological moiety, e.g., by creating a hydrophilic layer on the surface of the polymer, which may shield the polymer from interacting with the biological moiety. In some cases, the addition of poly(ethylene glycol) repeat units may increase plasma half-life of the polymer (e.g., copolymer, e.g., block copolymer), for instance, by decreasing the uptake of the polymer by the phagocytic system while decreasing transfection/uptake efficiency by cells. Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, or by ring opening polymerization techniques (ROMP).

Copolymers containing poly(ester-ether)s, e.g., polymers having repeat units joined by ester bonds (e.g., R—C(O)—O—R' bonds) and ether bonds (e.g., R—O—R' bonds) may be formed as a hydrolyzable polymer, containing carboxylic acid groups, conjugated with poly(ethylene glycol) repeat units to form a poly(ester-ether).

The polymeric particle core can contain any of the above polymers or blends or copolymers thereof. The polymeric particle core can contain one, two, three, or more different polymers.

Amphiphilic compounds include, but are not limited to, phospholipids, such as 1,2 distearoyl-sn-glycero-3-phosphoethanolamine (DSPE), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), and dilignoceroylphatidylcholine (DLPC), incorporated at a ratio of between 0.01-60 (weight lipid/w polymer), most preferably between 0.1-30 (weight lipid/w polymer). Phospholipids which may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcho-line (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophos-phoethanolamine. Synthetic phospholipids with asymmetric acyl chains (e.g., with one acyl chain of 6 carbons and another acyl chain of 12 carbons) may also be used.

The amphiphilic lipid can have a molecular weight of 200 to 1000, e.g., 700-900. By containing a relatively small amount of lipid, the nanoparticles avoid the negative impact that a tri, tetra or higher layer of lipid could have on a nanoparticle, such as an adverse effect on drug release. Thus, in one embodiment, the nanoparticles comprise approximately 10% to 40% lipid (by weight), and will have a size of about 90 nm to about 40 nm in diameter.

In a particular embodiment, an amphiphilic component that can be used to form an amphiphilic layer is lecithin, and, in particular, phosphatidylcholine. Lecithin forms a phospholipid bilayer having the hydrophilic (polar) heads facing aqueous solutions, and the hydrophobic tails facing each other. Lecithin has an advantage of being a natural lipid that is available from, e.g., soybean, and already has FDA approval for use in other delivery devices.

The particle core can be a lipid particle core. In some embodiments the particle core is a lipid nanoparticle. Lipid particles and lipid nanoparticles are known in the art. The lipid particles and lipid nanoparticles can be lipid micelles, liposomes, or solid lipid particles. The lipid particle can be made from one or a mixture of different lipids. Lipid particles are formed from one or more lipids, which can be neutral, anionic, or cationic at physiologic pH. The lipid particle is preferably made from one or more biocompatible lipids. The lipid particles may be formed from a combination of more than one lipid, for example, a charged lipid may be combined with a lipid that is non-ionic or uncharged at physiological pH.

The particle core can be a lipid micelle. Lipid micelles for drug delivery are known in the art. Lipid micelles can be formed, for instance, as a water-in-oil emulsion with a lipid surfactant. An emulsion is a blend of two immiscible phases wherein a surfactant is added to stabilize the dispersed droplets. In some embodiments the lipid micelle is a microemulsion. A microemulsion is a thermodynamically stable system composed of at least water, oil and a lipid surfactant producing a transparent and thermodynamically stable system whose droplet size is less than 1 micron, from about 10 nm to about 500 nm, or from about 10 nm to about 250 nm. Lipid micelles are generally useful for encapsulating hydrophobic active agents, including hydrophobic therapeutic agents, hydrophobic prophylactic agents, or hydrophobic diagnostic agents.

The particle core can be a liposome. Liposomes are small vesicles composed of an aqueous medium surrounded by lipids arranged in spherical bilayers. Liposomes can be classified as small unilamellar vesicles, large unilamellar vesicles, or multi-lamellar vesicles. Multi-lamellar liposomes contain multiple concentric lipid bilayers. Liposomes can be used to encapsulate targeted agents, by trapping hydrophilic agents in the aqueous interior or between bilayers, or by trapping hydrophobic agents within the bilayer.

The lipid micelles and liposomes typically have an aqueous center. The aqueous center can contain water or a mixture of water and alcohol. Suitable alcohols include, but are not limited to, methanol, ethanol, propanol, (such as isopropanol), butanol (such as n-butanol, isobutanol, sec-butanol, tert-butanol, pentanol (such as amyl alcohol, isobutyl carbinol), hexanol (such as 1-hexanol, 2-hexanol, 3-hexanol), heptanol (such as 1-heptanol, 2-heptanol, 3-heptanol and 4-heptanol) or octanol (such as 1-octanol) or a combination thereof.

The particle core can be a solid lipid particle. Solid lipid particles present an alternative to the colloidal micelles and liposomes. Solid lipid particles are typically submicron in size, i.e. from about 10 nm to about 1 micron, from 10 nm to about 500 nm, or from 10 nm to about 250 nm. Solid lipid particles are formed of lipids that are solids at room temperature. They are derived from oil-in-water emulsions, by replacing the liquid oil by a solid lipid.

Suitable neutral and anionic lipids include, but are not limited to, sterols and lipids such as cholesterol, phospholipids, lysolipids, lysophospholipids, sphingolipids or pegylated lipids. Neutral and anionic lipids include, but are not limited to, phosphatidylcholine (PC) (such as egg PC, soy PC), including 1,2-diacyl-glycero-3-phosphocholines; phosphatidylserine (PS), phosphatidylglycerol, phosphatidylinositol (PI); glycolipids; sphingophospholipids such as sphingomyelin and sphingoglycolipids (also known as 1-ceramidyl glucosides) such as ceramide galactopyranoside, gangliosides and cerebrosides; fatty acids, sterols, containing a carboxylic acid group for example, cholesterol; 1,2-diacyl-sn-glycero-3-phosphoethanolamine, including, but not limited to, 1,2-dioleylphosphoethanolamine (DOPE), 1,2-dihexadecylphosphoethanolamine (DHPE), 1,2-distearoylphosphatidylcholine (DSPC), 1,2-dipalmitoyl phosphatidylcholine (DPPC), and 1,2-dimyristoylphosphatidylcholine (DMPC). The lipids can also include various natural (e.g., tissue derived L-α-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of the lipids.

Suitable cationic lipids include, but are not limited to, N-[1-(2,3-dioleoyloxy)propyl]-N,N,N-trimethyl ammonium salts, also references as TAP lipids, for example methylsulfate salt. Suitable TAP lipids include, but are not limited to, DOTAP (dioleoyl-), DMTAP (dimyristoyl-), DPTAP (dipalmitoyl-), and DSTAP (distearoyl-). Suitable cationic lipids in the liposomes include, but are not limited to, dimethyldioctadecyl ammonium bromide (DDAB), 1,2-diacyloxy-3-trimethylammonium propanes, N-[1-(2,3-dioloyloxy)propyl]-N,N-dimethyl amine (DODAP), 1,2-diacyloxy-3-dimethylammonium propanes, N-[1-(2,3-dioleyloxy)propyl]-N,N,N-trimethylammonium chloride (DOTMA), 1,2-dialkyloxy-3-dimethylammonium propanes, dioctadecylamidoglycylspermine (DOGS), 3[N—(N',N'-dimethylamino-ethane)carbamoyl]cholesterol (DC-Chol); 2,3-dioleoyloxy-N-(2-(sperminecarboxamido)-ethyl)-N,N-dimethyl-1-propanaminium trifluoro-acetate (DOSPA), β-alanyl cholesterol, cetyl trimethyl ammonium bromide (CTAB), diC$_{14}$-amidine, N-ferf-butyl-N'-tetradecyl-3-tetradecylamino-propionamidine, N-(alpha-trimethylammonioacetyl)didodecyl-D-glutamate chloride (TMAG), ditetradecanoyl-N-(trimethyl-ammonio-acetyl)diethanolamine chloride, 1,3-dioleoyloxy-2-(6-carboxy-spermyl)-propylamide (DOSPER), and N, N, N', N'-tetramethyl-, N'-bis(2-hydroxylethyl)-2,3-dioleoyloxy-1,4-butanediammonium iodide. In one embodiment, the cationic lipids can be 1-[2-(acyloxy)ethyl]2-alkyl(alkenyl)-3-(2-hydroxyethyl)-imidazolinium chloride derivatives, for example, 1-[2-(9(Z)-octadecenoyloxy)ethyl]-2-(8(Z)-heptadecenyl-3-(2-hydroxyethyl)imidazolinium chloride (DOTIM), and 1-[2-(hexadecanoyloxy)ethyl]-2-pentadecyl-3-(2-hydroxyethyl)imidazolinium chloride (DPTIM). In one embodiment, the cationic lipids can be 2,3-dialkyloxypropyl quaternary ammonium compound derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimetyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

Suitable solid lipids include, but are not limited to, higher saturated alcohols, higher fatty acids, sphingolipids, synthetic esters, and mono-, di-, and triglycerides of higher saturated fatty acids. Solid lipids can include aliphatic alcohols having 10-40, preferably 12-30 carbon atoms, such as cetostearyl alcohol. Solid lipids can include higher fatty acids of 10-40, preferably 12-30 carbon atoms, such as stearic acid, palmitic acid, decanoic acid, and behenic acid. Solid lipids can include glycerides, including monoglycerides, diglycerides, and triglycerides, of higher saturated fatty acids having 10-40, preferably 12-30 carbon atoms, such as glyceryl monostearate, glycerol behenate, glycerol palmitostearate, glycerol trilaurate, tricaprin, trilaurin, trimyristin, tripalmitin, tristearin, and hydrogenated castor oil. Suitable solid lipids can include cetyl palmitate or beeswax. Cyclodextrin can also be used.

The particle core can be an inorganic particle such as metal or semiconductor particles. The particle core can be a metal nanoparticle, a semiconductor nanoparticle, or a core-shell nanoparticle. Inorganic particles and inorganic nanoparticles can be formulated into a variety of shapes such as rods, shells, spheres, and cones. The inorganic particle may have any dimension. The inorganic particle can have a greatest dimension less than 1 micron, from about 10 nm to about 1 micron, from about 10 nm to about 500 nm, or from 10 nm to about 250 nm.

The inorganic particle core can contain a metal. Suitable metals can include alkali metals such as lithium, sodium, potassium, rubidium, cesium and francium; alkaline earth metals such as beryllium, magnesium, calcium, strontium, barium and radium; transition metals such as zinc, molybdenum, cadmium, scandium, titanium, vanadium, chromium, manganese, iron, cobalt, nickel, copper, yttrium, zirconium, niobium, technetium, ruthenium, rhodium, palladium, silver, tungsten, iridium, and platinum; post-transition metals such as aluminum, gallium, indium, tin, thallium, lead, and bismuth; lanthanoids such as lanthanum, cerium, neodymium, and europium; and actinoids such as actinium, thorium, protactinium, uranium, *neptunium*, and plutonium. The metal can be biodegradable or non-biodegradable. Biodegradable metals can include alloys of iron or magnesium with the above metals, including alloys of magnesium, aluminum, and zinc.

The inorganic particle core can contain a metal oxide. Metal oxides of any of the above metals are contemplated. Suitable metal oxides can include metal oxides that contain one or more of the following metals: titanium, scandium, iron, tantalum, cobalt, chromium, manganese, platinum, iridium, niobium, vanadium, zirconium, tungsten, rhodium, ruthenium, copper, zinc, yttrium, molybdenum, technetium, palladium, cadmium, hafnium, rhenium and combinations thereof. Suitable metal oxides can include cerium oxides, platinum oxides, yttrium oxides, tantalum oxides, titanium oxides, zinc oxides, iron oxides, magnesium oxides, aluminum oxides, iridium oxides, niobium oxides, zirconium oxides, tungsten oxides, rhodium oxides, ruthenium oxides, alumina, zirconia, silicone oxides such as silica based glasses and silicon dioxide, or combinations thereof. The metal oxide can be non-biodegradable. The metal oxide can be a biodegradable metal oxide. Biodegradable metal oxides can include silicon oxide, aluminum oxide and zinc oxide.

The particle core can be a hybrid particle. Hybrid particle, as used herein, refers to a particle that combines the features of two or more of polymeric particles, lipid particles, and inorganic particles. Examples of hybrid particles can include polymer-stabilized liposomes, polymer-coated inorganic particles, or lipid-coated polymeric particles. The hybrid particle can contain a polymeric inner region, a lipid inner region, or an inorganic inner region. The hybrid particle can contain a polymer outer layer, a lipid outer layer, or an inorganic outer layer.

The particle core can be a polymer-stabilized lipid particle. The particle core can be a polymer-stabilized liposome. Polymer-stabilized liposomes are described, for example, in WO 2008/082721 by Dominguez et al. The particle core can be a polymer-stabilized solid lipid particle. Solid lipid particles have been coated with polymers to impart stability (see Nahire et al., *Biomacromolecules*, 14:841-853 (2013)) or to impart stealth properties (see Uner and Yener, *Int. J. Nanomedicine*, 2:289-300 (2007)). The polymer-stabilized liposomes and polymer-stabilized solid lipid particles include a lipid particle core stabilized by the presence of a coating polymer. The coating polymer can be covalently or non-covalently bound to the lipid particle. The coating polymer can be a lipophilic polymer, a biodegradable polymer, a polymer decreasing uptake by the RES, or a combination thereof.

The particle core can be a polymer-stabilized inorganic particle such as a polymer-coated metal nanoparticle. WO 2013/070653 by Alocilja et al. described metal nanoparticle stabilized by a polysaccharide coating polymer.

Suitable lipophilic polymers can include aliphatic polyesters, such as polylactic acid, polyglycolic acid and their copolymers; poly(ε-caprolactone), poly(6-valerolactone), polyesters with longer (i.e., Ci5 to C25) hydrocarbon chains; dendritic polymers of polyesters containing a modified terminal hydroxyl; aliphatic and aromatic polycarbonates; aliphatic polyamides, polypeptides; polyesteramides; polyurethanes; silicones, such as poly(dimethylsyloxanes); lipophilic poly(phosphazenes); poly(methacrylic acid), poly(styrene) and hydrophobic polyacrylic, polyvinyl and polystyrene carriers.

2. Particle Properties

Particles may be microparticles or nanoparticles. Nanoparticles are preferred for intertissue application, penetration of cells, and certain routes of administration. The nanoparticles may have any desired size for the intended use. The nanoparticles may have any diameter from about 10 nm to about 1,000 nm, inclusive. The nanoparticle can have a diameter from 10 nm to 900 nm, from 10 nm to 800 nm, from 10 nm to 700 nm, from 10 nm to 600 nm, from 10 nm to 500 nm, from 20 nm from 500 nm, from 30 nm to 500 nm, from 40 nm to 500 nm, from 50 nm to 500 nm, from 60 nm to 400 nm, from 50 nm to 350 nm, from 50 nm to 300 nm, or from 50 nm to 200 nm. In preferred embodiments the nanoparticles can have a diameter less than 400 nm, less than 300 nm, or less than 200 nm. The preferred range is between 50 nm and 300 nm, or 25 nm and 250 nm, or 80 nm and 150 nm.

One embodiment provides nanoparticles that are engineered to maximize half-life and targeting of the nanoparticles to tumor microenvironment, and/or tumor vasculature by adjusting the amount of PEG and the density of targeting moieties of the nanoparticles.

F. Kits

In some embodiments, the described compositions are provided in a kit. Typically, the described compositions are prepared using a pharmaceutically acceptable carrier composed of materials that are considered safe and effective and may be administered to an individual without causing undesirable biological side effects or unwanted interactions. A kit can include one or more of the compounds or compositions described. For example, a kit can include a compound of Mito-ADCA. A kit can further include one or more anti-cancer agents (e.g., paclitaxel). A kit can include an oral formulation of any of the compounds or compositions described. A kit can additionally include directions for use of the kit (e.g., instructions for treating a subject).

III. Methods of Making Particles

Methods for making the anti-cancer compositions for enhanced delivery to target sites are provided. The methods generally include polymer synthesis, nanoparticle preparation including encapsulation of the compositions.

In some embodiments, the compositions self assemble first due their hydrophobic groups, prior to their mixing with polymers in preparing for inhibitor-loaded nanoparticles.

A. Polymer Conjugates

Methods of polymer synthesis are described, for instance, in Braun et al. (2005) Polymer Synthesis: Theory and Practice. New York, N.Y.: Springer. The polymers may be synthesized via step-growth polymerization, chain-growth polymerization, or plasma polymerization. In most case they can be purchased from commercial sources.

In some embodiments an amphiphilic polymer is synthesized starting from a hydrophobic polymer terminated with a first reactive coupling group and a hydrophilic polymer terminated with a second reactive coupling group capable of reacting with the first reactive coupling group to form a covalent bond. One of either the first reactive coupling group or the second reactive coupling group can be a primary amine, where the other reactive coupling group can be an amine-reactive linking group such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. One of either the first reactive coupling group or the second reactive coupling group can be an aldehyde, where the other reactive coupling group can be an aldehyde reactive linking group such as hydrazides, alkoxyamines, and primary amines. One of either the first reactive coupling group or the second reactive coupling group can be a thiol, where the other reactive coupling group can be a sulfhydryl reactive group such as maleimides, haloacetyls, and pyridyl disulfides.

In preferred embodiments a hydrophobic polymer terminated with an amine or an amine-reactive linking group is coupled to a hydrophilic polymer terminated with complimentary reactive linking group. For example, an NHS ester activated PLGA can be formed by reacting PLGA-CO(OH) with NHS and a coupling reagent such as dicyclohexylcarbodiimide (DCC) or ethyl(dimethylaminopropyl) carbodiimide (EDC). The NHS ester activated PLGA can be reacted with a hydrophilic polymer terminated with a primary amine, such as a PEG-NH$_2$ to form an amphiphilic PLGA-b-PEG block copolymer.

In some embodiments, a conjugate of an amphiphilic polymer with a targeting moiety is formed using the same or similar coupling reactions. In some embodiments the conjugate is made starting from a hydrophilic polymer terminated on one end with a first reactive coupling group and terminated on a second end with a protective group. The hydrophilic polymer is reacted with a targeting moiety having a reactive group that is complimentary to the first reactive group to form a covalent bond between the hydrophilic polymer and the targeting moiety. The protective group can then be removed to provide a second reactive coupling group, for example to allow coupling of a hydrophobic polymer block to the conjugate of the hydrophilic polymer with the targeting moiety. A hydrophobic polymer terminated with a reactive coupling group complimentary to the second reactive coupling group can then be covalently coupled to form the conjugate. Of course, the steps could also be performed in reverse order, i.e. a conjugate of a hydrophobic polymer and a hydrophilic polymer could be formed first followed by deprotection and coupling of the targeting moiety to the hydrophilic polymer block.

In some embodiments, a conjugate is formed having a moiety conjugated to both ends of the amphiphilic polymer. For example, an amphiphilic polymer having a hydrophobic polymer block and a hydrophilic polymer block may have targeting moiety conjugated to the hydrophilic polymer block and an additional moiety conjugated to the hydrophobic polymer block. In some embodiments the additional moiety can be a detectable label. In some embodiments the additional moiety is a therapeutic, prophylactic, or diagnostic agent. For example, the additional moiety could be a moiety used for radiotherapy. The conjugate can be prepared starting from a hydrophobic polymer having on one end a first reactive coupling group and a another end first protective group and a hydrophilic polymer having on one end a second reactive coupling group and on another end a second protective group. The hydrophobic polymer can be reacted with the additional moiety having a reactive coupling group complimentary to the first reactive coupling group, thereby forming a conjugate of the hydrophobic polymer to the additional moiety. The hydrophilic polymer can be reacted with a targeting moiety having a reactive coupling group complimentary to the second reactive coupling group, thereby forming a conjugate of the hydrophilic polymer to the targeting moiety. The first protective group and the second protective group can be removed to yield a pair of complimentary reactive coupling groups that can be reacted to covalently link the hydrophobic polymer block to the hydrophilic polymer block.

B. Emulsion Methods

In some embodiments, a nanoparticle is prepared using an emulsion solvent evaporation method. For example, a polymeric material is dissolved in a water immiscible organic solvent and mixed with a drug solution or a combination of drug solutions. In some embodiments a solution of a therapeutic, prophylactic, or diagnostic agent to be encapsulated is mixed with the polymer solution. The polymer can be, but is not limited to, one or more of the following: PLA, PGA, PCL, their copolymers, polyacrylates, the aforementioned PEGylated polymers, the aforementioned Polymer-drug conjugates, the aforementioned polymer-peptide conjugates, or the aforementioned fluorescently labeled polymers, or various forms of their combinations. The drug molecules can be, but are not limited to, one or a more of the following: PPARgamma activators (e.g. Rosiglitazone, (RS)-5-[4-(2-[methyl(pyridin-2-yl)amino]ethoxy)benzyl]thiazolidine-2,4-dione, Pioglitazone, (RS)-5-(4-[2-(5-ethylpyridin-2-yl)ethoxy]benzyl)thiazolidine-2,4-dione, Troglitazone, (RS)-5-(4-[(6-hydroxy-2,5,7,8-tetramethylchroman-2-yl)methoxy]benzyl)thiazolidine-2,4-dione etc.), prostaglandin E2 analog (PGE2, (5Z,11α,13E,15S)-7-[3-hydroxy-2-(3-hydroxyoct-1-enyl)-5-oxo-cyclopentyl] hept-5-enoic acid etc.), beta3 adrenoceptor agonist (CL 316243, Disodium 5-[(2R)-2-[[(2R)-2-(3-Chlorophenyl)-2-hydroxyethyl]amino]propyl]-1,3-benzodioxole-2,2-dicarboxylate hydrate, etc.), Fibroblast Growth Factor 21 (FGF-21), Irisin, RNA, DNA, chemotherapeutic compounds, nuclear magnetic resonance (NMR) contrast agents, or combinations thereof. The water immiscible organic solvent, can be, but is not limited to, one or more of the following: chloroform, dichloromethane, and acyl acetate. The drug can be dissolved in, but is not limited to, one or more of the following: acetone, ethanol, methanol, isopropyl alcohol, acetonitrile and Dimethyl sulfoxide (DMSO).

In some embodiments the polymer solution contains one or more polymer conjugates as described above. The polymer solution can contain a first amphiphilic polymer conjugate having a hydrophobic polymer block, a hydrophilic polymer block, and a targeting moiety conjugated to the hydrophilic end. In preferred embodiments the polymer solution contains one or more additional polymers or amphiphilic polymer conjugates. For example the polymer solution may contain, in addition to the first amphiphilic polymer conjugate, one or more hydrophobic polymers, hydrophilic polymers, lipids, amphiphilic polymers, polymer-drug conjugates, or conjugates containing other targeting moieties. By controlling the ratio of the first amphiphilic polymer to the additional polymers or amphiphilic polymer conjugates, the density of the targeting moieties can be controlled. The first amphiphilic polymer may be present from 1% to 100% by weight of the polymers in the polymer solution. For example, the first amphiphilic polymer can be present at 10%, 20%, 30%, 40%, 50%, or 60% by weight of the polymers in the polymer solution.

An aqueous solution is then added into the resulting mixture solution to yield emulsion solution by emulsification. The emulsification technique can be, but not limited to, probe sonication or homogenization through a homogenizer. The plaque-targeted peptides or fluorophores or drugs may be associated with the surface of, encapsulated within, surrounded by, and/or distributed throughout the polymeric matrix of this inventive particle.

C. Nanoprecipitation Method

In another embodiment, a nanoparticle is prepared using nanoprecipitation methods or microfluidic devices. A polymeric material is mixed with a drug or drug combinations in a water miscible organic solvent. The polymer can be, but is not limited to, one or more of the following: PLA, PGA, PCL, their copolymers, polyacrylates, the aforementioned PEGylated polymers, the aforementioned Polymer-drug conjugates, the aforementioned polymer-peptide conjugates, or the aforementioned fluorescently labeled polymers, or various forms of their combinations. The drug molecules can be, but are not limited to, one or more of the following: PPARgamma activators (e.g. Rosiglitazone, (RS)-5-[4-(2-[methyl(pyridin-2-yl)amino]ethoxy)benzyl]thiazolidine-2,4-dione, Pioglitazone, (RS)-5-(4-[2-(5-ethylpyridin-2-yl)ethoxy]benzyl)thiazolidine-2,4-dione, Troglitazone, (RS)-5-(4-[(6-hydroxy-2,5,7,8-tetramethylchroman-2-yl)methoxy]benzyl)thiazolidine-2,4-dione etc.), prostaglandin E2 analog (PGE2, (5Z,11α,13E,15S)-7-[3-hydroxy-2-(3-hydroxyoct-1-enyl)-5-oxo-cyclopentyl] hept-5-enoic acid etc.), beta3 adrenoceptor agonist (CL 316243, Disodium 5-[(2R)-2-[[(2R)-2-(3-Chlorophenyl)-2-hydroxyethyl]amino]propyl]-1,3-benzodioxole-2,2-dicarboxylate hydrate, etc.), RNA, DNA, chemotherapeutic compounds, nuclear magnetic resonance (NMR) contrast agents, or combinations thereof. The water miscible organic solvent, can be, but is not limited to, one or more of the following: acetone, ethanol, methanol, isopropyl alcohol, acetonitrile and Dimethyl sulfoxide (DMSO). The resulting mixture solution is then added to a polymer non-solvent, such as an aqueous solution, to yield nanoparticle solution. The plaque-targeted peptides or fluorophores or drugs may be associated with the surface of, encapsulated within, surrounded by, and/or distributed throughout the polymeric matrix of this inventive particle.

D. Microfluidics

Methods of making nanoparticles using microfluidics are known in the art. Suitable methods include those described in U.S. Patent Application Publication No. 2010/0022680 A1 by Karnik et al. In general, the microfluidic device comprises at least two channels that converge into a mixing apparatus. The channels are typically formed by lithography, etching, embossing, or molding of a polymeric surface. A source of fluid is attached to each channel, and the application of pressure to the source causes the flow of the fluid in the channel. The pressure may be applied by a syringe, a pump, and/or gravity. The inlet streams of solutions with polymer, targeting moieties, lipids, drug, payload, etc. converge and mix, and the resulting mixture is combined with a polymer non-solvent solution to form the nanoparticles having the desired size and density of moieties on the surface. By varying the pressure and flow rate in the inlet channels and the nature and composition of the fluid sources nanoparticles can be produced having reproducible size and structure.

E. Other Methodologies

1. Solvent Evaporation

In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid microparticles. The resulting microparticles are washed with water and dried overnight in a lyophilizer. Microparticles with different sizes (0.5-1000 microns) and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

2. Hot Melt Microencapsulation

In this method, the polymer is first melted and then mixed with the solid particles. The mixture is suspended in a non-miscible solvent (like silicon oil), and, with continuous stirring, heated to 5□C above the melting point of the polymer. Once the emulsion is stabilized, it is cooled until the polymer particles solidify. The resulting microparticles are washed by decantation with petroleum ether to give a free-flowing powder. Microparticles with sizes between 0.5 to 1000 microns are obtained with this method. The external surfaces of spheres prepared with this technique are usually smooth and dense. This procedure is used to prepare microparticles made of polyesters and polyanhydrides. However, this method is limited to polymers with molecular weights between 1,000-50,000.

3. Solvent Removal

This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make microparticles from polymers with high melting points and different molecular weights. Microparticles that range between 1-300 microns can be obtained by this procedure. The external morphology of spheres produced with this technique is highly dependent on the type of polymer used.

4. Spray-Drying

In this method, the polymer is dissolved in organic solvent. A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration=0.04 g/mL, inlet temperature=−24° C., outlet temperature=13-15° C., aspirator setting=15, pump setting=10 mL/minute, spray flow=600 Nl/hr, and nozzle diameter=0.5 mm. Microparticles ranging between 1-10 microns are obtained with a morphology which depends on the type of polymer used.

5. Hydrogel Microparticles

Microparticles made of gel-type polymers, such as alginate, are produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The microparticles are left to incubate in the bath for twenty to thirty minutes in order to allow sufficient time for gelation to occur. Microparticle particle size is controlled by using various size extruders or varying either the nitrogen gas or polymer solution flow rates. Chitosan microparticles can be prepared by dissolving the polymer in acidic solution and crosslinking it with tripolyphosphate. Carboxymethyl cellulose (CMC) microparticles can be prepared by dissolving the polymer in acid solution and precipitating the microparticle with lead ions. In the case of negatively charged polymers (e.g., alginate, CMC), positively charged ligands (e.g., polylysine, polyethyleneimine) of different molecular weights can be ionically attached.

IV. Formulations

Formulations and pharmaceutical compositions containing an effective amount of the composition in a pharmaceutical carrier appropriate for administration to an individual in need thereof to treat one or more symptoms of cancer are provided. The formulations are designed for administration parenterally (e.g., by intramuscular, intraperitoneal, intravenous (IV) or subcutaneous injection or infusion). It may also be possible to administer topically (e.g., to a mucosal surface such as the mouth, lungs, intranasal, intravaginally, etc.). The compositions designed to be administered locally or systemically.

The compositions can be formulated for immediate release, extended release, or modified release. A delayed release dosage form is one that releases a drug (or drugs) at a time other than promptly after administration. An extended release dosage form is one that allows at least a twofold reduction in dosing frequency as compared to that drug presented as a conventional dosage form (e.g. as a solution or prompt drug-releasing, conventional solid dosage form). A modified release dosage form is one for which the drug release characteristics of time course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms.

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients.

Generally, pharmaceutically acceptable salts can be prepared by reaction of the free acid or base forms of an active agent with a stoichiometric amount of the appropriate base or acid in water or in an organic solvent, or in a mixture of the two; generally, non-aqueous media like ether, ethyl acetate, ethanol, isopropanol, or acetonitrile are preferred. Pharmaceutically acceptable salts include salts of an active agent derived from inorganic acids, organic acids, alkali metal salts, and alkaline earth metal salts as well as salts formed by reaction of the drug with a suitable organic ligand (e.g., quaternary ammonium salts). Lists of suitable salts are found, for example, in Remington's Pharmaceutical Sciences, 20th ed., Lippincott Williams & Wilkins, Baltimore, Md., 2000, p. 704.

In some embodiments, the targeted agent is incorporated into or encapsulated by a nanoparticle, microparticle, micelle, synthetic lipoprotein particle, or carbon nanotube. For example, the compositions can be incorporated into a vehicle such as polymeric microparticles which provide controlled release of the active agent. In some embodiments, release of the modulator is controlled by diffusion of the targeted agent out of the microparticles and/or degradation of the polymeric particles by hydrolysis and/or enzymatic degradation. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof.

The targeted agent can be incorporated into or prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, waxlike substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to, hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes.

Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

Parenteral Formulations

The composition, for example, a modulator of cancer cell metabolism having a cancer cell-targeting moiety associated with, linked, conjugated, or otherwise attached directly or indirectly to the modulator of cancer cell metabolism, or to a nanoparticle or other delivery vehicle thereof can be formulated for parenteral delivery, such as injection or infusion, in the form of a solution or suspension, or a powder. The formulation can be administered via any route, such as, the blood stream or directly to the organ or tissue to be treated. The particles may be provided in a lyophilized or dried form in a unit dosage form, for suspension at the time of injection. These may be provided in a kit with an appropriate amount of diluent such as sterile water or buffered solution.

Parenteral formulations can be prepared as aqueous compositions using techniques known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the compounds or nanoparticles can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s) or nanoparticles.

The formulation is typically buffered to a pH of between 3 and 8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the compound or nanoparticles in the required amount in the appropriate solvent or dispersion medium with one or more of the excipients listed above, as required, followed by filtered sterilization. Generally, dispersions are prepared by incorporating the various sterilized compositions into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the compound or nanoparticle plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration are preferably in the form of a sterile aqueous solution or suspension of particles formed from one or more polymer-drug conjugates. Acceptable solvents include, for example, water, Ringer's solution, phosphate buffered saline (PBS), and isotonic sodium chloride solution. The formulation may also be a sterile solution, suspension, or emulsion in a nontoxic, parenterally acceptable diluent or solvent such as 1,3-butanediol.

In some instances, the formulation is distributed or packaged in a liquid form. Alternatively, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for parenteral administration may also contain one or more tonicity agents to adjust the isotonic range of the formulation. Suitable tonicity agents are well known in the art. Examples include glycerin, mannitol, sorbitol, sodium chloride, and other electrolytes.

Solutions, suspensions, or emulsions for parenteral administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychioro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for parenteral administration may also contain one or more excipients known art, such as dispersing agents, wetting agents, and suspending agents.

V. Methods of Use

Methods of using the compositions to treat cancer are provided. Methods of using the compositions to treat other diseases, disorders and injury including neurodegenerative diseases such as Parkinson's Alzheimer's, Huntington's, etc.; inflammatory diseases, including, but not limited to ulcerative colitis, Crohn's disease, and rheumatoid arthritis, are also provided.

Methods of using the compositions to treat cancer are provided. The methods typically include administering a subject in a need thereof an effective amount of a composition including a targeted agent which contains a modulator of cancer metabolism.

In the most preferred embodiments, methods of using the compositions lead to (a) direct or indirect inhibition of glycolysis or oxidative phosphorylation or any other form of metabolism that utilizes glucose or equivalents from the disease area's microenvironment or direct or indirect inhibition of the uptake of glucose or equivalents from the disease area microenvironment, and/or (b) direct or indirect inhibition of the production of lactate or equivalents, or the direct or indirect inhibition of the release of lactate or equivalents into the disease microenvironment.

Modulating cancer metabolism can modify the tumor microenvironment amenable for an immune response against the cancer cells. In some embodiments, treatment using the compositions increases the number or activity of immune cells, for example, tumor associated immune cells, relative to the number or activity of the immune cells prior to administration of the targeted agent, or compared to administration of the targeted agent absent a targeting moiety, a delivery vehicle, or a combination thereof. The immune cells can include, but are not limited to, CD4 cells and CD8 cells. In some embodiments, the compositions increase the number of CD4 or CD8 cells in the tumor. In some embodiments, the increase in immune cells is an increase in the total number of immune cells. In some embodiments, the increase in immune cells is an increase in the ratio of immune cells to tumor cells. Accordingly, in some embodiments, the increase in immune cells is actually the results of a reduction in tumor cells. In some embodiments, treatment using the compositions leads to a decrease in expression of a regulator of immune suppression (or suppressor of immune activation) such as PD-1, CTLA4, or a combination thereof.

A. Treatment Regimen

A treatment regimen can include one or multiple administrations of the compositions for achieving a desired physiological change, including administering to an animal, such as a mammal, especially a human being, an effective amount of the compositions to treat the disease or symptom thereof, or to produce the physiological change.

1. Dosage and Effective Amounts

A therapeutically effective amounts of targeted agents used in the treatment of cancer are typically sufficient to reduce or alleviate one or more symptoms of cancer. Symptoms of cancer may be physical, such as tumor burden, or biological such as proliferation of cancer cells. Accordingly, the amount of modulator can be effective to, for example, kill tumor cells or inhibit proliferation or metastasis of the tumor cells. Preferably the modulator, for example via the targeting moiety, is preferentially delivered cancer cells. Preferably the modulator does not target or otherwise modulate the metabolism of non-cancer cells, particular immune cells such as tumor infiltrating lymphocytes, or does so at a reduced level compared to cancer (e.g. tumor) cells. In this way, by-products and other affects associated with aberrant metabolism in cancer cells are reduced, preferably leading directly or indirectly to cancer cell death. In some embodiments, the targeted agent reduces cancer cell migration, angiogenesis, immune escape, radioresistance, or a combination thereof. In some embodiments, the targeted agent induces a change in the cancer cell itself or its microenvironment that reduces suppression or induces activation of an immune response against the cancer cell. For example, in some embodiments, the composition is administered in an effective amount to enhance and/or prolonging the activation of T cells (i.e., increasing antigen-specific proliferation of T cells, enhance cytokine production by T cells, stimulate differentiation, stimulate effector functions of T cells and/or promote T cell survival) or overcome T cell exhaustion and/or anergy.

The actual effective amounts of modulator can vary according to factors including the specific modulator administered, the particular composition formulated, the mode of administration, and the age, weight, condition of the subject being treated, as well as the route of administration and the disease or disorder.

The therapeutic result of the targeted agents can be compared to a control. Suitable controls are known in the art. A typical control is a comparison of a condition or symptom of a subject prior to and after administration of the targeted agent. The condition or symptom can be a biochemical, molecular, physiological, or pathological readout. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or average determined based on measuring the symptom, pharmacologic, or physiologic indicator in one or more subjects that do not have the disease or condition to be treated (e.g., healthy subjects). In some embodiments, the effect of the treatment is compared to a conventional treatment that is known in the art, such as one of those discussed herein.

In some embodiments, the effective amount of targeted agents causes little or no killing of non-cancerous cells, and preferably little or no inhibition of metabolism in non-cancer cells. It is particularly preferred that the composition have little or no effect on immune cells such as TIL.

In some embodiments, dosages are administered once, twice, or three times daily, or every other day, two days, three days, four days, five days, or six days to a human. In some embodiments, dosages are administered about once or twice every week, every two weeks, every three weeks, or every four weeks. In some embodiments, dosages are administered about once or twice every month, every two months, every three months, every four months, every five months, or every six months.

In some embodiments, the regimen includes one or more cycles of a round of therapy followed by a drug holiday (e.g., no drug). The round of the therapy can be, for example, and of the administrations discussed above. Likewise, the drug holiday can be 1, 2, 3, 4, 5, 6, or 7 days; or 1, 2, 3, 4 weeks, or 1, 2, 3, 4, 5, or 6 months.

In particular embodiments, the subject is administered a dosage of between about 6 mg/kg and 18 mg/kg. Particular dosage regimens include, for example, one or more cycles in which the subject is administered the drug each of five days in a row, followed by a two-day drug holiday.

B. Combination Therapies and Procedures

The compositions can be administered alone or in combination with one or more conventional therapies, for example, a conventional cancer therapy. In some embodiments, the conventional therapy includes administration of one or more of the compositions in combination with one or more additional active agents. The combination therapies can include administration of the active agents together in the same admixture, or in separate admixtures. Therefore, in some embodiments, the pharmaceutical composition includes two, three, or more active agents. Such formulations typically include an effective amount of a modulator of cancer cell metabolism. The additional active agent(s) can have the same, or different mechanisms of action. In some embodiments, the combination results in an additive effect on the treatment of the cancer. In some embodiments, the combinations result in a more than additive effect on the treatment of the disease or disorder.

The additional therapy or procedure can be simultaneous or sequential with the combination therapy. In some embodiment the additional therapy is performed between drug cycles or during a drug holiday that is part of the compositions dosage regime. For example, in some embodiments, the additional therapy or procedure is surgery, a radiation therapy, or chemotherapy.

Additional therapeutic agents include conventional cancer therapeutics such as chemotherapeutic agents, cytokines, chemokines, and radiation therapy. The majority of chemotherapeutic drugs can be divided into: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and the tyrosine kinase inhibitors e.g., imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to, amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epipodophyllotoxins, epirubicin, etoposide, etoposide phosphate, fludarabine, fluorouracil, gemcitabine, hydroxycarb amide, idarubicin, ifosfamide, innotecan, leucovorin, liposomal doxorubicin, liposomal daunorubici, lomustine, mechlorethamine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, teniposide, tegafur-uracil, temozolomide, teniposide, thiotepa, tioguanine, topotecan, treosulfan, vinblastine, vincristine, vindesine, vinorelbine, taxol and derivatives thereof, trastuzumab (HERCEPTIN®), cetuximab, and rituximab (RITUXAN® or MABTHERA®), bevacizumab (AVASTIN®), and combinations thereof. Representative pro-apoptotic agents include, but are not limited to, fludarabinetaurosporine, cycloheximide, actinomycin D, lactosylceramide, 15d-PGJ(2)5 and combinations thereof.

In some embodiments, the compositions and methods are used prior to or in conjunction with an immunotherapy such inhibition of checkpoint proteins such as PD-1 or CTLA-4, adoptive T cell therapy, and/or a cancer vaccine. Methods of adoptive T cell therapy are known in the art and used in clinical practice. Generally adoptive T cell therapy involves the isolation and ex vivo expansion of tumor specific T cells to achieve greater number of T cells than what could be obtained by vaccination alone. The tumor specific T cells are then infused into patients with cancer in an attempt to give their immune system the ability to overwhelm remaining tumor via T cells, which can attack and kill the cancer. Several forms of adoptive T cell therapy can be used for cancer treatment including, but not limited to, culturing tumor infiltrating lymphocytes or TIL; isolating and expanding one particular T cell or clone; and using T cells that have been engineered to recognize and attack tumors. In some embodiments, the T cells are taken directly from the patient's blood. Methods of priming and activating T cells in vitro for adaptive T cell cancer therapy are known in the art. See, for example, Wang, et al, *Blood,* 109(11):4865-4872 (2007) and Hervas-Stubbs, et al, *J. Immunol.,* 189(7):3299-310 (2012).

Historically, adoptive T cell therapy strategies have largely focused on the infusion of tumor antigen specific cytotoxic T cells (CTL) which can directly kill tumor cells. However, CD4+ T helper (Th) cells such as Th1, Th2, Tfh, Treg, and Th17 can also be used. Th can activate antigen-specific effector cells and recruit cells of the innate immune system such as macrophages and dendritic cells to assist in antigen presentation (APC), and antigen primed Th cells can directly activate tumor antigen-specific CTL. As a result of activating APC, antigen specific $Th_1$ have been implicated as the initiators of epitope or determinant spreading which is a broadening of immunity to other antigens in the tumor. The ability to elicit epitope spreading broadens the immune response to many potential antigens in the tumor and can lead to more efficient tumor cell kill due to the ability to mount a heterogeneic response. In this way, adoptive T cell therapy can used to stimulate endogenous immunity.

In some embodiments, the T cells express a chimeric antigen receptor (CARs, CAR T cells, or CARTs). Artificial T cell receptors are engineered receptors, which graft a particular specificity onto an immune effector cell. Typically, these receptors are used to graft the specificity of a monoclonal antibody onto a T cell and can be engineered to target virtually any tumor associated antigen. First generation CARs typically had the intracellular domain from the CD3 ζ-chain, which is the primary transmitter of signals from endogenous TCRs. Second generation CARs add intracellular signaling domains from various costimulatory protein receptors (e.g., CD28, 41BB, ICOS) to the cytoplasmic tail of the CAR to provide additional signals to the T cell, and third generation CARs combine multiple signaling domains, such as CD3z-CD28-41BB or CD3z-CD28-OX40, to further enhance effectiveness.

In some embodiments, the compositions and methods are used prior to or in conjunction with a cancer vaccine, for example a dendritic cell cancer vaccine. Vaccination typically includes administering a subject an antigen (e.g., a cancer antigen) together with an adjuvant to elicit therapeutic T cells in vivo. In some embodiments, the cancer vaccine is a dendritic cell cancer vaccine in which the antigen delivered by dendritic cells primed ex vivo to present the cancer antigen. Examples include, for example, PROVENGE® (sipuleucel-T), which is a dendritic cell-based vaccine for the treatment of prostate cancer (Ledford, et al., *Nature,* 519, 17-18 (5 Mar. 2015). Such vaccines and other compositions and methods for immunotherapy are reviewed in Palucka, et al., *Nature Reviews Cancer,* 12, 265-277 (April 2012).

In some embodiments, the compositions and methods are used prior to or in conjunction with surgical removal of tumors, for example, in preventing primary tumor metastasis. In some embodiments, the compositions and methods are used to enhance body's own anti-tumor immune functions.

C. Subjects to be Treated

In general, the compositions and methods of treatment thereof are useful in the context of cancer, including tumor therapy. The compositions can also be used for treatment of other diseases, disorders and injury including neurodegenerative diseases such as Parkinson's Alzheimer's, Huntington's, etc.; inflammatory diseases, including, but not limited to ulcerative colitis, Crohn's disease, and rheumatoid arthritis.

In some embodiments, the subject to be treated is a human. All the methods described can include the step of identifying and selecting a subject in need of treatment, or a subject who would benefit from administration with the described compositions.

1. Proliferative Disorders

In some embodiments, the compositions and methods of treatment thereof are useful for treatment of abnormal cellular proliferation such as cancer or endometriosis.

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site.

The compositions and methods described herein are useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. The compositions are particularly effective in treating carcinomas. Sarcomas, which arise less frequently, are derived from mesodermal connective tissues such as bone, fat, and cartilage. The leukemias and lymphomas are malignant tumors of hematopoietic ceils of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, cancers such as vascular cancer such as multiple myeloma, adenocarcinomas and sarcomas, of bone, bladder, brain, breast, cervical, colorectal, esophageal, kidney, liver, lung, nasopharangeal, pancreatic, prostate, skin, stomach, and uterine. In some embodiments, the compositions are used to treat multiple cancer types concurrently. The compositions can also be used to treat metastases or tumors at multiple locations.

Exemplary tumor cells include, but are not limited to, tumor cells of cancers, including leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as, but not limited to, chronic myelocytic (granulocytic) leukemia, chronic lymphocytic leukemia, hairy cell leukemia; polycythemia vera; lymphomas such as, but not limited to, Hodgkin's disease, non-Hodgkin's disease; multiple myelomas such as, but not limited to, smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including, but not limited to, pheochromocytom and adrenocortical carcinoma; thyroid cancer such as but not limited to papillary or follicular thyroid cancer, medullary thyroid cancer and anaplastic thyroid cancer; pancreatic cancer, including, but not limited to, insulinoma, gastrinoma, glucagonoma, vipoma, somatostatin-secreting tumor, and carcinoid or islet cell tumor; pituitary cancers including, but not limited to, Cushing's disease, prolactin-secreting tumor, acromegaly, and diabetes insipius; eye cancers including, but not limited to, ocular melanoma such as iris melanoma, choroidal melanoma, and cilliary body melanoma, and retinoblastoma; vaginal cancers, including, but not limited to, squamous cell carcinoma, adenocarcinoma, and melanoma; vulvar cancer, including, but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepideimoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including, but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. Cancers that can be prevented, treated or otherwise diminished by the compositions include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, papillary adenocarcinomas, and gastric cancer (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In some embodiments, the cancers are characterized as being triple negative breast cancer, or having one or more KRAS-mutations, EGFR mutations, ALK mutations, RB1 mutations, HIF mutations, KEAP mutations, NRF mutations, or other metabolic-related mutations, or combinations thereof. The methods and compounds as described herein are useful for both prophylactic and therapeutic treatment.

Therapeutic treatment involves administering to a subject a therapeutically effective amount of the compositions or pharmaceutically acceptable salts thereof as described after cancer is diagnosed.

In further embodiments, the described compositions are used for prophylactic use i.e. prevention, delay in onset, diminution, eradication, or delay in exacerbation of signs or symptoms after onset, and prevention of relapse. For prophylactic use, a therapeutically effective amount of the compounds and compositions or pharmaceutically acceptable salts thereof as described are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms. Prophylactic administration can be used, for example, in the chemopreventative treatment of subjects presenting precancerous lesions, those diagnosed with early stage malignancies, and for subgroups with susceptibilities (e.g., family, racial, and/or occupational) to particular cancers.

2. Neurodegenerative Diseases

The compositions and methods can also be used to delivery active agents for the treatment of a neurological or neurodegenerative disease or disorder or central nervous system disorder. The methods typically include administering the subject an effective amount of the disclosed composition to increase cognition or reduce a decline in cognition, increase a cognitive function or reduce a decline in a cognitive function, increase memory or reduce a decline in memory, increase the ability or capacity to learn or reduce a decline in the ability or capacity to learn, or a combination thereof.

Neurodegeneration refers to the progressive loss of structure or function of neurons, including death of neurons. For example, the compositions and methods can be used to treat subjects with a disease or disorder, such as Parkinson's Disease (PD) and PD-related disorders, Huntington's Disease (HD), Amyotrophic Lateral Sclerosis (ALS), Alzheimer's Disease (AD) and other dementias, Prion Diseases such as Creutzfeldt-Jakob Disease, Corticobasal Degeneration, Frontotemporal Dementia, HIV-Related Cognitive Impairment, Mild Cognitive Impairment, Motor Neuron Diseases (MND), Spinocerebellar Ataxia (SCA), Spinal Muscular Atrophy (SMA), Friedreich's Ataxia, Lewy Body Disease, Alpers' Disease, Batten Disease, Cerebro-Oculo-Facio-Skeletal Syndrome, Corticobasal Degeneration, Gerstmann-Straussler-Scheinker Disease, Kuru, Leigh's Disease, Monomelic Amyotrophy, Multiple System Atrophy, Multiple System Atrophy With Orthostatic Hypotension (Shy-Drager Syndrome), Multiple Sclerosis (MS), Neurodegeneration with Brain Iron Accumulation, Opsoclonus Myoclonus, Posterior Cortical Atrophy, Primary Progressive Aphasia, Progressive Supranuclear Palsy, Vascular Dementia, Progressive Multifocal Leukoencephalopathy, Dementia with Lewy Bodies (DLB), Lacunar syndromes, Hydrocephalus, Wernicke-Korsakofr s syndrome, post-encephalitic dementia, cancer and chemotherapy-associated cognitive impairment and dementia, and depression-induced dementia and pseudodementia.

In some embodiments, the subject has a central nervous system disorder or is in need of neuroprotection. Exemplary conditions and/or subjects include, but are not limited to, subjects having had, subjects with, or subjects likely to develop or suffer from a stroke, a traumatic brain injury, a spinal cord injury, Post-Traumatic Stress syndrome, or a combination thereof.

In some embodiments, the compositions and methods are administered to a subject in need thereof in an effective amount to reduce, or prevent one or more molecular or clinical symptoms of a neurodegenerative disease, or one or more mechanisms that cause neurodegeneration. Neurodegeneration, and diseases and disorders thereof, can be caused by a genetic mutation or mutations; protein misfolding; intracellular mechanisms such as dysregulated protein degradation pathways, membrane damage, mitochondrial dysfunction, or defects in axonal transport; defects in programmed cell death mechanisms including apoptosis, autophagy, cytoplasmic cell death; and combinations thereof. More specific mechanisms common to neurodegenerative disorders include, for example, oxidative stress, mitochondrial dysfunction, excitotoxicity, inflammatory changes, iron accumulation, and/or protein aggregation.

Symptoms of neurodegenerative diseases are known in the art and vary from disease to disease. In some embodiments, the disease exhibits or is characterized by one or any combination of the following symptoms or diseases: stress, anxiety, seasonal depression, insomnia and tiredness, schizophrenia, panic attacks, melancholy, dysfunction in the regulation of appetite, insomnia, psychotic problems, epilepsy, senile dementia, various disorders resulting from normal or pathological aging, migraine, memory loss, disorders of cerebral circulation, cardiovascular pathologies, pathologies of the digestive system, fatigue due to appetite disorders, obesity, pain, psychotic disorders, diabetes, senile dementia, or sexual dysfunction. In some embodiments, the subject does not exhibit one or more of the preceding symptoms.

In some embodiments, the subject has been medically diagnosed as having a neurodegenerative disease or a condition in need of neuroprotection by exhibiting clinical (e.g., physical) symptoms of the disease. Therefore, in some embodiments, the compounds or compositions disclosed herein are administered prior to a clinical diagnosis of a disease or condition. In some embodiments, a genetic test indicates that the subject has one or more genetic mutations associated with a neurodegenerative disease or central nervous system disorder.

Neurodegenerative diseases are typically more common in aged individuals.

Active agents for the treatment of neurodegenerative diseases are well known in the art and can vary based on the symptoms and disease to be treated. For example, conventional treatment for Parkinson's disease can include levodopa (usually combined with a dopa decarboxylase inhibitor or COMT inhibitor), a dopamine agonist, or an MAO-B inhibitor.

Treatment for Huntington's disease can include a dopamine blocker to help reduce abnormal behaviors and movements, or a drug such as amantadine and tetrabenazine to control movement, etc. Other drugs that help to reduce chorea include neuroleptics and benzodiazepines. Compounds such as amantadine or remacemide have shown preliminary positive results. Hypokinesia and rigidity, especially in juvenile cases, can be treated with antiparkinsonian drugs, and myoclonic hyperkinesia can be treated with valproic acid. Psychiatric symptoms can be treated with medications similar to those used in the general population. Selective serotonin reuptake inhibitors and mirtazapine have been recommended for depression, while atypical antipsychotic drugs are recommended for psychosis and behavioral problems.

Riluzole (RILUTEK®) (2-amino-6-(trifluoromethoxy) benzothiazole), an antiexcitotoxin, has yielded improved survival time in subjects with ALS. Other medications, most used off-label, and interventions can reduce symptoms due to ALS. Some treatments improve quality of life and a few appear to extend life. Common ALS-related therapies are reviewed in Gordon, *Aging and Disease,* 4(5):295-310 (2013), see, e.g., Table 1 therein. A number of other agents have been tested in one or more clinical trials with efficacies ranging from non-efficacious to promising. Exemplary agents are reviewed in Carlesi, et al., *Archives Italiennes de Biologie,* 149:151-167 (2011). For example, therapies may include an agent that reduces excitotoxicity such as talampanel (8-methyl-7H-1,3-dioxolo(2,3)benzodiazepine), a cephalosporin such as ceftriaxone, or memantine; an agent that reduces oxidative stress such as coenzyme Q10, manganoporphyrins, KNS-760704 [(6R)-4,5,6,7-tetrahydro-N6-propyl-2,6-benzothiazole-diamine dihydrochloride, RPPX], or edaravone (3-methyl-1-phenyl-2-pyrazolin-5-one, MCI-186); an agent that reduces apoptosis such as histone deacetylase (HDAC) inhibitors including valproic acid, TCH346 (Dibenzo(b,f)oxepin-10-ylmethyl-methylprop-2-ynylamine), minocycline, or tauroursodeoxycholic Acid (TUDCA); an agent that reduces neuroinflammation such as thalidomide and celastol; a neurotropic agent such as insulin-like growth factor 1 (IGF-1) or vascular endothelial growth factor (VEGF); a heat shock protein inducer such as arimoclomol; or an autophagy inducer such as rapamycin or lithium.

Treatment for Alzheimer's Disease can include, for example, an acetylcholinesterase inhibitor such as tacrine, rivastigmine, galantamine or donepezil; an NMDA receptor antagonist such as memantine; or an antipsychotic drug.

Treatment for Dementia with Lewy Bodies can include, for example, acetylcholinesterase inhibitors such as tacrine, rivastigmine, galantamine or donepezil; the N-methyl d-aspartate receptor antagonist memantine; dopaminergic therapy, for example, levodopa or selegiline; antipsychotics such as olanzapine or clozapine; REM disorder therapies such as clonazepam, melatonin, or quetiapine; anti-depression and antianxiety therapies such as selective serotonin reuptake inhibitors (citalopram, escitalopram, sertraline, paroxetine, etc.) or serotonin and noradrenaline reuptake inhibitors (venlafaxine, mirtazapine, and bupropion) (see, e.g., Macijauskiene, et al., *Medicina* (*Kaunas*), 48(1):1-8 (2012)).

Exemplary neuroprotective agents are also known in the art in include, for example, glutamate antagonists, antioxidants, and NMDA receptor stimulants. Other neuroprotective agents and treatments include caspase inhibitors, trophic factors, anti-protein aggregation agents, therapeutic hypothermia, and erythropoietin.

Other common active agents for treating neurological dysfunction include amantadine and anticholinergics for treating motor symptoms, clozapine for treating psychosis, cholinesterase inhibitors for treating dementia, and modafinil for treating daytime sleepiness.

3. Autoimmune or Inflammatory Disease

In some embodiments, the compositions can also be used for treatment of autoimmune or inflammatory disease or disorder. Exemplary autoimmune or inflammatory disease or disorder include rheumatoid arthritis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Bechet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis-juvenile, discoid lupus, essential mixed cryoglobulinemia, fibromyalgia-fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

D. Controls

The effect of the described composition can be compared to a control. Suitable controls are known in the art and include, for example, an untreated subject, or a placebo-treated subject. In some embodiments, an untreated control subject suffers from, the same disease or condition as the treated subject e.g. colorectal cancer.

EXAMPLES

Example 1: Synthesis and Stability of β-Alanyl DCA (ADCA)

Synthesis from DCA

β-alanine (2 g, 22 mmol) and NaHCO$_3$ (4.6 g, 55 mmol) were suspended in water/THF mixture (2:1, 30 mL) and DCA chloride (2 mL, 24.2 mmol) in THF (20 mL) was added to the mixture dropwise at 0° C. The solution was stirred for 2 hr at RT, diluted to 100 mL with NaHCO$_3$ and washed with ether 3×50 mL. The aqueous layer was acidified with 1 M HCl to pH 2 and extracted with DCM 5×50 mL. The organic fraction was dried over MgSO$_4$ and concentrated. The residue was precipitated into hexanes, to give the product as white powder (99% pure, small amount of DCA as an impurity). Yield: 84 mg (2%). The synthesis route of β-alanyl DCA is shown below.

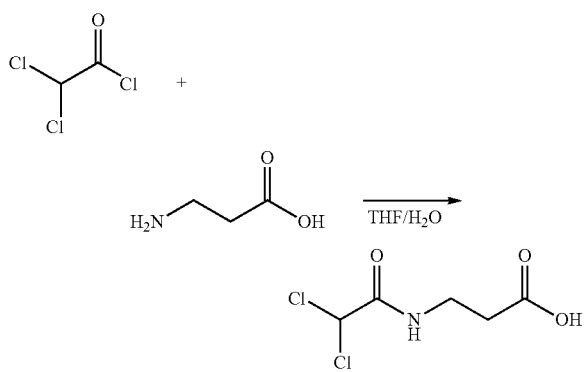

Scheme VI. A synthesis route of β-alanyl DCA

Synthesis from DCA Anhydride

ADCA can also be prepared using alternative method such as the following: β-alanine (2 g, 22 mmol) was suspended in DCM (30 mL) and DCA anhydride (4 mL, 26.4 mmol) was added to the mixture. The solution stirred for three days and the solvent was evaporated. The residue was triturated in ether/hexanes 1:2 (150 mL) and left at −20 for 1 h. The resulting precipitate was filtered off. The product was recrystallized two times using 1:1 ether/hexanes mixture. Yield 3.7 g, 84%, colorless crystals.

This synthesis route of β-alanyl DCA is shown below in Scheme VII.

Scheme VII. An alternative synthesis route of β-alanyl DCA

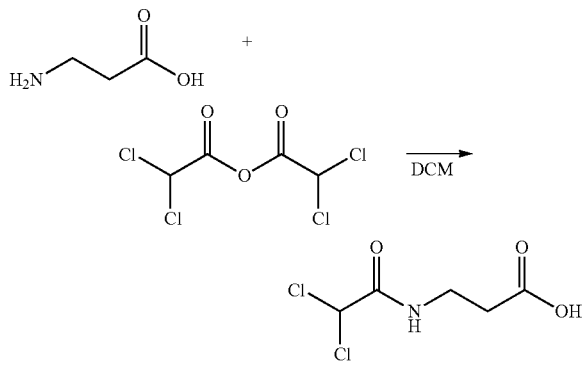

ADCA is Stable in Serum

Stability of ADCA in cell culture media containing 10% FBS was examined by looking at the HPLC chromatograms and area under the peaks. For the study, 1.5 mM solution of ADCA was prepared by mixing 10 μL of 100 mM DMSO stock solution with 1.99 mL of cell media. Turbidity was observed after mixing, however no precipitate was observed. The samples were then stored at 37° C., 150 μL aliquots were analyzed by HPLC (the sample was mixed before taking an aliquot, however no visible precipitate was observed even before mixing). Alanyl-DCA was detected at 205 nm with a retention time of 9.7 min on HPLC. The total area of absorbance peak indicated virtually no change in ADCA concentration over five days.

Example 2: Stability of TPP-Tris-β-alanino-DCA (Mito-ADCA)

Synthesis of TPP-Tris-β-alanino-DCA (Mito-ADCA)

MitoADCA was prepared in two steps. The synthesis route of TPP-Tris-β-alanino-DCA is shown below in Scheme VIII.

Scheme VIII. Synthesis route of TPP-Tris-β-alanino-DCA

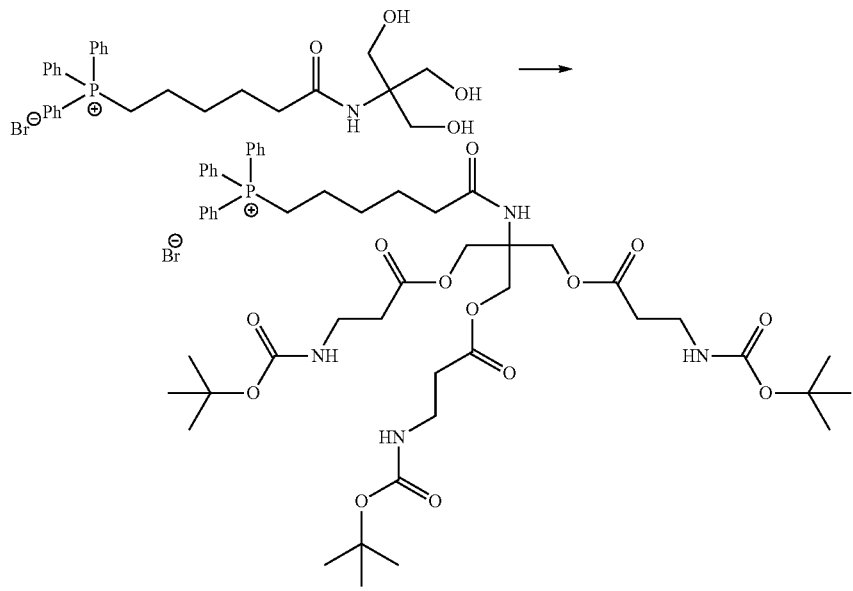

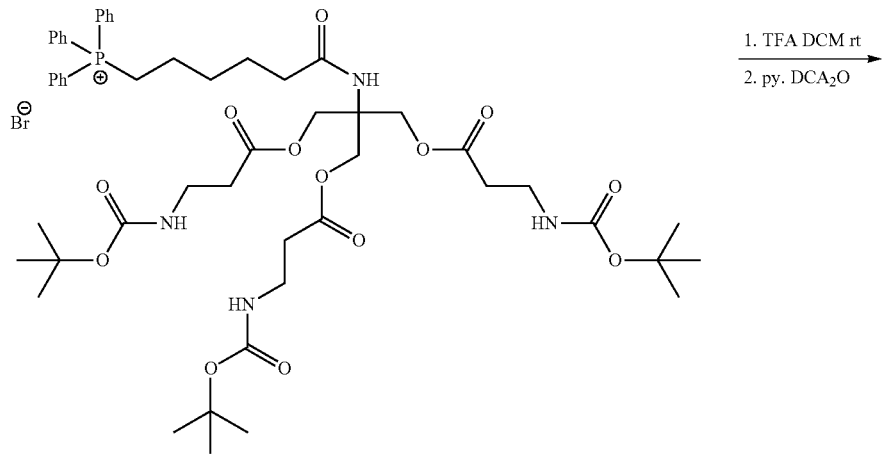

1. TFA DCM rt
2. py. DCA₂O

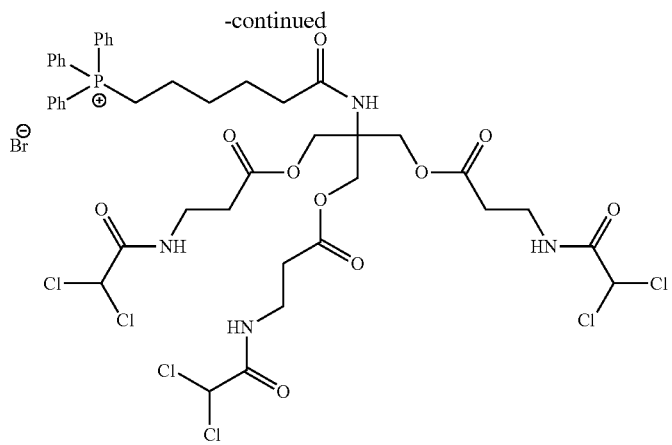

TPP-tris-OH was reacted with Boc protected beta-alanine using EDC, DMAP reagents in DMF solvent. DMF was removed and the product was purified by column chromatography.

To the solution of BOC protected compound in DCM, excess TFA was added, stirred 30 min to remove the BOC group. After concentration, this residue was dissolved in DCM, and Pyridine was added. To this mixture, DCA anhydride was added drop-wise, and the mixture was stirred for 30 min. The solution was washed with 0.1% $H_2SO_4$-Brine, and dried over $MgSO_4$. After concentration, the residue was purified by column chromatography. HPLC analysis of the resultant compound showed 2 peaks. From mass and NMR analysis it was concluded that the second product is a molecule similar to Mito-ADCA, where one of DCA was replaced with TFA. This exchange with TFA might have happened during the BOC deprotection. In further attempts, TFA was replaced by HO/dioxane to deprotect the BOC group and the product was pure from NMR and HPLC.

Stability of Mito-ADCA

Stability of Mito-ADCA in cell culture media containing 10% FBS was monitored by examining the HPLC chromatograms and area under the peaks. Scheme below expected degradation products:

Scheme IX. Degradation of Mito-ADCA

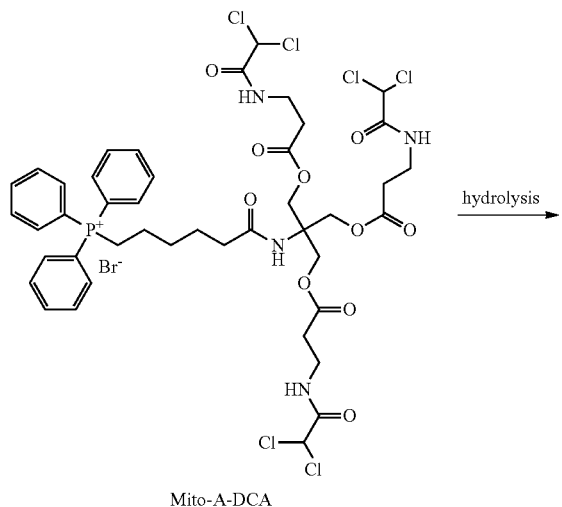

Mito-A-DCA

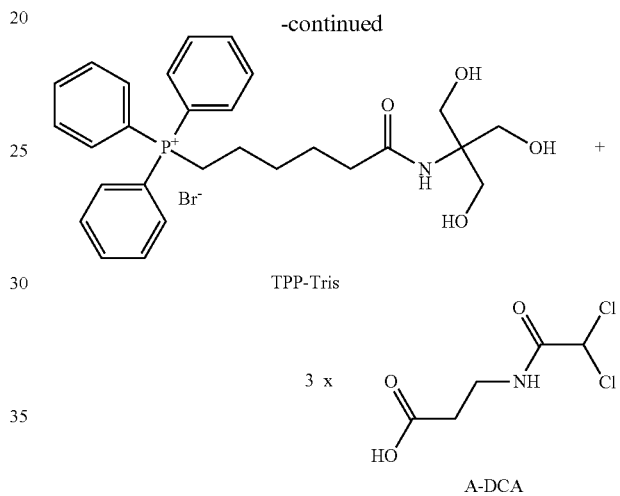

TPP-Tris

A-DCA

For this study, 500 μM solution of Mito-ADCA (MAD) was prepared by mixing 10 μL of 100 mM DMSO stock solution with 1.99 mL of cell culture media (RPMI 1640 medium, supplemented with 10% FBS, 1% Pen/strep). Turbidity was observed after mixing, however no precipitate was observed. The samples were then stored at 37° C., 150 μL aliquots were analyzed by HPLC (the sample was mixed before taking an aliquot, and no visible precipitate was observed even before mixing).

The analysis of the solution after centrifugation showed presence of MAD in the precipitate. Using HPLC, MitoADCA (MAD), loss of one alanyl-DCA (MAD-ADCA), loss of three alanyl-DCA (i.e., TPP-Tris-OH) and the alanyl-DCA (ADCA) were tracked. MAD was detected and monitored at 268 nm with retention time of 18.08 min, Mito-A-DCA missing 1 alanyl DCA at 268 nm with retention time of 17.13 min, total amount of MAD and Mito-A-DCA missing 1 alanyl DCA at 268 nm, TPP-Tris-OH at 268 nm with retention time of 14.6 min, and alanyl DCA at 205 nm with retention time of 9.5 min. The MAD half-life in cell media at 500 μM was measured as ~20 h. TPP-Tris-OH starts appearing in HPLC only after 10 h in media. Alanyl-DCA is released as a result of hydrolysis instead of DCA.

In a further study, Mito-ADCA stability testing was carried out in rat serum. 0.5 mg/mL solutions 18% rat serum were prepared and analyzed by HPLC. Mito-ADCA was detected at 268 nm with a retention time of 18.08 min over time of 4500 min in 18% rat serum. Mito-ADCA exhibited a half-life in serum of around 7 h. Alanyl-DCA is released as a result of hydrolysis instead of DCA. After 2 d a peak of TPP-Tris-OH was observed. The amount of TPP-Tris-OH corresponded to 76% of the original. Mito-ADCA was stable in water for 2 days without signs of decomposition.

Example 3: Synthesis of TPP-alanino-DCA (TPP-ADCA)

The solution of 4-bromobutyltriphenylphosphonium bromide and sodium azide in the mixture of ethanol ("EtOH") and water was stirred under reflux for overnight. The solvent was evaporated and residue was dissolved in DCM-EtOH (9:1) and filtered with filter paper. The filtrate was concentrated to give a desired compound (99% Yield). The product was confirmed by NMR.

The solution of TPP-butyl azide and triphenylphosphine in the mixture of THF/MeOH/H2O was stirred at 70° C. for 1 h. The mixture was concentrated and the resulting residue was dissolved in DCM. The compound was extracted with 0.2M HCl and water fraction was washed with DCM. The water fraction was lyophilized to give a desired compound (97% Yield). The product (TPP-butyl-amine-HCl) was confirmed by NMR. The synthesis route of TPP-butyl-amine-HCl is shown below in Scheme X.

Scheme X. A synthesis route of TPP-butyl-amine-HCl

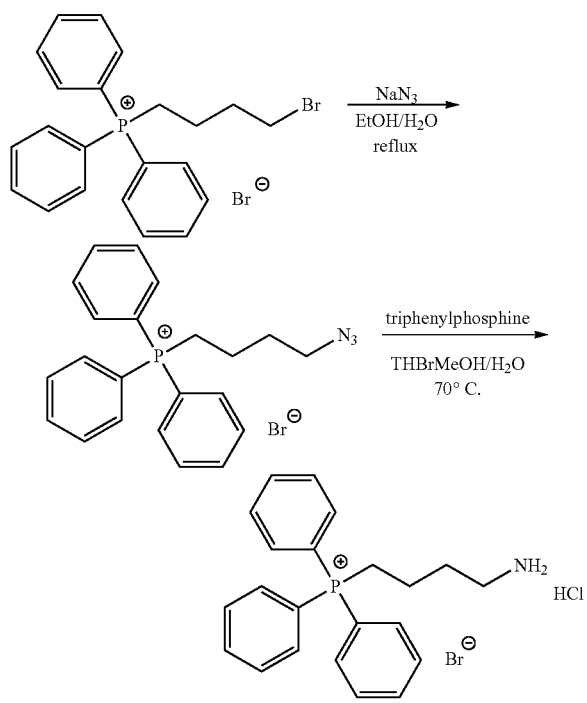

To the solution of TPP-amine hydrochloride and pyridine in DCM, dichloroacetic anhydride (DCA2O) was added dropwise at rt. After being stirred for 30 min, additional pyridine and DCA2O were added. After 30 min solvent was evaporated and the residue was purified by column chromatography (95:5=DCM:MeOH). 75.5 mg 63% yield. HPLC showed single peak, and the product was further confirmed by NMR and MS. The synthesis route of TPP-alanino-DCA from TPP-butyl-amine-HCl is shown below.

Scheme XI. A synthesis route of TTP-alanino-DCA

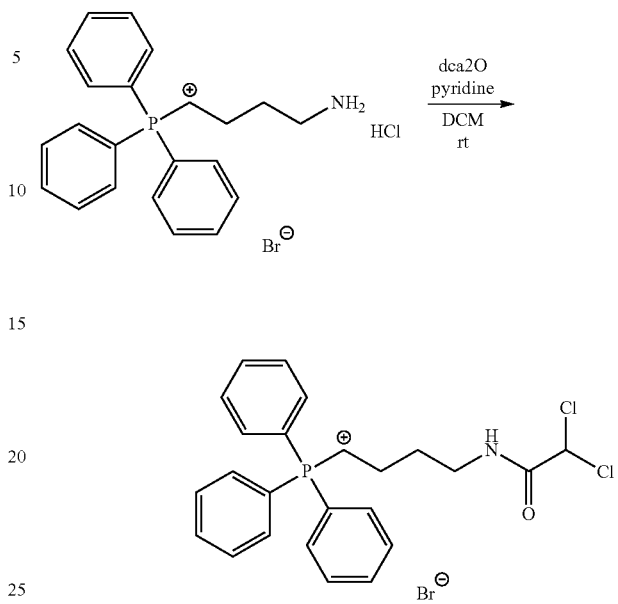

Example 4: Synthesis & Stability of TPP-bis-ADCA

The solution of Bis-Boc-Lysine, TPPamine hydrochloride, Et3N, and NHS in DMF, EDC was added at room temperature (RT). After being stirred overnight at rt, AcOEt was added and mixture was washed with 0.1% H2SO4 in Brine, NaHCO$_3$, and Brine, and dried over MgSO4. The residue was purified with column chromatography (CHCl3: MeOH, 10:0 to 8:2). 512 mg was obtained (36% Yield). Single peak on HPLC and NMR confirmed the product.

The compound was dissolved in DCM, and TFA was added at rt. After being stirred for 1 h at RT, the mixture was concentrated. The residue was dissolved in DCM, and pyridine and DCA2O were added. After being stirred for 1 h at RT, the mixture was washed with 0.1% H2SO4 in Brine, NaHCO$_3$, and Brine. The residue was purified with column chromatography. 165 mg was obtained (80% Yield). NMR and MS confirmed product. HPLC showed two peaks. And the second small peak is expected to be compound where one of DCA was replaced by TFA. The synthesis route of TPP-Bis-ADCA is shown in Scheme XII.

Scheme XII. A synthesis route of TPP-Bis-ADCA

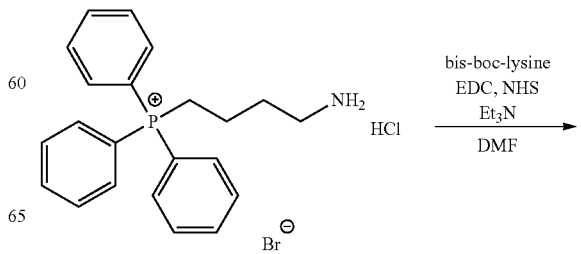

83
-continued

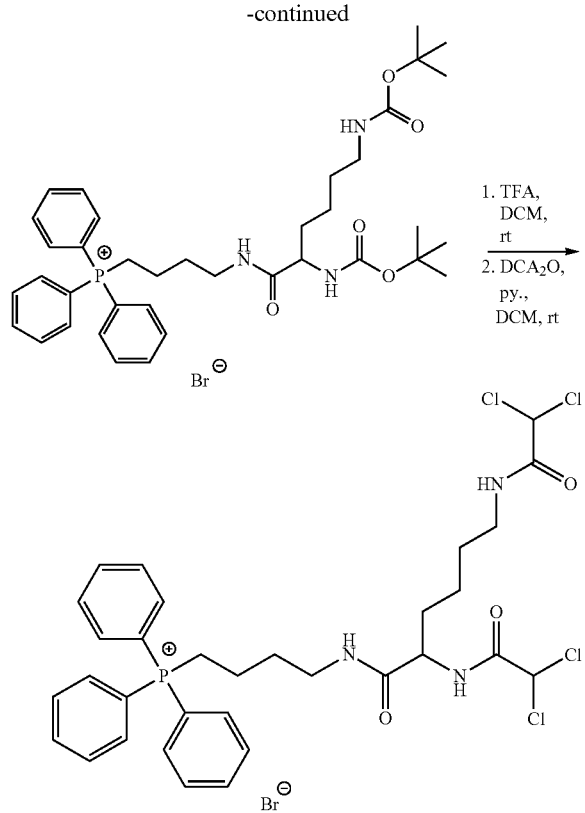

Stability of TPP-bis-ADCA

Stability of TPP-bis-ADCA in rat serum and water was carried out using 500 μg/mL solution in 18% rat serum. The solution was analyzed by HPLC for two days. This compound was stable in both serum and water, 2% decomposition was observed after 2 days in serum, no DCA was detected.

Example 5: Synthesis and Stability of TPP-ib-DCA

Synthesis of TPP-ib-DCA

Synthesis of TPP-ib-DCA was carried out in two steps starting from TPP-aminehydrochloride. A solution of DCC (260 mg, 1.26 mmol) in DCM (5 mL) was added to a stirred solution of TPP-amine (500 mg, 1.26 mmol), acid (1.05 mmol), HOSu (213 mg, 1.57 mmol), and triethylamine (290 μL, 2.1 mmol) and the resulting mixture was stirred overnight. The urea was filtered off and the residue was purified by column chromatography using 5 to 20% MeOH in DCM. Yield 258 mg.

A solution of dichloroacetic anhydride (220 μL, 1.43 mmol) and (4-(2-hydroxy-2-methylpropanamido)butyl)triphenylphosphonium bromide (200 mg, 0.48 mmol) in DCM (10 mL) was stirred overnight at room temperature. The solution was concentrated and the product was purified by precipitation into diethyl ether two times. The product was purified by chromatography.

(4-(2-(2,2-dichloroacetoxy)-2-methylpropanamido)butyl)triphenylphosphonium bromide: 1H NMR (400 MHz, DMSO-d6, ppm): δ 1.47-1.70 (m, 8H, CH2, 2×CH3), 1.95 (m, 2H, CH2), 3.43-3.54 (m, 4H, 2×CH2), 6.45 (s, 1H, CH), 7.71-7.81 (m, 15H, CHar). MS (ESI, positive mode): m/z calculated for [C28H31Cl2NO3P]+=530.1, found 530.1.

84

The synthesis route of TPP-ib-DCA is shown below.

Scheme XIII. A synthesis route of TPP-ib-DCA

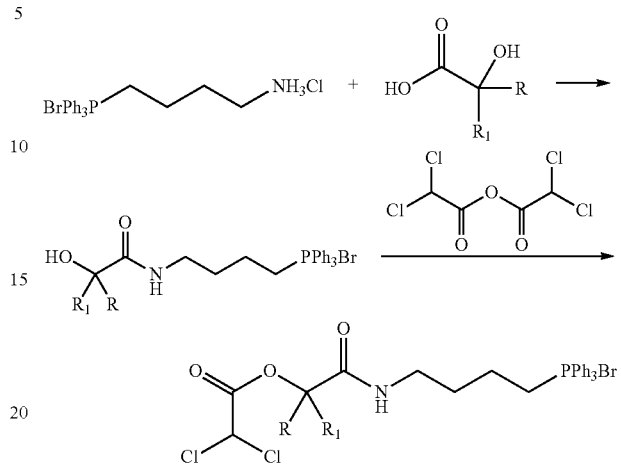

Stability of TPP-ib-DCA

Hydrolytic stability of TPP-ibDCA in serum, and in water was studied. A 500 μg/mL solution of TPP-ib-DCA in water, and in 18% rat serum was analyzed by HPLC using the method for Mito-ADCA/DCA detection described above. The total area of absorbance peaks of each compound on HPLC chromatograms at a specified detection wavelength was monitored over time: TPP-ib-DCA in 18% rate serum was detected at 268 nm with retention time of 17.7 min; DCA in 18% rate serum was detected at 205 nm with retention time of 4.8 min; TPP-ib-DCA in water was detected at 268 nm with retention time of 17.7 min; DCA in water was detected at 205 nm with retention time of 4.8 min. The hydrolysis in serum seems to be slower than MitoDCA. Surprisingly, the appearance of free DCA is delayed relative to the disappearance of the ester. In water, hydrolysis of TPP-ib-DCA stops halfway likely due to the acidification of the solution.

Example 6: Anti-tumor Activity of Palmitic-Tris-DCA (PDCA) Nanoparticles

Synthesis of Palmitic-Tris-OH

Palmitic acid (7.7 g, 30 mmol), Tris (3.6 g, 30 mmol), and EEDQ (11.1 g, 45 mmol) were added to EtOH, and the mixture was stirred under reflux for 2 days. Mixture was cooled to RT, then added EtOAc. After 30 min, solid was filtered (6.3 g, 58% yield). 1H NMR (DMSO-d6): 0.84 (t, 3H), 1.22 (m, 24H), 1.45 (t, 2H), 2.10 (t, 2H), 3.50 (d, 6H), 4.76 (t, 2H), 7.09 (s, 1H).

Synthesis of Palmitic-Tris-DCA (PDCA)

To the suspension of Palm-Tris-OH (0.60 g, 1.67 mmol) in CH2Cl2, dichloroacetic anhydride (2.5 mL, 16.7 mmol) was added drop wise under N2 atmosphere. The mixture was stirred for o/n. After reaction, EtOAc was added, and the mixture was washed with NaHCO3, and dried over MgSO4. After concentration, the residue was purified by column chromatography (Silica gel, 9:1 Hexane:EtOAC to 4:1 Hexane:EtOAc). (82% Yield, 0.95 g). PDCA was characterized by using NMR and Mass spectroscopy. HPLC analysis was conducted by monitoring the compound using 210 and 220 nm wavelengths and eluting with a gradient of water/acetonitrile with 0.1% TFA. 1H NMR (CDCl3): 0.86 (t, 3H), 1.25 (m, 24H), 1.59 (t, 2H), 2.18 (t, 2H), 4.70 (s, 6H), 5.70 (s, 1H), 6.00 (s, 3H); ESI MS (M+H) 690.2.

The synthesis route of Palmitic-Tris-DCA is shown below.

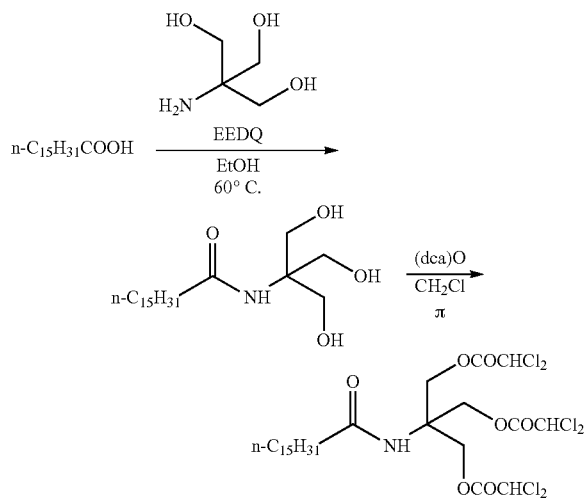

Scheme XIV. A synthesis route of Palmitic-Tris-DCA

Preparation of PDCA Encapsulated Nanoparticles

PDCA was encapsulated in PLGA-PEG block copolymers to prepare PDCA encapsulated nanoparticles (NPs). PLGA-PEG-OH was used to prepare non-targeted (NT)-NPs, while PLGA-PEG-TPP was used to prepare Targeted (T)-NPs. Some T-NP formulations were prepared using mixture of PLGA-PEG-OH and PLGA-PEG-TPP polymers for varying charge and better stability of encapsulated PDCA. Table 1 provides various characterization details of these nanoparticles. As expected the NT-PDCA-NP formulations show small sizes and negative charges, while the T-PDCA-NP formulations show small size with positive charge. The loadings increase with increase of feed PDCA amount with respect to polymer and encapsulation efficiencies are 50-100% range. All the targeted NP compositions showed some degradation of DCA from PDCA and the respective PDCA analogs with the loss of one DCA or two DCA were visible in the HPLC.

TABLE 1

Characterization of PDCA-NPs

| (Polymer ratio and Drug Feed) | Size (nm) | PDI | Zeta potential (mV) | % Loading | % EE |
|---|---|---|---|---|---|
| NT-100-20% | 54 | 0.18 | −18 | 13.8 | 69 |
| NT-100-40% | 68 | 0.23 | −18 | 26.1 | 65 |
| NT-100-60% | 80 | 0.18 | −19 | 41.6 | 71 |
| NT-90-T-10-40% | 82.5 | 0.24 | 24.4 | 30 | 75 |
| NT-75-T-25-40% | 77.6 | 0.293 | 32.7 | 29 | 74 |
| NT-50-T-50-40% | 76.8 | 0.243 | 33.3 | 22 | 55 |
| NT-25-T-75-40% | 73.3 | 0.218 | 36.6 | 21 | 52 |
| T-100-40% | 81.1 | 0.208 | 37.7 | 16 | 40 |

Stability of PDCA-NPs

The stability of PDCA encapsulated nanoparticles was tested over a period of 7 weeks. A 20 mg/mL batch of PDCA-NPs were stored at 4° C. for 46 days without stabilizer and in another batch of 20 mg/mL of PDCA-NPs were stored with sucrose as a stabilizer for 9 and 32 days at −20° C. Size, charge, PDCA concentrations were monitored over time.

To summarize, the size, charge and drug concentrations were unchanged for samples stored at −20° C. with the stabilizer. However hydrolysis of PDCA resulting in loss of DCA increased with time for the sample stored at 4° C. The shelf life at 4° C. was about 14 days. At −20° C. no significant degradation was observed even after 32 days.

Cytotoxicity Studies

Next the cytotoxicity ability of PDCA and PDCA-NPs were studied in A549 and HCT16 cells to evaluate the ability of these new formulations with respect to NaDCA. The $IC_{50}$ (Table 2) indicates the enhanced efficacy of PDCA and its NP version than the NaDCA. The $IC_{50}$ value of NaDCA is ~20 mM, while the PDCA is ~204 µM, while the PDCA-NPs showed around 30 µM.

TABLE 2

IC50 of PDCA-NPs

| | A549 cells | | HCT116 cells | |
|---|---|---|---|---|
| Drug | IC50 (µM) (24 + 48 h) | IC50 (µM) (72 h) | IC50 (µM) (24 + 48 h) | IC50 (µM) (72 h) |
| NaDCA | >20000 | >20000 | >20000 | >20000 |
| PDCA | 204 | 175 | | |
| T/NT-PDCA-NPs | 44 | 30 | 46 | 26 |

Anti-tumor Activity of PDCA-NPs in Xenograft Mouse Model

Xenograft studies with the T/NT-PDCA-NPs showed over 20% tumor reduction after two and three weeks of 5 on/2 off dosing with respect to untreated animals in a mouse xenograft model. Once the dosing stopped the tumor growth did not show any regression.

Example 7: Nanoparticles with Palm-Tris-β-alanino-DCA (PADCA)

Synthesis of Palm-Tris-β-alanino-DCA (PADCA)

PADCA was prepared in two steps starting with Palm-tris-OH and reacted with Boc protected beta-alanine using EDC, DMAP reagents in DMF solvent. DMF was removed and the product was purified by column chromatography. To the solution of Boc protected compound in DCM, TFA was added and stirred. After concentration, this residue was dissolved in DCM, and triethylamine was added. To this mixture, DCA anhydride was added drop-wise, and the mixture was stirred. The solution was washed with 0.1% H2SO4-Brine, and dried over MgSO4. After concentration, the residue was purified by column chromatography. 1H NMR (CDCl3): 0.86 (t, 3H), 1.25 (m, 24H), 1.57 (t, 2H), 2.20 (t, 2H), 2.64 (t, 6H), 3.64 (m, 6H), 4.46 (s, 6H), 5.96 (s, 3H); 6.01 (s, 1H), 7.21 (m, 3H), ESI MS (M+H) 890.2.

The synthesis route of Palm-Tris-β-alanino-DCA is shown in Scheme XV.

Scheme XV. A synthesis route of Palm-Tris-β-alanino-DCA

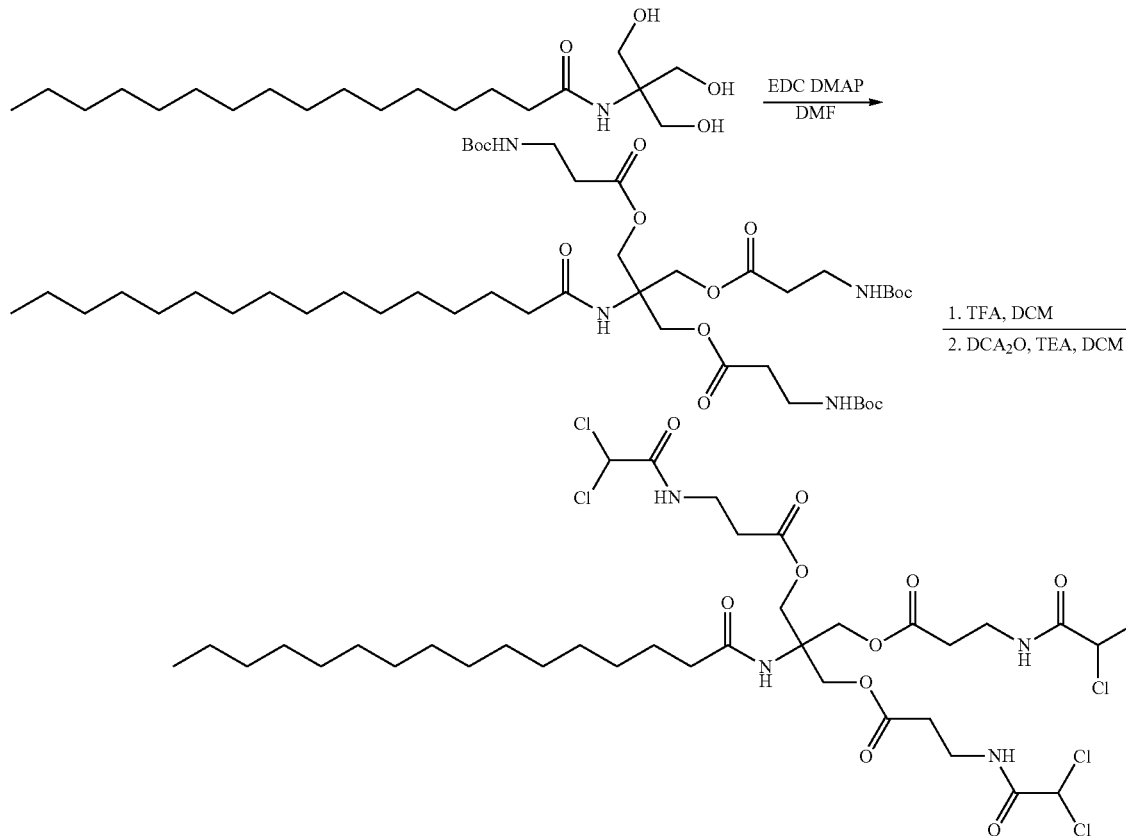

Preparation of PADCA Encapsulated Nanoparticles

PADCA was encapsulated in PLGA-PEG block copolymers to prepare PADCA encapsulated nanoparticles (NPs). PLGA-PEG-TPP was used to prepare Targeted-NPs. The T-PADCA-NP formulations showed a size of 169 nm. Loadings and EE values were determined using HPLC to be 22% and 56% respectively.

The IC50 value for the free PADCA is ~400 µM in A549 cells.

Example 8: Nanoparticles with Hydrophobic Metformin

Synthesis of Hydrophobic Metformin

To metformin hydrochloride salt (2 g, 12 mmoles), 1M sodium hydroxide (14 mL) was added and stirred at room temperature for 30 minutes. The aqueous solvent was removed in vacuum and the resultant powder was dissolved in cold methanol. The undissolved sodium chloride was removed by filtration and the filtrate was concentrated to afford free metformin as white powder (1.8 g).

The synthesis route of palmitoxy carbonyl metformin is shown in Scheme XVI.

Scheme XVI. A synthesis route of palmitoxy carbonyl metformin

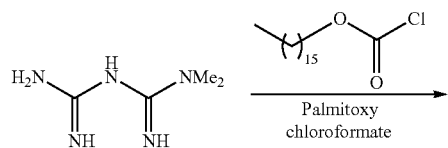

-continued

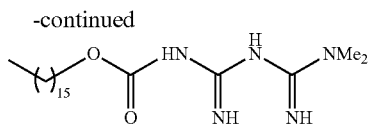

To free metformin (1 g, 7.7 mM) in acetonitrile (10 mL), palmitoxy chloroformate (2.5 mL, 7.73 mM) was added drop wise at ice-bath temperature. The reaction mixture was poured into water and then acidified to pH 5.0 using 0.1 M hydrochloric acid and then extracted with dichloromethane. The combined organic layer was dried over magnesium sulfate and concentrated in vacuum to obtain white powder. The resultant powder was recrystallized in 10% methanol in ethyl acetate to obtain pure colorless powder of palmitoxy carbonyl metformin (0.8 g, 26%).

1HNMR (DMSO-d6): 10.50 (s, 1H, NH), 7.84 (3bs, 3H, NH), 4.08 (t, 2H, CH2), 2.94 (bs, 6H, CH3), 1.60-1.30 (m, 2H, CH2), 1.28-1.22 (m, 26H, CH2), 0.84 (t, 3H, CH3). 13CNMR (DMSO-d6): 160.4, 154.6, 152.0, 66.0, 31.8, 29.5, 29.46, 29.43, 29.42, 29.2, 29.1, 28.6, 25.6, 22.6, 14.4. Molecular formula: C21H43N5O2; Molecular weight: 397.6, Mass obtained: 398.4 (M+1), 295.2 (2M+1).

The chemical formula of palmitoxy carbonyl metformin is shown below.

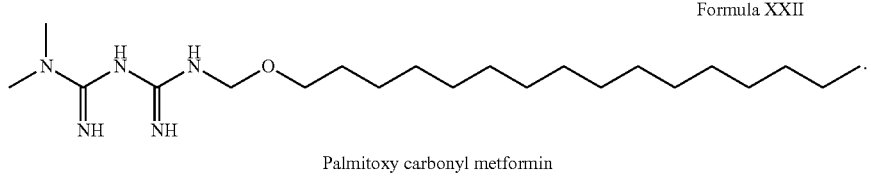 [SMILES: CCCCCCCCCCCCCCCCOCNC(=N)NC(=N)N(C)C]

Formula XXII

Palmitoxy carbonyl metformin

Preparation of Hydrophobic Metformin Encapsulated Nanoparticles

Both the targeted polymer (50 mg/mL) and palmitoxy carbonyl metformin (10 mg/mL) were dissolved in dimethylformamide separately to produce stock solutions of both compounds. To load 40% palmitoxy carbonyl metformin into nanoparticle, 100 uL of polymer and 200 uL of metformin were mixed in 700 uL of DMF. The resultant polymer-drug mixed solution was drop-wise added into a 10 mL of water over a period of 1 min while stirring at 900 RPM at RT. The resultant mixture was stirred at the same RPM and temperature for 2 h. The mixture was filtered through a 0.45 μm PVDF filter to remove any visible particulate matter and then transferred into 100K mol wt cut-off amicon centrifugal filter. The mixture was centrifuged at 3000 RPM at 4 degree Celsius for four times upon adding water each time. The nanoparticle solution was then concentrated by centrifugation to 1 mL. The resultant T-PalmMeformin-NPs solution was characterized for size, charge and drug loading and encapsulation efficiency.

TABLE 3

Dynamic light scattering data for nanoparticles with hydrophobic metformin

| Feed | Size (nm) | PDI | Zeta potential (mV) | % Loading | % EE |
|---|---|---|---|---|---|
| 40% | 148.0 | 0.28 | 36.0 | 16.4 | 41.0 |

Cytotoxicity Studies

Next the cytotoxicity ability of PalmMetformin and NPs were studied in A549 and HCT16 cells to evaluate the ability of these new formulations with respect to Meformin. The IC50 (Table 4) indicates the enhanced efficacy of PalmMeformin and its NP version than the Meformin. The IC50 values of Metformin is >0.5 mM, while the PalmMetformin is ~16 μM, while the T-NPs and NT-NPs showed around 12 μM in A549 cells. Similarly IC50 values of Metformin is >0.5 mM, while the PalmMetformin is ~34 μM, while the T-NPs showed around 35 μM in HCT116 cells.

TABLE 4

| | IC50 of Meformin-NPs | | | |
|---|---|---|---|---|
| | A549 cells | | HCT116 cells | |
| Drug | IC50 (μM) (24 + 48 h) | IC50 (μM) (72 h) | IC50 (μM) (24 + 48 h) | IC50 (μM) (72 h) |
| Meformin | >500 | >500 | >500 | >500 |
| PalmMetformin | 16 | 16 | 34 | 34 |
| T-PalmMetformin-NPs | 12 | 12 | 35 | 35 |

Example 9: Synthesis of Octyl Oxamate

To a solution of 1-Octanol (500 mg, 3.84 mmoles) in dichloromethane (10 mL), oxaloyl chloride (970 mg, 7.68 mmoles) was added drop wise over a period of 5 minutes, while keeping the reaction mixture in ice bath. The reaction mixture was stirred at room temperature for 1 hour. The mixture was concentrated to remove unreacted oxalyl chloride and solvent. The crude was re-dissolved in dichloromethane and cooled to ice-bath temperature. Then ammonia (130 mg, 7.68 mmoles) in methanol was added drop wise. The mixture was stirred for 15-20 min. Water was added to the mixture and the precipitate obtained was filtered. The filtrate was separately extracted using dichloromethane. The combined fractions were concentrated using rotavapor to get a colorless solid. The product was further column purified using ethyl acetate and hexane to get the pure product.

The synthesis route of octyl oxamate is shown below.

Scheme XVII. A synthesis route of octyl oxamate

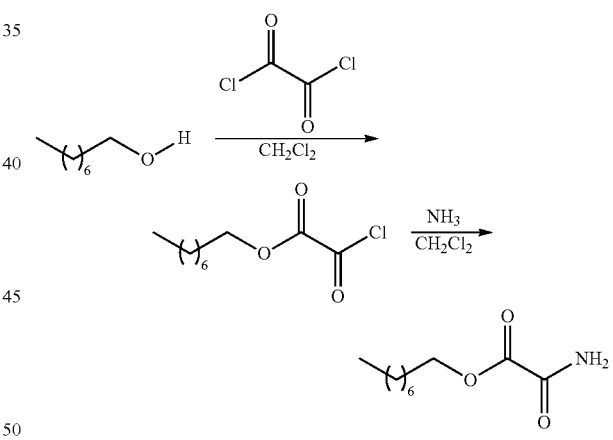

Example 10: Nanoparticles with Octyl 3-bromopyruvate (Octyl-3-BP) and Tetradecyl 3-bromopyruvate (Td-3-BP)

Synthesis of Octyl-3BP (octyl 3-bromopyruvate) and Tetradecyl 3-bromopyruvate (Td-3-BP)

The RB flask was charged with MgSO$_4$ (2.88 g, 24 mmol) and 30 mL of dry DCM under argon atmosphere, after which concentrated H$_2$SO$_4$ (0.32 mL, 6 mmol) was added. After stirring for 5 min, 3-bromopyruvic acid, (3-BP) (3 g, 18 mmol) and 1-octanol (0.95 mL, 6 mmol) were added. The reaction mixture was stirred overnight at RT. The reaction was quenched by slow addition of water and then aq. NaHCO$_3$ at 0° C. The organic layer was separated, the aqueous layer was washed with DCM (2×50 mL) and combined organic fractions were washed with brine (100 mL). The solvent was evaporated to give octyl 3-bromo-2-oxopropanoate as yellowish oil (1.54 g, 92%) or tetradecyl 3-bromo-2-oxopropanoate as a white solid (1.97 g, 91%).

Octyl 3-bromo-2-oxopropanoate: 1H NMR (400 MHz, CDCl3, ppm): δ 0.87 (t, 3H, J=6 Hz, CH3), 1.22-1.40 (m, 10H, 5×CH2), 1.70-1.77 (m, 2H, CH2), 4.30 (t, 2H, J=8 Hz, OCH2), 4.32 (s, 2H, BrCH2); 13C NMR (400 MHz, CDCl3, ppm): 14.05 (CH3), 22.59 (CH2), 25.66 (CH2), 28.27 (CH2), 29.09 (2×CH2), 29.27 (BrCH2), 30.74 (CH2), 67.27 (OCH2), 159.40 (C=O), 184.64 (C=O).

Tetradecyl 3-bromo-2-oxopropanoate: 1H NMR (400 MHz, CDCl3, ppm): δ 0.87 (t, 3H, J=6 Hz, CH3), 1.27-1.40 (m, 22H, 11×CH2), 1.70-1.76 (m, 214, CH2), 4.29-4.32 (m, 5H, OCH2, BrCH2); 13C NMR (400 MHz, CDCl3, ppm): 14.10 (CH3), 22.67 (CH2), 25.69 (CH2), 28.28 (CH2), 29.10 (CH2), 29.29 (BrCH2), 29.33 (CH2), 29.42 (CH2), 29.51 (CH2), 29.56 (CH2), 29.63 (CH2), 29.68 (CH2), 30.74 (CH2), 31.90 (CH2), 67.28 (OCH2), 159.43 (C=O), 184.63 (C=O).

The synthesis route of Octyl-3-BP and tetradecyl 3-BP is shown below.

Scheme XVIII. A synthesis route of Octyl-3-BP and tetradecyl 3-BP

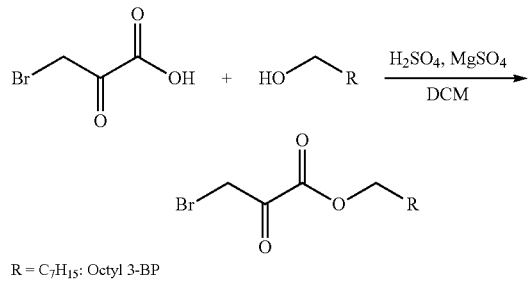

R = C7H15: Octyl 3-BP
R = C13H27: Tetradecyl 3-BP

Quantification of Octyl-3BP through detection of Fmoc-L-cysteine amide adduct

For HPLC calibration 100 μL of Tris in DMF (10 mg/mL), 100 μL of Fmoc-L-cysteine amide in DMF (10 mg/mL) and 5, 10, 25, 50 μL of 1 mg/mL or 10, 20 μL of 10 mg/mL solution of Octyl-3-BP in acetonitrile were mixed in an Eppendorf tube. The mixture war kept for 10 min at room temperature with occasional vortexing. After 10 minutes the solution was diluted to 0.5 mL with acetonitrile, containing 0.1% TFA. The resulting 5, 10, 25, 50, 100, 200 μg/mL solutions (with respect to added Octyl-3-BP) were analyzed by HPLC with detection at 268 nm using 70 to 95% acetonitrile (0.1% TFA) gradient over 10 minutes at 60° C. column temperature. For sample analysis, 25 or 50 μL of NP solution (5 mg/mL in water) was added to the same mixture of Tris and Fmoc-Cys. After 10 min at room temperature, the mixture was diluted to 0.5 mL with acetonitrile (0.1% TFA) for analysis.

The reaction scheme of Octyl-3-BP and Fmoc-L-cysteine amide is shown below.

Scheme XIX. A reaction scheme of Octyl-3-BP and Fmoc-L-cysteine amide

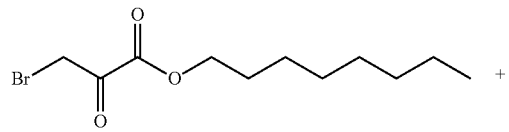

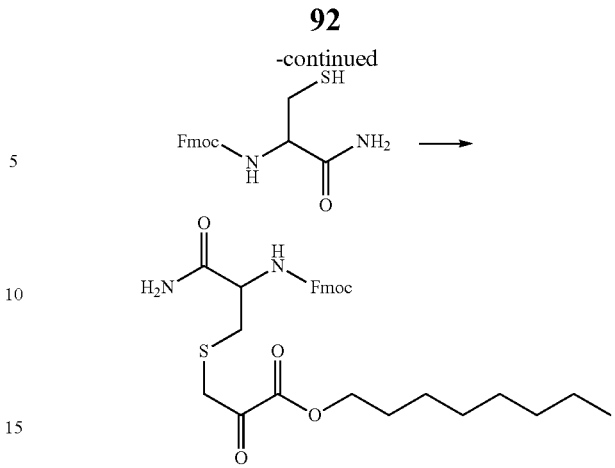

Preparation of Octyl-3-BP Encapsulated Nanoparticles and Tetradecyl 3-BP Encapsulated Nanoparticles Targeted nanoparticles of Octyl 3-BP and Tetradecyl 3-BP were prepared in two methods: 1) regular nanoprecipitation method where drug and polymer were mixed together and added to water to generate nanoparticles, 2) a two stage method, where first micelles were prepared of Octyl 3-BP or Tetradecyl 3-BP by adding and acetonitrile solution them to water and stir for 2 hours, then to this solution polymer solution in acetonitrile was added and stirred for further two hours to get larger sized nanoparticles than the previous method.

Targeted nanoparticles with encapsulated Octyl 3-BP and Tetradecyl 3-BP were prepared by nanoprecipitation approach. A mixture of Octyl 3-BP or Tetradecyl 3-BP and PLGA-PEG-TPP in acetonitrile (1 mL, 5 mg/mL with respect to polymer, 2.5 mg/mL of Octyl 3-BP or 5 mg/mL of Tetradecyl 3-BP) was added dropwise to 10 mL of water while stirring and stirred for 2 h. Particles were purified by Amicon filtration 3 times. The resulting Octyl 3-BP nanoparticles had z-average diameter of 66.03 nm (PDI=0.268) and zeta-potential of 48.1 mV. The loading was 3.4% with encapsulation efficiency of 6.9%. The resulting Tetradecyl 3-BP nanoparticles had z-average diameter of 89.53 nm (PDI=0.153) and zeta-potential of 45.7 mV. The loading was 14.16% with encapsulation efficiency of 14.16%.

Larger nanoparticles for OMM targeting were prepared by a following method. Octyl 3-BP or Tetradecyl 3-BP in acetonitrile (1 mL, 5 mg/mL) was added dropwise to 10 mL of water and stirred for 2 h. After 2 h a solution of PLGA-PEG-TPP in acetonitrile (1 mL, 5 mg/mL) was added dropwise and the resulting mixture was stirred for 2 h. Particles were purified by Amicon filtration 3 times. The resulting Octyl 3-BP nanoparticles had z-average diameter of 219.2 nm (PDI=0.178) and zeta-potential of 47.2 mV. The loading was 7.7% with encapsulation efficiency of 7.7% (Table 5). The resulting Tetradecyl 3-BP nanoparticles had z-average diameter of 278.8 nm (PDI=0.273) and zeta-potential of 47.9 mV. The loading was 11.11% with encapsulation efficiency of 11.11%.

The targeted Octyl 3-BP nanoparticle size could be increased further by increasing the ratio of Octyl 3-BP to the targeted polymer. For instance, by starting with 1 mL of 10 mg/mL solution of Octyl 3-BP the nanoparticles that had z-average diameter of 269.6 nm (PDI=0.212) and zeta-potential of 40.0 mV. The loading was 16.0% with encapsulation efficiency of 8.0%.

TABLE 5

Characterization of octyl 3-BP nanoparticles

| Feed of Alkyl-3BP | Size (nm) | PDI | Zeta potential (mV) | % Loading | % EE |
|---|---|---|---|---|---|
| 100% -Regular-Oct3BP | 66 | 0.268 | 48.1 | 3.4 | 6.9 |
| 100%- 2 stage-Oct3BP | 219.2 | 0.178 | 47.2 | 7.7 | 7.7 |
| 100% -Regular-Td3BP | 89.5 | 0.153 | 45.7 | 14.2 | 14.2 |
| 100%- 2 stage-Td3BP | 278.8 | 0.273 | 47.9 | 11.1 | 11.1 |

Stability of Oct3BP-NPs

The storage stabilities of Oct3-BP encapsulated nanoparticles were monitored over a period of 7 weeks. Two batches of Oct3BP-NPs were stored at −20° C. for 17 and 46 days with sucrose stabilizer and thawed and stored at 4° C. One batch of Oct3BP-NPs were stored at −4° C. without stabilizer. Size, charge, and 3BP concentration were monitored.

Minimal changes were observed for nanoparticle size and charge regardless of their storage conditions. The loading decreases with time for both 4° C., and −20° C. storage conditions. Storage at −20° C. has only a small beneficial effect on stability compared to when stored at 4° C. without any stabilizer. The shelf life for 10% loss in concentration was observed after 22 days at 4° C. and 27 days at −20° C.

Example 11: Nanoparticles with Palmityl Geldanamycin (C16-Geld)

Synthesis of Palmityl Geldanamycin (C16-Geld)

To the solution of Geldanamycin (100 mg, 179 mmoles) in 50 mL of dichloromethane, hexadecylamine (216 mg, 895 mmoles) was added and stirred at RT for 3 days. Solvent was removed and the residue was purified by column chlormatography (Rf 0.5 Hex:AcOEt=1:1) 83% Yield. Purity of the product was confirmed by NMR and MS, and HPLC analysis. The synthesis route of Palmityl Geldanamycin is shown below.

Scheme XX. A synthesis route of Palmityl Geldanamycin

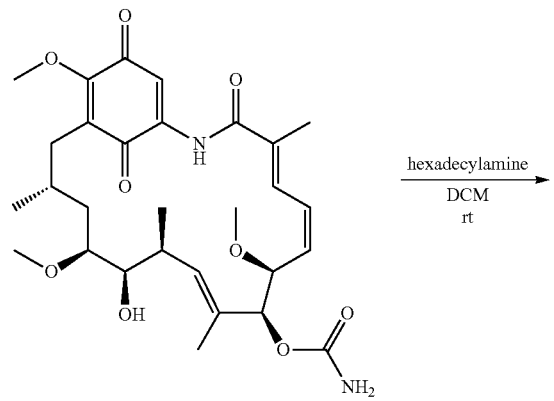

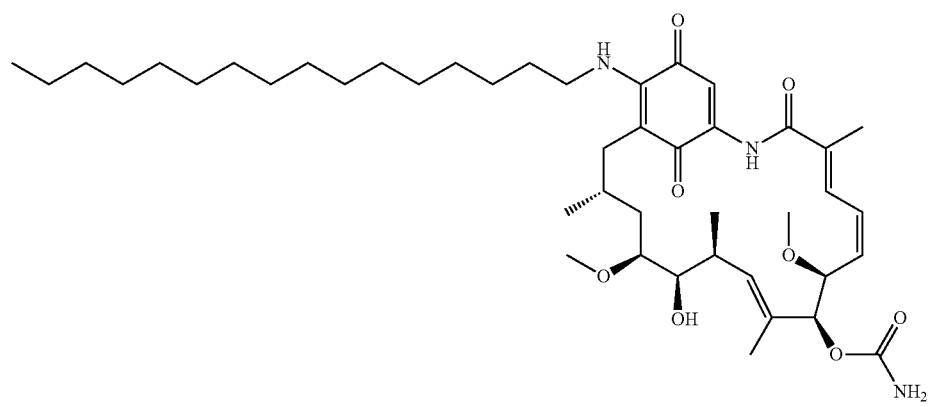

Preparation of C16-Geld Encapsulated Nanoparticles

Encapsulation of C16-Geld in the targeted polymers was carried out with 40% and 60% drug feeds (Table 6). Both the feeds showed very high encapsulation efficiency and loadings, which is in contract to when attempt to encapsulate the free Geldanamycin in the nanoparticles.

TABLE 6

Characterization of C16-Geld Encapsulated Nanoparticles

| Feed of C16-Geld | Size (nm) | PDI | Zeta potential (mV) | % Loading | % EE |
|---|---|---|---|---|---|
| 40% | 113.8 | 0.269 | 51 | 39.1 | 97.8 |
| 60% | 127.1 | 0.246 | 51.7 | 54.1 | 90.1 |

Example 12: Nanoparticles with PalmTrisEthoxyEthanol (PTEE)

Synthesis of PalmTrisEthoxyEthanol (PTEE)

PTEE was prepared from ethoxy ethanol in two steps. In first step, ethoxy ethanol (1.98 g, 22 mmoles) was dissolved in dichloromethane. To this solution, succinic anhydride (2 g, 20 mmoles) was added along with catalytic amount of dimethyl amino pyridine (121 mg, 2 mmoles). Solution was stirred under reflux overnight. Solution was concentrated and product was purified by column chromatography using DCM and MeOH. Yield: 88%.

In the second step, the Palm-Tris-OH (309 mg, 1 mmol) and ethoxyethylsuccinic acid (1.14 g, 6 mmoles) along with EDC (1.15 g, 6 mmoles), and DMAP (121 mg, 1 mmol) was dissolved in DMF and stirred overnight at 60° C. The reaction mixture was washed with 0.1% sulfuric acid containing brine, followed by wash with bicarbonate solution and finally brine solution. The solution was concentrated and purified by column chromatography using hexane and acetone. And the product PTEE was isolated in 92% yield. Purity of the product was confirmed by NMR and HPLC. The synthesis route of PalmTrisEthoxyEthanol is shown in Scheme XXI.

Scheme XXI. A synthesis route of PalmTrisEthoxyEthanol

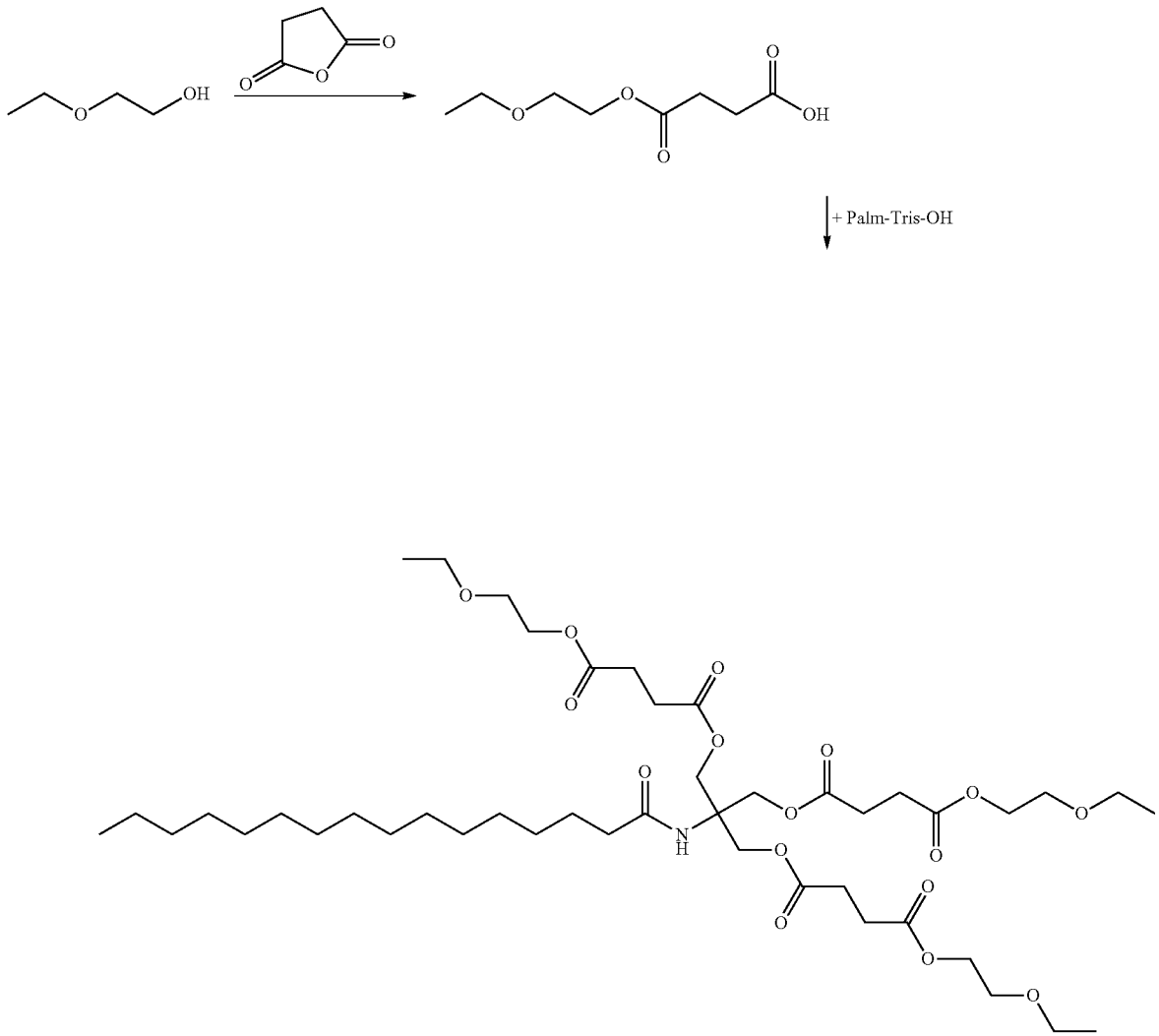

Preparation of Palm TrisEthoxyEthanol Encapsulated Nanoparticles

PTEE was encapsulated in to the nanoparticles using 40% Feed. The NPs were 234 nm in size, and 0.128 PDI and 52 mV charge. PTEE loading is 30% and EE is 75% from the HPLC analysis.

Example 13: Synthesis of Palmityl-bis-Lonidamine (PalmbisLND)

PalmbisLND was prepared in two steps. In step one, palmitic acid (2 g) was reacted with 2-amino-2-methyl-propan-1,3-diol using EEDQ in ethanol for overnight. Next day the solvent was evaporated and residue was dissolved in ethyl acetate. This solution was washed with 0.1% sulfuric acid containing brine for three times and dried with magnesium sulfate. Product was purified by recrystallization in Ethylacetate and hexane mixture. Purity of Palmbis-OH was checked by TLC and NMR.

In the second step Lonidamine (LND, 138 mg, 145 mmol), 50 mg of palmbis-OH was dissolved in DMF, and to this solution EDC (135 mg), DMAP (17 mg) was added and stirred at 40 C overnight. Next day, to this solution ethyl acetate was added and washed with 0.1% sulfuric acid containing brine for three times and dried with magnesium sulfate. 137 mg of product was recovered after purification by column chromatography using hexane and ethylacetate mixture. Purity of PalmbisLND was checked by TLC and NMR.

The synthesis route of palmityl-bis-Lonidamine is shown below.

Example 14: Nanoparticles with Ethyl Lonidamine (EtLND) and Octyl Lonidamine (OctLND)

Synthesis of Ethyl Lonidamine (EtLND) and Octyl Lonidamine (OctLND)

To the solution of lonidamine (LND, 161 mg, 0.5 mmol) in DMF, Alcohol (EtOH; 1 mL or Octanol; 0.5 mL), and DMAP in DMF, EDC was added at rt. Then the mixture was stirred for 0.5 h or 3 h, respectively. AcOEt was added to the mixture and washed with 0.1% $H_2SO_4$—Brine (×4) and dried over $MgSO_4$. After evaporation, the residue was purified by flash column over silica gel (9:1=Hexane; EtOAc). Products were isolated and analyzed for purity using HPLC and NMR. Et-LND (84% yield) Octyl-LND (58% yield).

The synthesis route of Ethyl Lonidamine (EtLND) and Octyl Lonidamine (OctLND) is shown below.

Scheme XXIII. A synthesis route of Ethyl Lonidamine (EtLND) and Octyl Lonidamine (OctLND)

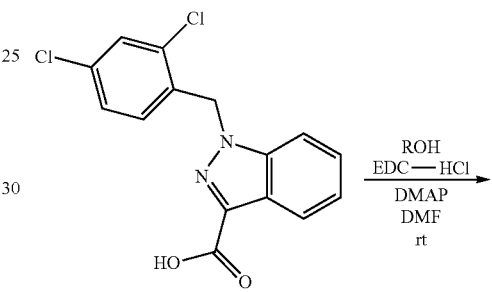

Scheme XXII. A synthesis route of palmityl-bis-Lonidamine

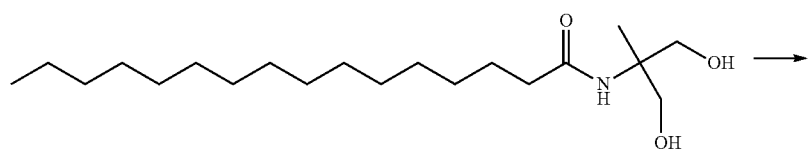

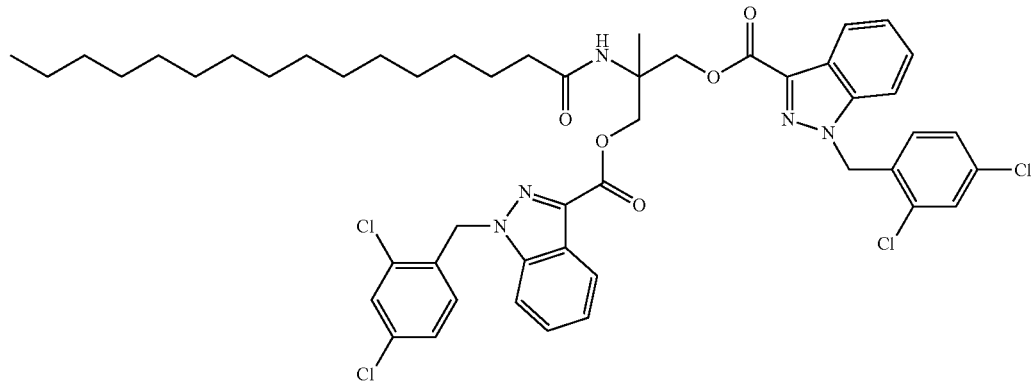

-continued

[Structure: 1-(2,4-dichlorobenzyl)-1H-indazole-3-carboxylate with OR group]

Preparation of Ethyl Lonidamine (EtLND) Encapsulated Nanoparticles and Octyl Lonidamine (OctLND) Encapsulated Nanoparticles Nanoparticle synthesis was attempted with both EtLND and OctLND. Summary of the data was shown in the Table 7. EtLND did not load well in to the nanoparticles, but the OctLND showed better loading and EE at different feed ratios demonstrating improvement of hydrophobicity and better encapsulation property upon octyl chain attachment.

TABLE 7

Characterization of EtLND and OctLND Nanoparticles

| Feed | Size (nm) | PDI | Zeta potential (mV) | % Loading | % EE |
|---|---|---|---|---|---|
| 40%-EtLND | 62 | 0.298 | 50 | 0.23 | 0.57 |
| 40%-OctLND | 167 | 0.166 | 50.7 | 17.9 | 44.7 |
| 60%-OctLND | 177 | 0.145 | 50.4 | 35.5 | 59.2 |

Example 15: Nanoparticles with Tetradecyl-cyanohydroxycinnamic Acid (TdCHC)

Synthesis of Tetradecyl-cyanohydroxycinnamic Acid (TdCHC)

A suspension of EDC (760 mg, 3.96 mmol) in DCM (5 mL) was added to a stirred mixture of α-cyano-4-hydroxycinnamic acid (500 mg, 2.64 mmol), DMAP (64 mg, 0.528 mmol), and pyridine (630 mg, 7.92 mmol) in DCM (15 mL). The resulting mixture was stirred overnight at room temperature, diluted with DCM (100 mL) washed with 0.1 M HCl, NaHCO₃ and brine (100 mL each). The organic fraction was dried over MgSO₄ and concentrated. The residue was purified by column chromatography on silica gel twice using 0-70% Ethyl acetate in hexanes as an eluent. Yield 20 mg (2%), white powder, 96% pure by HPLC.

The synthesis route of tetradecyl-cyanohydroxycinnamic acid is shown below.

Scheme XXIV. A synthesis route of tetradecyl-cyanohydroxycinnamic acid

[Reaction scheme: α-cyano-4-hydroxycinnamic acid + HO-(CH₂)₆-... with EDC, DMAP, Py in DCM]

-continued

[Structure: tetradecyl ester of α-cyano-4-hydroxycinnamic acid]

Preparation of Tetradecyl-cyanohydroxycinnamic Acid Encapsulated Nanoparticles

The encapsulation was performed on a 10 mL scale by using T-Polymer (PL-42) or at a concentration of 5 mg/mL in DMF with 10, 20, 30% feed of TdCHC. After stirring for 2 hours the nanoparticle solutions were clear and had a yellow color. The particles were purified by Amicon filtration, no apparent aggregation was observed, but the 30% feed particles filtered slowly. During filtration through 0.45 µm filter 30% feed particles created large resistance and remained mostly on a filter (Table 8).

TABLE 8

Characterization of Tetradecyl-cyanohydroxycinnamic acid Nanoparticles

| Feed of TdCHC | Size (nm) | PDI | Zeta potential (mV) | % Loading | % EE |
|---|---|---|---|---|---|
| 10% | 68.2 | 0.348 | 48.6 | 6.6 | 21.9 |
| 20% | 86.9 | 0.254 | 44.8 | 9.7 | 32.4 |
| 30% | 95.6 | 0.151 | 24.3 | 0.7 | 2.3 |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A compound selected from the group consisting of:

[Structure: Br-CH₂-C(=O)-C(=O)-O-alkyl chain]

[Structure: long alkyl chain with amide linkage to macrocyclic compound with NH₂ carbamate, containing quinone and lactone features]

101
-continued
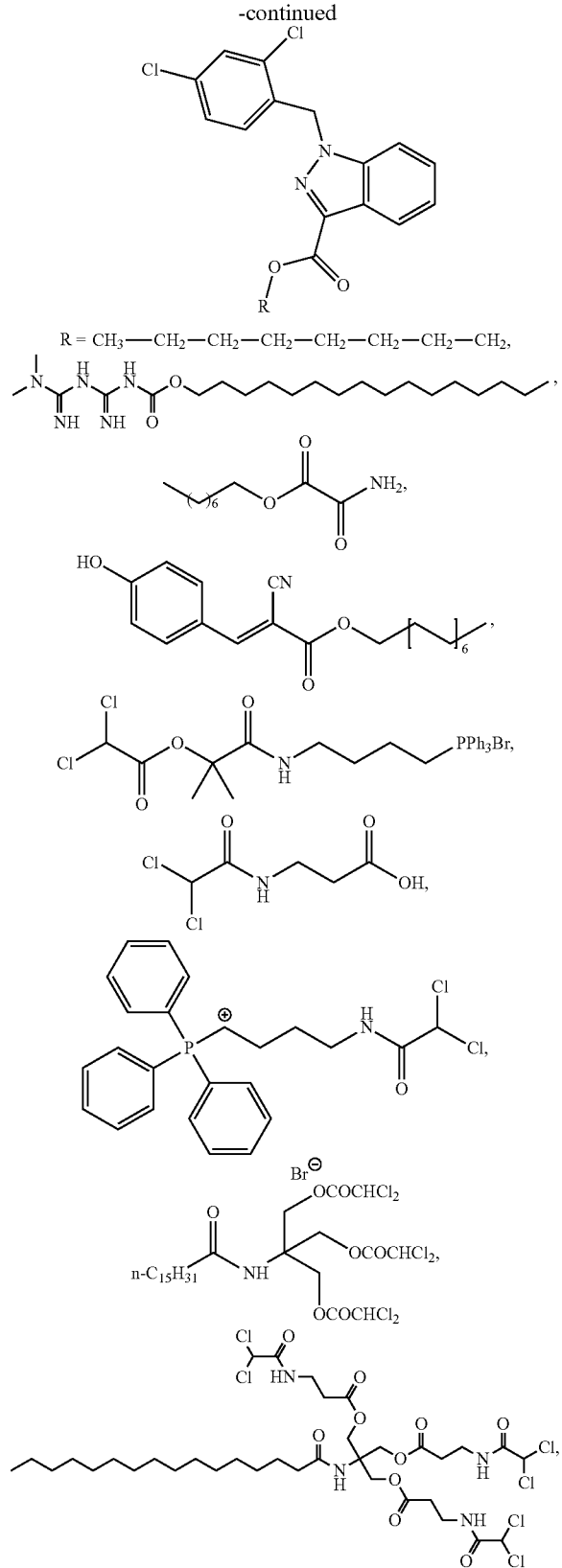
102
-continued
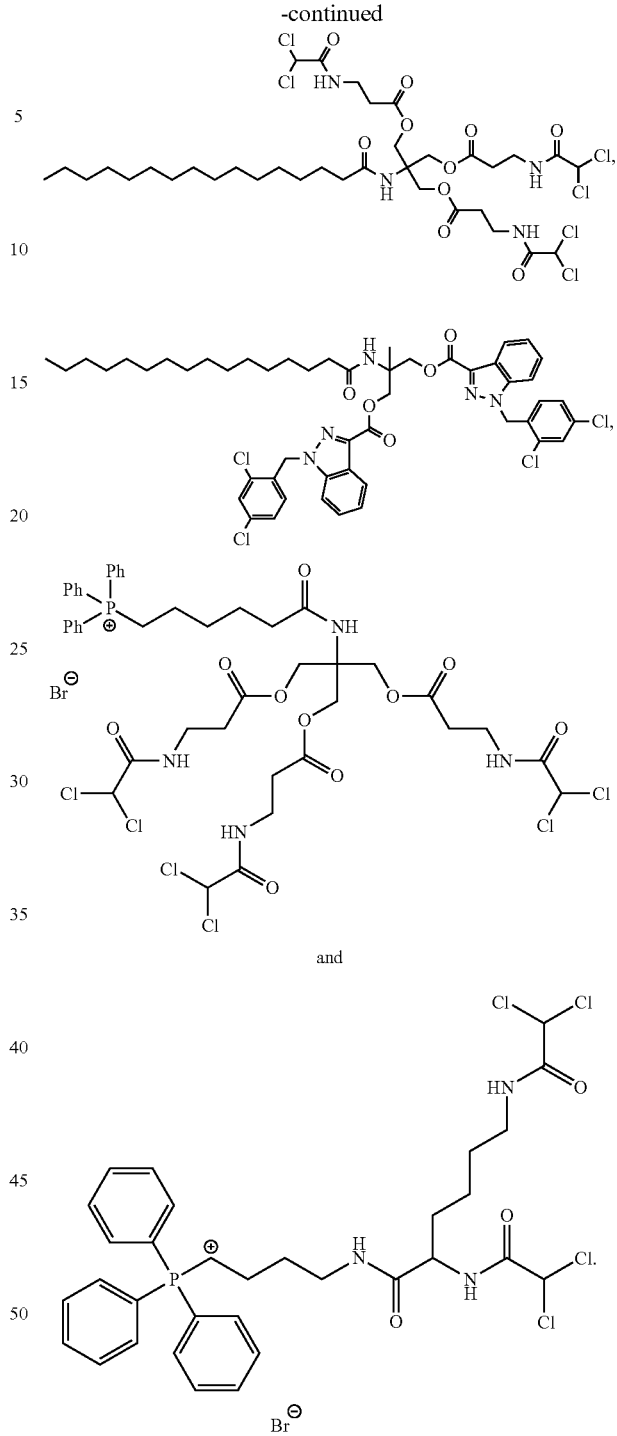
and
2. A composition comprising a compound according to claim 1 and a pharmaceutically acceptable carrier.
3. A method of treating cancer comprising administering to a patient in need thereof, a composition according to claim 2.
* * * * *

UNITED STATES PATENT AND TRADEMARK OFFICE
CERTIFICATE OF CORRECTION

| | | |
|---|---|---|
| PATENT NO. | : 10,478,492 B2 | Page 1 of 2 |
| APPLICATION NO. | : 15/660256 | |
| DATED | : November 19, 2019 | |
| INVENTOR(S) | : David Kolb, Petr Ledin and Tsukasa Mizuhara | |

It is certified that error appears in the above-identified patent and that said Letters Patent is hereby corrected as shown below:

In the Specification

Column 2, Line 44, replace "an modulator" with --a modulator--.
Column 4, Line 32, replace "kinase, isozyme 1 (PDK1)" with --kinase isozyme 1 (PDK1)--.
Column 5, Line 61, replace "The terms" with --The term--.
Column 13, Line 2, replace "defines" with --defined--.
Column 14, Line 25, replace "alkylaryl, alkylheteroaryl" with --alkylaryl, and alkylheteroaryl--.
Column 15, Line 54, replace "as defined herein" with --are as defined herein--.
Column 20, Line 23, replace "include a moiety" with --includes a moiety--.
Column 24, Line 33, replace "targeting moiety can" with --targeting moiety that can--.
Column 25, Line 23, replace "to delivery itself" with --to deliver itself--.
Column 25, Line 48, replace "mitochondria targeting moiety" with --a mitochondria targeting moiety--.
Column 25, Line 53, replace "mitochondrial target moiety" with --a mitochondrial targeting moiety--.
Column 25, Line 65, replace "targeting moiety TM" with --targeting moiety (TM)--.
Column 27, Line 21, replace "modulator are" with --modulators are--.
Column 27, Line 56, replace "HSP90 inhibitor" with --HSP90 inhibitors--.
Column 27, Line 59, replace "betulinic acid, and resveratrol" with --betulinic acid, resveratrol--.
Column 29, Line 8, replace "ATP)" with --ATP--.
Column 29, Line 29, replace "Oxamate has shown" with --Oxamate was shown--.
Column 30, Line 20, replace "derivatives ethoxyethanol" with --derivatives of ethoxyethanol--.
Column 31, Lines 32-33, replace "36.8 nMjnbn and 6.4 nM" with --36.8 nM and 6.4 nM--.
Column 31, Line 48, replace "GLS1inhibitors" with --GLS1 inhibitors--.
Column 31, Line 65, replace "Pemetrexed& Derivatives" with --Pemetrexed & Derivatives--.
Column 32, Line 21, replace "cellul, and/or mitochondria" with --cells, and/or mitochondria--.
Column 45, Line 40, replace "the composition metformin" with --the composition is metformin--.
Column 49, Line 52, replace "Preferable" with --Preferably--.
Column 49, Line 53, replace "are based generation" with --are based on generation--.
Column 50, Line 25, replace "triazole linker" with --triazole linker)--.
Column 50, Line 64, replace "before the all of the" with --before all of the--.

Signed and Sealed this
Third Day of November, 2020

Andrei Iancu
*Director of the United States Patent and Trademark Office*

CERTIFICATE OF CORRECTION (continued)

Column 51, Line 48, replace "hydolyzable" with --hydrolyzable--.
Column 52, Line 4, replace "poly(vinyl acetate" with --poly(vinyl acetate)--.
Column 54, Line 49, replace "tert-butanol" with --tert-butanol)--.
Column 57, Line 27, replace "(i.e., Ci5 to C25)" with --(i.e., C15 to C25)--.
Column 58, Line 12, replace "first due their" with --first due to their--.
Column 58, Line 19, replace "In most case" with --In most cases--.
Column 59, Line 20, replace "and a another end first" with --and on another end a first--.
Column 61, Line 44, please replace "5□C above" with --5°C above--.
Column 62, Line 48, replace "The compositions designed" with --The compositions are designed--.
Column 66, Line 3, replace "known art" with --known in the art--.
Column 67, Line 16, replace "enhance and/or prolonging" with --enhance and/or prolong--.
Column 67, Line 64, replace "for example, and" with --for example, any--.
Column 69, Line 37, replace "tumor cell kill" with --tumor cell killing--.
Column 70, Line 8, replace "to enhance body's own" with --to enhance the body's own--.
Column 73, Line 12, replace "delivery active agents" with --deliver active agents--.
Column 75, Line 34, replace "art in include" with --art and include--.
Column 82, Lines 49-52, replace "And the second small peak is expected to be compound where one of DCA was replaced by TFA." with --The second small peak is expected to be a compound where one of DCA was replaced by TFA.--.
Column 85, Lines 64-65, replace "and in another batch of 20 mg/mL of PDCA-NPs were stored with sucrose" with --and another batch of 20 mg/mL of PDCA-NPs was stored with sucrose--.
Column 85, Line 66, replace "Size, charge, PDCA concentrations" with --Size, charge, and PDCA concentrations--.
Column 89, Lines 20-21, replace "into a 10 mL" with --into 10 mL--.
Column 95, Line 6, replace "which is in contract to" with --which is in contrast to--.

In the Claims

Claim 1, Column 102, Lines 1-10, replace " 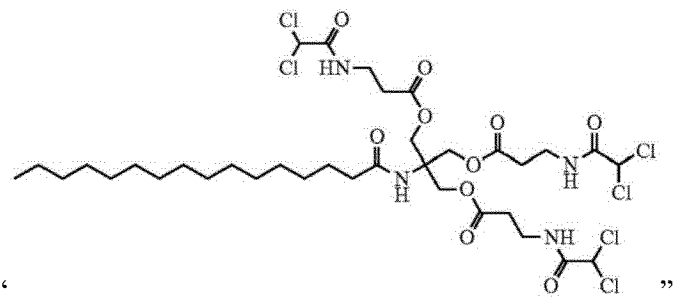 "

with -- 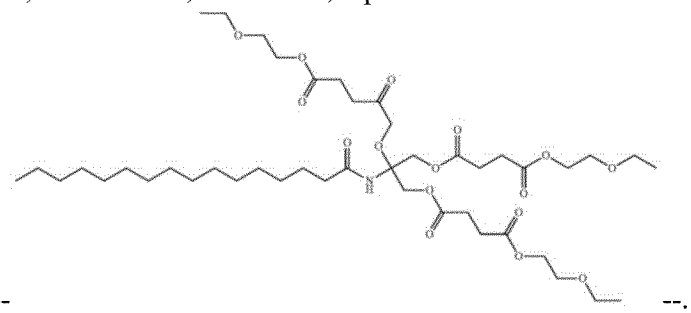 --.